US007351562B2

(12) United States Patent
Chatterjee et al.

(10) Patent No.: US 7,351,562 B2
(45) Date of Patent: Apr. 1, 2008

(54) RIBULOSE 1,5-BISPHOSPHATE CARBOXYLASE/OXYGENASE POLYPEPTIDES AND RELATED POLYNUCLEOTIDES

(75) Inventors: Ranjini Chatterjee, Belmont, CA (US); Michelle M. Chen, Belmont, CA (US); Ranjan Patnaik, San Jose, CA (US); Stephen L. Schmidt, Belmont, MA (US)

(73) Assignee: Codexis, Inc., Redwood City, CA (US)

( * ) Notice: Subject to any disclaimer, the term of this patent is extended or adjusted under 35 U.S.C. 154(b) by 265 days.

(21) Appl. No.: 10/425,332

(22) Filed: Apr. 28, 2003

(65) Prior Publication Data

US 2004/0038262 A1 Feb. 26, 2004

Related U.S. Application Data

(60) Provisional application No. 60/375,910, filed on Apr. 26, 2002.

(51) Int. Cl.

*C12N 9/12* (2006.01)
*C12N 15/00* (2006.01)
*C12P 21/06* (2006.01)
*C07H 21/04* (2006.01)

(52) U.S. Cl. .................. 435/189; 435/69.1; 435/320.1; 536/23.2

(58) Field of Classification Search ................ 435/183, 435/69.1, 252.1, 320.1; 536/23.1, 234
See application file for complete search history.

(56) References Cited

OTHER PUBLICATIONS

Andrews et al., Kinetics and subunit interactions of ribulose bisphosphate carboxylase-oxygenase from cyanobacterium, *Synechoccus* sp. JBC 256(16): 8445-8451, 1981.*

Shinozaki et al., Molecular cloning and sequence analysis of the cyanobacterial gene for the large subunit of ribulose-1,5-biphosphate carboxylase/oxygenase. PNAS., 1983, vol. 80: 4050-4054.*

Shinozaki et al., Genes for the large and small subunits of ribulose-1,5-biphosphate carboxylase/oxygenase constitute a single operon in a cyanobacterium *Anacystis nidulans* 6301. Mol. Gen Genet., 1985, vol. 200: 27-32.*

Shinozaki et al., Molecular cloning and sequence analysis of the cyanobacterial gene for the large subunit of ribulose-1,5-biphosphate carboxylase/oxygenase. PNAS., 1983, vol. 80: 4050-4054.*

Broun et al., Catalytic plasticity of fatty acid modification enzymes underlying chemical diversity of plant lipids. Science, 1998, vol. 282: 1315-1317.*

Witkowski et al., Conversion od b-ketoacyl synthase to a malonyl decarboxylase by replacemnt of the active-site cysteine with glutamine. Biochemistry, 1999, vol. 38: 11643-11650.*

Seffernick et al., Melamine deaminase and Atrazine chlorohydrolase: 98 percent identical but functionally different. J. Bacteriol., 2001, vol. 183 (8): 2405-2410.*

Whisstock et al., Prediction of protein function from protein sequence and structure. Q. Rev. Biophys., 2003, vol. 36(3): 307-340.*

Andrews et al., 1984, "Active-site Carbamate Formation and Reaction-Intermediate-Analog Binding by Ribulosebisphosphate Carboxylase/Oxygenase in the Absence of its Small Subunits," *Proc. Natl. Acad. Sci.* 81:3660-3664.

Badger et al., 1985, "A Model for $HCO_3$ Accumulation and Photosynthesis in the Cyanobacterium *Synechococcus* sp.," *Plant Physiol.* 77:465-471.

Badger et al., 1982, "Photosynthesis and Inorganic Carbon Usage by the Marine Cyanobacterium, *Synechococcus* sp.," *Plant Physiol.* 70:517-523.

Blanchard et al., 2003, "Current State of the Data in the Cyanobacterium *Synechococcus* prepared for the DOE Genomes to Life Project. Carbon Sequestration in *Synechococcus* Sp.: From Molecular Machines to Hierarchical Modeling," *NGCR* pp. 1-9.

Crosbie et al., 2003, "Dispersal and Phylogenetic Diversity of Nonmarine Picocyanobacteria, Inferred from 16S rRNA Gene and cpcBA-Interhenic Spacer Sequence Analyses," *Applied and Environmental Microbiology* 69(9):5716-5721.

Fuller et al., 2003, "Clade-Specific 16S Ribosomal DNA Oligonucleotides Reveal the Predominance of a Single Marine *Synechococcus* Clade throughout a Stratified Water Column in the Red Sea," *Applied and Environmental Micr obiology* 69(5):2430-2443.

Giovannoni et al., 1988, "Evolutionary Relationships among Cyanobacteria and Green Chloroplasts," *Journal of Bacteriology* 170(8):3584-3592.

Golden et al., 1989, "Genetic Relationship of Two Highly Studied *Synechococcus* Strains Designed *Anacystis nidulan*," *Journal of Bacteriology* 171(1):24-29.

Holtman et al., 2005, "High-Throughput Functional Analysis of the *Synechococcus* elongates PCC 7942 Genome," *DNA Research* 12:103-115.

Honda et al., 1999, "Detection of Seven Major Evolutionary Lineages in Cyanobacteria Based on the 16S rRNA Gene Sequence Analysis with New Sequences of Five Marine *Synechococcus* Strains," *J. Mol. Evol.* 48:723-739.

(Continued)

*Primary Examiner*—Rebecca E. Prouty
*Assistant Examiner*—Ganapathirama Raghu
(74) *Attorney, Agent, or Firm*—Dechert LLP

(57) ABSTRACT

The present invention relates to novel ribulose-1,5-bisphosphate carboxylase/oxygenase polypeptides and the polynucleotides that encode them. The invention also provides related host cells and methods.

9 Claims, 4 Drawing Sheets

OTHER PUBLICATIONS

Ong et al., 1991, "Phycoerythins of Marine Unicellular Cyanobacteria," *J. Biol. Chem.* 266(15):9515-9527.

Rasmussen et al., 1998, "Fingerprinting of Cyanobacteria Based on PCR with Primers Derived from Short and Long Tandemly Repeated Repetitive Sequences," *Applied and Environmental Microbiology* 64(1):265-272.

Robertson et al., 2001, "Phylogenetic analyses of *Synechococcus* strains (cyanobacteria) using sequences of 16S rDNA . . . " *International Journal of Systematic and Evolutionary Microbiology* 51:861-871.

Seo et al., 2003, "The Ph ylogenetic Relationships of Cyanobacteria inferred from 16S rRNA, gyrB, rpoC1 and rpoD1 gene sequences," *J. Gen. Appl. Microbiol.* 49:191-203.

Shestakov, 2002, "Gene-Targeted and Site-Directed Mutagenesis of Photosynthesis Genes in Cyanobacteria," *Photosynthesis Research* 73:279-284.

Shinozaki et al., 1983, "Molecular Cloning and Sequence Analysis of the Cyanobacterial Gene for the Large Subunit of Ribolose-1,5-bisphosphate carboxylase/oxygenase," *Proc. Natl. Acad. Sci.* 80:4050-4054.

Stanier et al., 1971, "Purification and Properties of Unicellular Blue-Green Algae (Order Chroococcales)," *Bacteriological Reviews* 35(2):171-205.

ATCC Product Description for *Synechococcus* sp.pp. 1-14, 2006.

Ting et al., "Cyanobacterial Photosynthesis in the Oceans: the Origins and Significance of Divergent Light-Harvesting Strategies," *TRENDS in Microbiology* 10(3):134-142.

Turner et al., "Molecular Phylogeny of Nitrogen-Fixing Unicellular Cyanobacteria," *Bol. Bull. Acad. Sin.* 42:181-186.

Genebank Accession No. BAA03076 [gi:485794], Apr. 14, 2005.

Genebank Accession No. CAE08233 [gi:33639225], Apr. 17, 2005.

Genebank Accession No. ABB57456 [gi:81169116], Nov. 8, 2005.

Genebank Accession No. Q8DIS5 [gi:81742950], Apr. 18, 2006.

Genebank Accession No. P27568 [gi:132028], Apr. 18, 2006.

Genebank Accession No. P00879 [gi:20141627], Jun. 27, 2006.

Genebank Accession No. Q44176 [gi:3183143], Apr. 18, 2006.

Genebank Accession No. P00880 [gi:59802957], Jun. 27, 2006.

* cited by examiner

Gene replacement vector 1 (pGR-1)

*Afl III generates compatible end with Nco I (both 5' and 3' flanking sequences contain Nco I site)

SEQUENCE LISTING

```
<160> NUMBER OF SEQ ID NOS: 61

<210> SEQ ID NO 1
<211> LENGTH: 1845
<212> TYPE: DNA
<213> ORGANISM: Synechococcus PCC 6301 rbcLS
<220> FEATURE:
<221> NAME/KEY: CDS
<222> LOCATION: (1)...(1419)
<223> OTHER INFORMATION: rbcL
<220> FEATURE:
<221> NAME/KEY: CDS
<222> LOCATION: (1510)...(1845)
<223> OTHER INFORMATION: rbcS

<400> SEQUENCE: 1

atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                  10                  15

tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
            20                  25                  30
```

-continued

```
ctg ctg gcg gct ttc cgc ttc agc cct cag ccg ggt gtc cct gct gac          144
Leu Leu Ala Ala Phe Arg Phe Ser Pro Gln Pro Gly Val Pro Ala Asp
         35                  40                  45

gaa gct ggt gcg gcg atc gcg gct gaa tct tcg acc ggt acc tgg acc          192
Glu Ala Gly Ala Ala Ile Ala Ala Glu Ser Ser Thr Gly Thr Trp Thr
     50                  55                  60

acc gtg tgg acc gac ttg ctg acc gac atg gat cgg tac aaa ggc aag          240
Thr Val Trp Thr Asp Leu Leu Thr Asp Met Asp Arg Tyr Lys Gly Lys
 65                  70                  75                  80

tgc tac cac atc gag ccg gtg caa ggc gaa gag aac tcc tac ttt gcg          288
Cys Tyr His Ile Glu Pro Val Gln Gly Glu Glu Asn Ser Tyr Phe Ala
                 85                  90                  95

ttc atc gct tac ccg ctc gac ctg ttt gaa gaa ggg tcg gtc acc aac          336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt          384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc          432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac          480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt          528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc          576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc          624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa          672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc          720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aaa gaa          768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc acc          816
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg          864
Ala Asn Thr Thr Leu Ala Lys Trp Cys Arg Asp Asn Gly Val Leu Leu
        275                 280                 285

cac atc cac cgt gca atg cac gcg gtg atc gac cgt cag cgt aac cac          912
His Ile His Arg Ala Met His Ala Val Ile Asp Arg Gln Arg Asn His
    290                 295                 300

ggg att cac ttc cgt gtc ttg gcc aag tgt ttg cgt ctg tcc ggt ggt          960
Gly Ile His Phe Arg Val Leu Ala Lys Cys Leu Arg Leu Ser Gly Gly
305                 310                 315                 320

gac cac ctc cac tcc ggc acc gtc gtc ggc aaa ctg gaa ggc gac aaa         1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa         1056
Ala Ser Thr Leu Gly Phe Val Asp Leu Met Arg Glu Asp His Ile Glu
            340                 345                 350
```

-continued gct gac cgc agc cgt ggg gtc ttc ttc acc caa gat tgg gcg tcg atg 1104
Ala Asp Arg Ser Arg Gly Val Phe Phe Thr Gln Asp Trp Ala Ser Met
355 360 365 ccg ggc gtg ctg ccg gtt gct tcc ggt ggt atc cac gtg tgg cac atg 1152
Pro Gly Val Leu Pro Val Ala Ser Gly Gly Ile His Val Trp His Met
370 375 380 ccc gca ctg gtg gaa atc ttc ggt gat gac tcc gtt ctc cag ttc ggt 1200
Pro Ala Leu Val Glu Ile Phe Gly Asp Asp Ser Val Leu Gln Phe Gly
385 390 395 400 ggc ggc acc ttg ggt cac ccc tgg ggt aat gct cct ggt gca acc gcg 1248
Gly Gly Thr Leu Gly His Pro Trp Gly Asn Ala Pro Gly Ala Thr Ala
405 410 415 aac cgt gtt gcc ttg gaa gct tgc gtc caa gct cgg aac gaa ggt cgc 1296
Asn Arg Val Ala Leu Glu Ala Cys Val Gln Ala Arg Asn Glu Gly Arg
420 425 430 gac ctc tac cgt gaa ggc ggc gac atc ctt cgt gaa gct ggc aag tgg 1344
Asp Leu Tyr Arg Glu Gly Gly Asp Ile Leu Arg Glu Ala Gly Lys Trp
435 440 445 tcg cct gaa ctg gct gct gcc ctc gac ctc tgg aaa gag atc aag ttc 1392
Ser Pro Glu Leu Ala Ala Ala Leu Asp Leu Trp Lys Glu Ile Lys Phe
450 455 460 gaa ttc gaa acg atg gac aag ctc taa ggagcctctg actatcgctg 1439
Glu Phe Glu Thr Met Asp Lys Leu *
465 470 ggggagtgag cgttgctgcg taaagctttc tccccagcct ttcgacttaa cctttcagga 1499 tttctgaatc atg agc atg aaa act ctg ccc aaa gag cgt cgt ttc gag 1548
Met Ser Met Lys Thr Leu Pro Lys Glu Arg Arg Phe Glu
475 480 485 act ttc tcg tac ctg cct ccc ctc agc gat cgc caa atc gct gca caa 1596
Thr Phe Ser Tyr Leu Pro Pro Leu Ser Asp Arg Gln Ile Ala Ala Gln
490 495 500 atc gag tac atg atc gag caa ggc ttc cac ccc ttg atc gag ttc aac 1644
Ile Glu Tyr Met Ile Glu Gln Gly Phe His Pro Leu Ile Glu Phe Asn
505 510 515 gag cac tcg aat ccg gaa gag ttc tac tgg acg atg tgg aag ctc ccc 1692
Glu His Ser Asn Pro Glu Glu Phe Tyr Trp Thr Met Trp Lys Leu Pro
520 525 530 ctg ttt gac tgc aag agc cct cag caa gtc ctc gat gaa gtg cgt gag 1740
Leu Phe Asp Cys Lys Ser Pro Gln Gln Val Leu Asp Glu Val Arg Glu
535 540 545 tgc cgc agc gaa tac ggt gat tgc tac atc cgt gtc gct ggc ttc gac 1788
Cys Arg Ser Glu Tyr Gly Asp Cys Tyr Ile Arg Val Ala Gly Phe Asp
550 555 560 565 aac atc aag cag tgc caa acc gtg agc ttc atc gtt cat cgt ccc ggc 1836
Asn Ile Lys Gln Cys Gln Thr Val Ser Phe Ile Val His Arg Pro Gly
570 575 580 cgc tac taa 1845
Arg Tyr *

<210> SEQ ID NO 2
<211> LENGTH: 472
<212> TYPE: PRT
<213> ORGANISM: Synechococcus PCC 6301
<220> FEATURE:
<221> NAME/KEY: DOMAIN
<222> LOCATION: (1)...(472)
<223> OTHER INFORMATION: Synechococcus rbcL

<400> SEQUENCE: 2

Met Pro Lys Thr Gln Ser Ala Ala Gly Tyr Lys Ala Gly Val Lys Asp

-continued

```
1               5                   10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430
```

-continued

Asp Leu Tyr Arg Glu Gly Gly Asp Ile Leu Arg Glu Ala Gly Lys Trp
435 440 445

Ser Pro Glu Leu Ala Ala Ala Leu Asp Leu Trp Lys Glu Ile Lys Phe
450 455 460

Glu Phe Glu Thr Met Asp Lys Leu
465 470

<210> SEQ ID NO 3
<211> LENGTH: 111
<212> TYPE: PRT
<213> ORGANISM: Synechococcus PCC 6301
<220> FEATURE:
<221> NAME/KEY: DOMAIN
<222> LOCATION: (1)...(111)
<223> OTHER INFORMATION: Synechococcus rbcS

<400> SEQUENCE: 3

Met Ser Met Lys Thr Leu Pro Lys Glu Arg Arg Phe Glu Thr Phe Ser
1 5 10 15

Tyr Leu Pro Pro Leu Ser Asp Arg Gln Ile Ala Ala Gln Ile Glu Tyr
20 25 30

Met Ile Glu Gln Gly Phe His Pro Leu Ile Glu Phe Asn Glu His Ser
35 40 45

Asn Pro Glu Glu Phe Tyr Trp Thr Met Trp Lys Leu Pro Leu Phe Asp
50 55 60

Cys Lys Ser Pro Gln Gln Val Leu Asp Glu Val Arg Glu Cys Arg Ser
65 70 75 80

Glu Tyr Gly Asp Cys Tyr Ile Arg Val Ala Gly Phe Asp Asn Ile Lys
85 90 95

Gln Cys Gln Thr Val Ser Phe Ile Val His Arg Pro Gly Arg Tyr
100 105 110

<210> SEQ ID NO 4
<211> LENGTH: 1842
<212> TYPE: DNA
<213> ORGANISM: Artificial Sequence
<220> FEATURE:
<223> OTHER INFORMATION: RT24 rbcLS
<220> FEATURE:
<221> NAME/KEY: CDS
<222> LOCATION: (1)...(1419)
<223> OTHER INFORMATION: RT 24 rbcL
<220> FEATURE:
<221> NAME/KEY: CDS
<222> LOCATION: (1510)...(1842)
<223> OTHER INFORMATION: RT24 rbcS

<400> SEQUENCE: 4 atg ccc aag acg caa tct gcc gca ggc tat aag gcc ggg gtg aag gac 48
Met Pro Lys Thr Gln Ser Ala Ala Gly Tyr Lys Ala Gly Val Lys Asp
1 5 10 15 tac aaa ctc acc tat tac acc ccc gat tac acc ccc aaa gac act gac 96
Tyr Lys Leu Thr Tyr Tyr Thr Pro Asp Tyr Thr Pro Lys Asp Thr Asp
20 25 30 ctg ctg gcg gct ttc cgc ttc agc cct cag ccg ggt gtc cct gct gac 144
Leu Leu Ala Ala Phe Arg Phe Ser Pro Gln Pro Gly Val Pro Ala Asp
35 40 45 gaa gct ggt gcg gcg atc gcg gct gaa tct tcg acc ggt acc tgg acc 192
Glu Ala Gly Ala Ala Ile Ala Ala Glu Ser Ser Thr Gly Thr Trp Thr
50 55 60 acc gtg tgg acc gac ttg ctg acc gac atg gat cgg tac aaa ggc aag 240
Thr Val Trp Thr Asp Leu Leu Thr Asp Met Asp Arg Tyr Lys Gly Lys -continued

```
 65                  70                  75                  80

tgc tac cac atc gag ccg gtg caa ggc gaa gag aac tcc tac ttt gcg      288
Cys Tyr His Ile Glu Pro Val Gln Gly Glu Glu Asn Ser Tyr Phe Ala
                85                  90                  95

ttc atc gct tac ccg ctc gac ctg ttt gaa gaa ggg tcg gtc acc aac      336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc      432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac      480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc      720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aag gaa      768
Ala Pro Thr Cys Glu Glu Met Met Lys Arg Ala Glu Phe Ala Lys Glu
                245                 250                 255

atc ggc aca cca atc atc atg cat gac ttc ttg acg gct ggt ttc acc      816
Ile Gly Thr Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
        275                 280                 285

cac atc cac cgt gca atg cac gcg gtg atc gac cgt cag cgt aac cac      912
His Ile His Arg Ala Met His Ala Val Ile Asp Arg Gln Arg Asn His
    290                 295                 300

ggg att cac ttc cgt gtc ttg gcc aag tgt ttg cgt atg tct ggt ggt      960
Gly Ile His Phe Arg Val Leu Ala Lys Cys Leu Arg Met Ser Gly Gly
305                 310                 315                 320

gac cac ctc cac tcc ggc acc gtc gtc ggc aaa ctg gaa ggc gac aaa     1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa     1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg     1104
Ala Asp Arg Ser Arg Gly Val Phe Phe Thr Gln Asp Trp Ala Ser Met
        355                 360                 365

ccg ggc gtg ctg ccg gtt gct tcc ggc ggt atc cac gtg tgg cac atg     1152
Pro Gly Val Leu Pro Val Ala Ser Gly Gly Ile His Val Trp His Met
    370                 375                 380

ccc gcc ctg gtc gcc atc ttc ggt gac gac tcc gtg ctc cag ttc ggt     1200
```

-continued

```
Pro Ala Leu Val Ala Ile Phe Gly Asp Asp Ser Val Leu Gln Phe Gly
385                 390                 395                 400

ggc ggc acc ttg ggt cac ccc tgg ggt aat gct cct ggt gca acc gcg      1248
Gly Gly Thr Leu Gly His Pro Trp Gly Asn Ala Pro Gly Ala Thr Ala
                405                 410                 415

aac cgt gtt gcc ttg gaa gct tgc gtc caa gca cgt aac gaa ggt cgc      1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg      1344
Asp Leu Tyr Arg Glu Gly Gly Asp Ile Leu Arg Glu Ala Gly Lys Trp
        435                 440                 445

tcg cct gag ctg gcc atc gcc ctc gac ctc tgg aaa gag atc aag ttc      1392
Ser Pro Glu Leu Ala Ile Ala Leu Asp Leu Trp Lys Glu Ile Lys Phe
    450                 455                 460

gaa ttc gaa acg atg gac aag ctc taa ggagcctctg actatcgctg            1439
Glu Phe Glu Thr Met Asp Lys Leu  *
465                 470

ggggagtgag cgttgctgcg taaagctttc tccccagcct ttcgacttaa cctttcagga   1499

tttctgaatc atg agc atg aaa act ctg ccc aaa gag cgt cgt ttc gag      1548
           Met Ser Met Lys Thr Leu Pro Lys Glu Arg Arg Phe Glu
                   475                 480                 485

act ttc tcg tac ctg cct ccc ctc agc gat cgc caa atc gct gca caa      1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac      1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc      1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag      1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac      1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt ccc ggc      1836
Asn Ile Lys Gln Cys Gln Thr Val Ser Phe Ile Val His Arg Pro Gly
                570                 575                 580

cgc tac                                                              1842
Arg Tyr


<210> SEQ ID NO 5
<211> LENGTH: 472
<212> TYPE: PRT
<213> ORGANISM: Artificial Sequence
<220> FEATURE:
<223> OTHER INFORMATION: RT24 rbcL

<400> SEQUENCE: 5

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
```

-continued

```
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Ile Gly Thr Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Met Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Ala Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ile Ala Leu Asp Leu Trp Lys Glu Ile Lys Phe
    450                 455                 460

Glu Phe Glu Thr Met Asp Lys Leu
465                 470
```

<210> SEQ ID NO 6

-continued

```
<211> LENGTH: 111
<212> TYPE: PRT
<213> ORGANISM: Artificial Sequence
<220> FEATURE:
<223> OTHER INFORMATION: RT24 rbcS

<400> SEQUENCE: 6

Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110


<210> SEQ ID NO 7
<211> LENGTH: 1842
<212> TYPE: DNA
<213> ORGANISM: Artificial Sequence
<220> FEATURE:
<223> OTHER INFORMATION: RT 25 rbcLS
<220> FEATURE:
<221> NAME/KEY: CDS
<222> LOCATION: (1)...(1419)
<223> OTHER INFORMATION: RT 25 rbcL
<220> FEATURE:
<221> NAME/KEY: CDS
<222> LOCATION: (1510)...(1842)
<223> OTHER INFORMATION: RT25 rbcS

<400> SEQUENCE: 7

atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                  10                  15

tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
             20                  25                  30

ctg ctg gcg gct ttc cgc ttc agc cct cag ccg ggt gtc cct gct gac      144
Leu Leu Ala Ala Phe Arg Phe Ser Pro Gln Pro Gly Val Pro Ala Asp
         35                  40                  45

gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
     50                  55                  60

acc gtg tgg acc gac ttg ctg acc gac atg gat cgg tac aaa ggc aag      240
Thr Val Trp Thr Asp Leu Leu Thr Asp Met Asp Arg Tyr Lys Gly Lys
 65                  70                  75                  80

tgc tac cac atc gag ccg gtg caa ggc gaa gag aac tcc tac ttt gcg      288
Cys Tyr His Ile Glu Pro Val Gln Gly Glu Glu Asn Ser Tyr Phe Ala
                 85                  90                  95

ttc atc gct tac ccg ctc gac ctg ttt gaa gaa ggg tct gtc acc aac      336
Phe Ile Ala Tyr Pro Leu Asp Leu Phe Glu Glu Gly Ser Val Thr Asn
            100                 105                 110

ttg ctc acc tca ttg gtt ggt aac gta ttc ggt ttc aag gct ctt cgc      384
Leu Leu Thr Ser Leu Val Gly Asn Val Phe Gly Phe Lys Ala Leu Arg
        115                 120                 125
```

-continued

```
gca ctt cgt cta gaa gac atc cgc gta ccc atc gca tac ttg aag act      432
Ala Leu Arg Leu Glu Asp Ile Arg Val Pro Ile Ala Tyr Leu Lys Thr
    130                 135                 140

ttc caa ggt cct ccc cac ggt att caa gtc gag cgc gac ctg ctg aac      480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc      720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc acc      816
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
        275                 280                 285

cac att cac cgc gct atg cac gca gtt atc gac cgt cag cgt aac cac      912
His Ile His Arg Ala Met His Ala Val Ile Asp Arg Gln Arg Asn His
    290                 295                 300

ggg att cac ttc cgt gtc ttg gcc aag tgc ctg cgc ctc tcc ggt ggc      960
Gly Ile His Phe Arg Val Leu Ala Lys Cys Leu Arg Leu Ser Gly Gly
305                 310                 315                 320

gac cag ctc cac acc ggc acc gtg gtg ggc aag ctc gag ggt gac cgt     1008
Asp Gln Leu His Thr Gly Thr Val Val Gly Lys Leu Glu Gly Asp Arg
                325                 330                 335

cag acc acc ctg ggc ttc atc gac cag ctg cgc gaa tcc ttc atc ccc     1056
Gln Thr Thr Leu Gly Phe Ile Asp Gln Leu Arg Glu Ser Phe Ile Pro
            340                 345                 350

gaa gac cgc acc cgc ggc aac ttc ttc gat cag gac tgg ggt tcg atg     1104
Glu Asp Arg Thr Arg Gly Asn Phe Phe Asp Gln Asp Trp Gly Ser Met
        355                 360                 365

ccc ggc gtc ttc gcc gtg gcc tcc ggc ggc atc cac gtg tgg cac atg     1152
Pro Gly Val Phe Ala Val Ala Ser Gly Gly Ile His Val Trp His Met
    370                 375                 380

ccc gca ctg gtg gaa atc ttc ggt gat gac tcc gtg ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc     1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg     1344
Asp Leu Tyr Arg Glu Gly Gly Asp Ile Leu Arg Glu Ala Gly Lys Trp
        435                 440                 445
```

-continued

```
tcg cct gaa ctg gct gct gcc ctc gac ctc tgg aaa gag atc aag ttc      1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg           1439
Glu Phe Glu Thr Met Asp Lys Leu  *
465                 470

ggggagtgag cgttgctgcg taaagctttc tccccagcct ttcgacttaa cctttcagga   1499

tttctgaatc atg agc atg aaa act ctg ccc aaa gag cgt cgt ttc gag      1548
           Met Ser Met Lys Thr Leu Pro Lys Glu Arg Arg Phe Glu
                   475                 480                 485

act ttc tcg tac ctg cct ccc ctc agc gat cgc caa atc gct gca cag      1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac      1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc      1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag      1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac      1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt ccc ggc      1836
Asn Ile Lys Gln Cys Gln Thr Val Ser Phe Ile Val His Arg Pro Gly
                570                 575                 580

cgc tac                                                              1842
Arg Tyr


<210> SEQ ID NO 8
<211> LENGTH: 472
<212> TYPE: PRT
<213> ORGANISM: Artificial Sequence
<220> FEATURE:
<223> OTHER INFORMATION: RT25 rbcL

<400> SEQUENCE: 8

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Leu Leu Thr Ser Leu Val Gly Asn Val Phe Gly Phe Lys Ala Leu Arg
        115                 120                 125

Ala Leu Arg Leu Glu Asp Ile Arg Val Pro Ile Ala Tyr Leu Lys Thr
    130                 135                 140
```

-continued

```
Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp Gln Leu His Thr Gly Thr Val Val Gly Lys Leu Glu Gly Asp Arg
                325                 330                 335

Gln Thr Thr Leu Gly Phe Ile Asp Gln Leu Arg Glu Ser Phe Ile Pro
            340                 345                 350

Glu Asp Arg Thr Arg Gly Asn Phe Phe Asp Gln Asp Trp Gly Ser Met
        355                 360                 365

Pro Gly Val Phe Ala Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470
```

<210> SEQ ID NO 9
<211> LENGTH: 111
<212> TYPE: PRT
<213> ORGANISM: Artificial Sequence
<220> FEATURE:
<223> OTHER INFORMATION: RT25 rbcS

<400> SEQUENCE: 9

```
Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30
```

-continued

```
Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110


<210> SEQ ID NO 10
<211> LENGTH: 1865
<212> TYPE: DNA
<213> ORGANISM: Artificial Sequence
<220> FEATURE:
<223> OTHER INFORMATION: RT28 rbcLS
<220> FEATURE:
<221> NAME/KEY: CDS
<222> LOCATION: (1)...(1419)
<223> OTHER INFORMATION: RT28 rbcL
<220> FEATURE:
<221> NAME/KEY: CDS
<222> LOCATION: (1510)...(1845)
<223> OTHER INFORMATION: RT28 rbcS

<400> SEQUENCE: 10

atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                  10                  15

tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
            20                  25                  30

ctg ctg gcg gct ttc cgc ttc agc cct cag ccg ggt gtc cct gct gac      144
Leu Leu Ala Ala Phe Arg Phe Ser Pro Gln Pro Gly Val Pro Ala Asp
        35                  40                  45

gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
     50                  55                  60

acc gtg tgg acc gac ttg ctg acc gac atg gat cgg tac aaa ggc aag      240
Thr Val Trp Thr Asp Leu Leu Thr Asp Met Asp Arg Tyr Lys Gly Lys
 65                  70                  75                  80

tgc tac cac gtc gag ccg gtg caa ggc gaa gag aac tcc tac ttt gcg      288
Cys Tyr His Val Glu Pro Val Gln Gly Glu Glu Asn Ser Tyr Phe Ala
                85                  90                  95

ttc atc gct tac ccg ctc gac ctg ttt gaa gaa ggg tcg gtc acc aac      336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc      432
Ser Leu Arg Leu Glu Asp Ile Arg Phe Pro Val Ala Leu Val Lys Thr
    130                 135                 140

ttc caa ggt cct cct cac ggt att caa gtt gaa cgc gac aag ttg aac      480
Phe Gln Gly Pro Pro His Gly Ile Gln Val Glu Arg Asp Lys Leu Asn
145                 150                 155                 160

aag tac ggt cgt cct ctc ttg ggt tgt acc att aag ccc aaa cta ggc      528
Lys Tyr Gly Arg Pro Leu Leu Gly Cys Thr Ile Lys Pro Lys Leu Gly
                165                 170                 175

cta tct gct aag aac tac ggt cgt gca gta tac gaa tgt cta cgc ggt      576
Leu Ser Ala Lys Asn Tyr Gly Arg Ala Val Tyr Glu Cys Leu Arg Gly
```

-continued

```
        180                 185                 190

ggt ttg gac ttc acc aaa gac gac gaa aac atc aac tcg cag ccg ttc       624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa       672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc       720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aaa gaa       768
Ala Pro Thr Cys Glu Glu Met Met Lys Arg Ala Glu Phe Ala Lys Glu
            245                 250                 255

ctc ggc atg ccg atc atc atg cat gac ttc ttg acg gct ggt ttc acc       816
Leu Gly Met Pro Ile Ile Met His Asp Phe Leu Thr Ala Gly Phe Thr
        260                 265                 270

gcc aac acc acc ttg gca aaa tgg tgc cgc gac aac ggc gtc ctg ctg       864
Ala Asn Thr Thr Leu Ala Lys Trp Cys Arg Asp Asn Gly Val Leu Leu
        275                 280                 285

cac atc cac cgt gca atg cac gcg gtg atc gac cgt cag cgt aac cac       912
His Ile His Arg Ala Met His Ala Val Ile Asp Arg Gln Arg Asn His
    290                 295                 300

ggg att cac ttc cgc gtt ttg gct aag tgt ctg cgt atg tct ggt ggt       960
Gly Ile His Phe Arg Val Leu Ala Lys Cys Leu Arg Met Ser Gly Gly
305                 310                 315                 320

gat cac ctc cac tct ggc acc gtc gtc ggc aaa ctg gaa ggc gac aaa      1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa      1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg      1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg      1152
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt      1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca atc gcg      1248
Gly Gly Thr Leu Gly His Pro Trp Gly Asn Ala Pro Gly Ala Ile Ala
                405                 410                 415

aac cgt gtt gcc ttg gaa gct tgc gtc caa gct cgg aac gaa ggt cgc      1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg      1344
Asp Leu Tyr Arg Glu Gly Gly Asp Ile Leu Arg Glu Ala Gly Lys Trp
        435                 440                 445

tcg cct gaa ctg gct gct gcc ctc gac ctc tgg aaa gag atc aag ttc      1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg            1439
Glu Phe Glu Thr Met Asp Lys Leu  *
465                 470

ggggagtgag cgttgctgcg taaagctttc tccccagcct ttcgacttaa cctttcagga    1499

tttctgaatc atg agc atg aaa act ctg ccc aaa gag cgt cgt ttc gag      1548
            Met Ser Met Lys Thr Leu Pro Lys Glu Arg Arg Phe Glu
                    475                 480                 485
```

-continued

```
act ttc tcg tac ctg cct ccc ctc agc aat cgc caa atc gct gca caa      1596
Thr Phe Ser Tyr Leu Pro Pro Leu Ser Asn Arg Gln Ile Ala Ala Gln
                490                 495                 500

atc gag tac atg atc gag caa ggc ttc cac ccc ttg atc gag ttc aac      1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc      1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag      1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac      1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt ccc ggc      1836
Asn Ile Lys Gln Cys Gln Thr Val Ser Phe Ile Val His Arg Pro Gly
                570                 575                 580

cgc tac taa tgaggccaaa ctggccatgc                                    1865
Arg Tyr  *


<210> SEQ ID NO 11
<211> LENGTH: 472
<212> TYPE: PRT
<213> ORGANISM: Artificial Sequence
<220> FEATURE:
<223> OTHER INFORMATION: RT28 rbcL

<400> SEQUENCE: 11

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Val Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Lys Leu Asn
145                 150                 155                 160

Lys Tyr Gly Arg Pro Leu Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220
```

-continued

Ser Gln Ala Glu Thr Gly Glu Ile Lys Gly His Tyr Leu Asn Val Thr
225 230 235 240

Ala Pro Thr Cys Glu Glu Met Met Lys Arg Ala Glu Phe Ala Lys Glu
245 250 255

Leu Gly Met Pro Ile Ile Met His Asp Phe Leu Thr Ala Gly Phe Thr
260 265 270

Ala Asn Thr Thr Leu Ala Lys Trp Cys Arg Asp Asn Gly Val Leu Leu
275 280 285

His Ile His Arg Ala Met His Ala Val Ile Asp Arg Gln Arg Asn His
290 295 300

Gly Ile His Phe Arg Val Leu Ala Lys Cys Leu Arg Met Ser Gly Gly
305 310 315 320

Asp His Leu His Ser Gly Thr Val Val Gly Lys Leu Glu Gly Asp Lys
325 330 335

Ala Ser Thr Leu Gly Phe Val Asp Leu Met Arg Glu Asp His Ile Glu
340 345 350

Ala Asp Arg Ser Arg Gly Val Phe Phe Thr Gln Asp Trp Ala Ser Met
355 360 365

Pro Gly Val Leu Pro Val Ala Ser Gly Gly Ile His Val Trp His Met
370 375 380

Pro Ala Leu Val Glu Ile Phe Gly Asp Asp Ser Val Leu Gln Phe Gly
385 390 395 400

Gly Gly Thr Leu Gly His Pro Trp Gly Asn Ala Pro Gly Ala Ile Ala
405 410 415

Asn Arg Val Ala Leu Glu Ala Cys Val Gln Ala Arg Asn Glu Gly Arg
420 425 430

Asp Leu Tyr Arg Glu Gly Gly Asp Ile Leu Arg Glu Ala Gly Lys Trp
435 440 445

Ser Pro Glu Leu Ala Ala Ala Leu Asp Leu Trp Lys Glu Ile Lys Phe
450 455 460

Glu Phe Glu Thr Met Asp Lys Leu
465 470

<210> SEQ ID NO 12
<211> LENGTH: 111
<212> TYPE: PRT
<213> ORGANISM: Artificial Sequence
<220> FEATURE:
<223> OTHER INFORMATION: RT28 rbcS

<400> SEQUENCE: 12

Met Ser Met Lys Thr Leu Pro Lys Glu Arg Arg Phe Glu Thr Phe Ser
1 5 10 15

Tyr Leu Pro Pro Leu Ser Asn Arg Gln Ile Ala Ala Gln Ile Glu Tyr
20 25 30

Met Ile Glu Gln Gly Phe His Pro Leu Ile Glu Phe Asn Glu His Ser
35 40 45

Asn Pro Glu Glu Phe Tyr Trp Thr Met Trp Lys Leu Pro Leu Phe Asp
50 55 60

Cys Lys Ser Pro Gln Gln Val Leu Asp Glu Val Arg Glu Cys Arg Ser
65 70 75 80

Glu Tyr Gly Asp Cys Tyr Ile Arg Val Ala Gly Phe Asp Asn Ile Lys
85 90 95

Gln Cys Gln Thr Val Ser Phe Ile Val His Arg Pro Gly Arg Tyr
100 105 110

-continued

<210> SEQ ID NO 13
<211> LENGTH: 1842
<212> TYPE: DNA
<213> ORGANISM: Artificial Sequence
<220> FEATURE:
<223> OTHER INFORMATION: RT30 rbcLS
<220> FEATURE:
<221> NAME/KEY: CDS
<222> LOCATION: (1)...(1419)
<223> OTHER INFORMATION: RT30 rbcL
<220> FEATURE:
<221> NAME/KEY: CDS
<222> LOCATION: (1510)...(1842)
<223> OTHER INFORMATION: RT30 rbcS

<400> SEQUENCE: 13

```
atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                  10                  15

tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
            20                  25                  30

ctg ctg gcg gct ttc cgc ttc agc cct cag ccg ggt gtc cct gct gac      144
Leu Leu Ala Ala Phe Arg Phe Ser Pro Gln Pro Gly Val Pro Ala Asp
        35                  40                  45

gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
    50                  55                  60

acc gtg tgg acc gac ttg ctg acc gac atg gat cgg tac aaa ggc aag      240
Thr Val Trp Thr Asp Leu Leu Thr Asp Met Asp Arg Tyr Lys Gly Lys
 65                 70                  75                  80

tgc tac cac atc gag ccg gtg caa ggc gaa gag gac tcc tac ttt gcg      288
Cys Tyr His Ile Glu Pro Val Gln Gly Glu Glu Asp Ser Tyr Phe Ala
                85                  90                  95

ttc atc gct tac ccg ctc gac ctg ttt gaa gaa ggg tcg gtc acc aac      336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc      432
Ser Leu Arg Leu Glu Asp Ile Arg Phe Pro Val Ala Leu Val Lys Thr
    130                 135                 140

ttc caa ggt cct ccc cac ggt atc caa ggc gag cgc gac ctg ctg aac      480
Phe Gln Gly Pro Pro His Gly Ile Gln Gly Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc      720
Ser Gln Ala Glu Thr Gly Glu Ile Lys Gly His Tyr Leu Asn Val Thr
225                 230                 235                 240
```

-continued

```
gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc acc      816
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
        275                 280                 285

cac atc cac cgt gca atg cac gcg gtg atc gac cgt cag cgt aac cac      912
His Ile His Arg Ala Met His Ala Val Ile Asp Arg Gln Arg Asn His
    290                 295                 300

ggg att cac ttc cgt gtc ttg gcc aag tgt ttg cgt ctg tcc ggt ggt      960
Gly Ile His Phe Arg Val Leu Ala Lys Cys Leu Arg Leu Ser Gly Gly
305                 310                 315                 320

gac cac ctc cac tcc ggc acc gtc gtc ggc aaa ctg gaa ggc gac aaa     1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa     1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg     1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg     1152
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc     1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg     1344
Asp Leu Tyr Arg Glu Gly Gly Asp Ile Leu Arg Glu Ala Gly Lys Trp
        435                 440                 445

tcg cct gaa ctg gct gct gcc ctc gac ctc tgg aaa gag atc aag ttc     1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg           1439
Glu Phe Glu Thr Met Asp Lys Leu  *
465                 470

ggggagtgag cgttgctgcg taaagccttc tccccagcct ttcgacttaa cctttcagga   1499

tttctgaatc atg agc atg aaa act ctg ccc aaa gag cgt cgt ttc gag      1548
           Met Ser Met Lys Thr Leu Pro Lys Glu Arg Arg Phe Glu
                   475                 480                 485

act ttc tcg tac ctg cct ccc ctc agc gat cgc caa atc gct gca caa     1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac     1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc     1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag     1740
```

-continued

```
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac      1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt ccc ggc      1836
Asn Ile Lys Gln Cys Gln Thr Val Ser Phe Ile Val His Arg Pro Gly
                570                 575                 580

cgc tac                                                              1842
Arg Tyr


<210> SEQ ID NO 14
<211> LENGTH: 472
<212> TYPE: PRT
<213> ORGANISM: Artificial Sequence
<220> FEATURE:
<223> OTHER INFORMATION: RT30 rbcL

<400> SEQUENCE: 14

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asp Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Gly Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
```

-continued

```
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470


<210> SEQ ID NO 15
<211> LENGTH: 111
<212> TYPE: PRT
<213> ORGANISM: Artificial Sequence
<220> FEATURE:
<223> OTHER INFORMATION: RT30 rbcS

<400> SEQUENCE: 15

Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110


<210> SEQ ID NO 16
<211> LENGTH: 1845
<212> TYPE: DNA
<213> ORGANISM: Artificial Sequence
<220> FEATURE:
<223> OTHER INFORMATION: RT106 rbcLS
<220> FEATURE:
<221> NAME/KEY: CDS
<222> LOCATION: (1)...(1419)
<223> OTHER INFORMATION: RT106 rbcL
<220> FEATURE:
<221> NAME/KEY: CDS
```

-continued

```
<222> LOCATION: (1510)...(1845)
<223> OTHER INFORMATION: RT106 rbcS

<400> SEQUENCE: 16

atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                   10                  15

tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
             20                  25                  30

ctg ctg gcg gct ttc cgc ttc agc cct cag ccg ggt gtc cct gct gac      144
Leu Leu Ala Ala Phe Arg Phe Ser Pro Gln Pro Gly Val Pro Ala Asp
         35                  40                  45

gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
     50                  55                  60

acc gtg tgg acc gac ttg ctg acc gac atg gat cgg tac aaa ggc aag      240
Thr Val Trp Thr Asp Leu Leu Thr Asp Met Asp Arg Tyr Lys Gly Lys
 65                  70                  75                  80

tgc tac cac atc gag ccg gtg caa ggc gaa gag aac tcc tac ttt gcg      288
Cys Tyr His Ile Glu Pro Val Gln Gly Glu Glu Asn Ser Tyr Phe Ala
                 85                  90                  95

ttc atc gct tac ccg ctc gac ctg ttt gaa gaa ggg tcg gtc acc aac      336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc      432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac      480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc      720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc acc      816
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
        275                 280                 285

cac atc cac cgt gca atg cac gcg gtg atc gac cgt cag cgt aac cac      912
His Ile His Arg Ala Met His Ala Val Ile Asp Arg Gln Arg Asn His
```

-continued

```
    290                 295                 300

ggg att cac ttc cgt gtc ttg gcc aag tgt ttg cgt ctg tcc ggt ggt      960
Gly Ile His Phe Arg Val Leu Ala Lys Cys Leu Arg Leu Ser Gly Gly
305                 310                 315                 320

gac cac ctc cac tcc ggc acc gtc gtc ggc aaa ctg gaa ggc gac aaa     1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa     1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg     1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg     1152
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc     1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg     1344
Asp Leu Tyr Arg Glu Gly Gly Asp Ile Leu Arg Glu Ala Gly Lys Trp
        435                 440                 445

tcg cct gaa ctg gct gct gcc ctc gac ctc tgg aaa gag atc aag ttc     1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg           1439
Glu Phe Glu Thr Met Asp Lys Leu  *
465                 470

ggggagtgag cgttgctgcg taaagctttc tccccagcct ttcgacttaa cctttcagga   1499

tttctgaatc atg agc atg aaa act ctg ccc aaa gag cgt cgt ttc gag      1548
            Met Ser Met Lys Thr Leu Pro Lys Glu Arg Arg Phe Glu
                    475                 480                 485

act ttc tcg tac ctg cct ccc ctc agc gat cgc caa atc gct gca caa     1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac     1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc     1692
Glu His Ser Asn Pro Glu Glu Phe Tyr Trp Thr Met Trp Lys Leu Pro
        520                 525                 530

ctg ttt gac tgc aag ggc cct cag caa gtc ctc gat gaa gtg cgt gag     1740
Leu Phe Asp Cys Lys Gly Pro Gln Gln Val Leu Asp Glu Val Arg Glu
    535                 540                 545

tgc cgc agc gaa tac ggt gat tgc tac atc cgt gtc gct ggc ttc gac     1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt ccc ggc     1836
Asn Ile Lys Gln Cys Gln Thr Val Ser Phe Ile Val His Arg Pro Gly
                570                 575                 580

cgc tac taa                                                         1845
Arg Tyr  *
```

-continued

<210> SEQ ID NO 17
<211> LENGTH: 472
<212> TYPE: PRT
<213> ORGANISM: Artificial Sequence
<220> FEATURE:
<223> OTHER INFORMATION: RT106 rbcL

<400> SEQUENCE: 17

```
Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365
```

-continued

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470

<210> SEQ ID NO 18
<211> LENGTH: 111
<212> TYPE: PRT
<213> ORGANISM: Artificial Sequence
<220> FEATURE:
<223> OTHER INFORMATION: RT106 rbcS

<400> SEQUENCE: 18

Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Gly Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110

<210> SEQ ID NO 19
<211> LENGTH: 1845
<212> TYPE: DNA
<213> ORGANISM: Artificial Sequence
<220> FEATURE:
<223> OTHER INFORMATION: RT108 rbcLS
<220> FEATURE:
<221> NAME/KEY: CDS
<222> LOCATION: (1)...(1419)
<223> OTHER INFORMATION: RT108 rbcL
<220> FEATURE:
<221> NAME/KEY: CDS
<222> LOCATION: (1510)...(1845)
<223> OTHER INFORMATION: RT108 rbcS

<400> SEQUENCE: 19 atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                  10                  15 tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
            20                  25                  30 ctg ctg gcg gct ttc cgc ttc agc cct cag ccg ggt gtc cct gct gac      144

-continued

```
Leu Leu Ala Ala Phe Arg Phe Ser Pro Gln Pro Gly Val Pro Ala Asp
        35                  40                  45

gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
    50                  55                  60

acc gtg tgg acc gac ttg ctg acc gac atg gat cgg tac aaa ggc aag      240
Thr Val Trp Thr Asp Leu Leu Thr Asp Met Asp Arg Tyr Lys Gly Lys
65                  70                  75                  80

tgc tac cac atc gag ccg gtg caa ggc gaa gag aac tcc tac ttt gcg      288
Cys Tyr His Ile Glu Pro Val Gln Gly Glu Glu Asn Ser Tyr Phe Ala
                85                  90                  95

ttc atc gct tac ccg ctc gac ctg ttt gaa gaa ggg tcg gtc acc aac      336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc      432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac      480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc      720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc acg ccg atc atc atg cat gac ttc ttg acg gct ggt ttc acc      816
Leu Gly Thr Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
        275                 280                 285

cac atc cac cgt gca atg cac gcg gtg atc gac cgt cag cgt aac cac      912
His Ile His Arg Ala Met His Ala Val Ile Asp Arg Gln Arg Asn His
    290                 295                 300

ggg att cac ttc cgt gtc ttg gcc aag tgt ttg cgt ctg tcc ggt ggt      960
Gly Ile His Phe Arg Val Leu Ala Lys Cys Leu Arg Leu Ser Gly Gly
305                 310                 315                 320

gac cac ctc cac tcc ggc acc gtc gtc ggc aaa ctg gaa ggc gac aaa     1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa     1056
Ala Ser Thr Leu Gly Phe Val Asp Leu Met Arg Glu Asp His Ile Glu
            340                 345                 350
```

-continued

```
gct gac cgc agc cgt ggg gtc ttc ttc acc caa gat tgg gcg tcg atg     1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg     1152
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc     1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg     1344
Asp Leu Tyr Arg Glu Gly Gly Asp Ile Leu Arg Glu Ala Gly Lys Trp
        435                 440                 445

tcg cct gaa ctg gct gct gcc ctc gac ctc tgg aaa gag atc aag ttc     1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg           1439
Glu Phe Glu Thr Met Asp Lys Leu  *
465                 470

ggggagtgag cgttgctgcg taaagctttc tccccagcct ttcgacttaa cctttcagga   1499

tttctgaatc atg agc atg aaa act ctg ccc aaa gag cgt cgt ttc gag     1548
            Met Ser Met Lys Thr Leu Pro Lys Glu Arg Arg Phe Glu
                    475                 480                 485

act ttc tcg tac ctg cct ccc ctc agc gat cgc caa atc gct gca caa     1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac     1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc     1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag     1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac     1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt ccc ggc     1836
Asn Ile Lys Gln Cys Gln Thr Val Ser Phe Ile Val His Arg Pro Gly
                570                 575                 580

cgc tac taa                                                         1845
Arg Tyr  *


<210> SEQ ID NO 20
<211> LENGTH: 472
<212> TYPE: PRT
<213> ORGANISM: Artificial Sequence
<220> FEATURE:
<223> OTHER INFORMATION: RT108 rbcL

<400> SEQUENCE: 20

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
```

-continued

```
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Thr Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445
```

-continued

Ser Pro Glu Leu Ala Ala Ala Leu Asp Leu Trp Lys Glu Ile Lys Phe
    450                 455                 460

Glu Phe Glu Thr Met Asp Lys Leu
465                 470

<210> SEQ ID NO 21
<211> LENGTH: 111
<212> TYPE: PRT
<213> ORGANISM: Artificial Sequence
<220> FEATURE:
<223> OTHER INFORMATION: RT108 rbcS

<400> SEQUENCE: 21

Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110

<210> SEQ ID NO 22
<211> LENGTH: 1845
<212> TYPE: DNA
<213> ORGANISM: Artificial Sequence
<220> FEATURE:
<223> OTHER INFORMATION: RT111 rbcLS
<220> FEATURE:
<221> NAME/KEY: CDS
<222> LOCATION: (1)...(1419)
<223> OTHER INFORMATION: RT111 rbcL
<220> FEATURE:
<221> NAME/KEY: CDS
<222> LOCATION: (1510)...(1845)
<223> OTHER INFORMATION: RT111 rbcS

<400> SEQUENCE: 22 atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                  10                  15 tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
            20                  25                  30 ctg ctg gcg gct ttc cgc ttc agc cct cag ccg ggt gtc cct gct gac      144
Leu Leu Ala Ala Phe Arg Phe Ser Pro Gln Pro Gly Val Pro Ala Asp
        35                  40                  45 gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
    50                  55                  60 acc gtg tgg acc gac ttg ctg acc gac atg gat cgg tac aaa ggc aag      240
Thr Val Trp Thr Asp Leu Leu Thr Asp Met Asp Arg Tyr Lys Gly Lys
 65                 70                  75                  80 tgc tac cac atc gag ccg gtg caa ggc gaa gag aac tcc tac ttt gcg      288
Cys Tyr His Ile Glu Pro Val Gln Gly Glu Glu Asn Ser Tyr Phe Ala
                85                  90                  95

-continued

```
ttc atc gct tac ccg ctc gac ctg ttt gaa gaa ggg tcg gtc acc aac      336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc      432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac      480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc      720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc acc      816
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
        275                 280                 285

cac atc cac cgt gca atg cac gcg gtg atc gac cgt cag cgt aac cac      912
His Ile His Arg Ala Met His Ala Val Ile Asp Arg Gln Arg Asn His
    290                 295                 300

ggg att cac ttc cgt gtc ttg gcc aag tgt ttg cgt ctg tcc ggt ggt      960
Gly Ile His Phe Arg Val Leu Ala Lys Cys Leu Arg Leu Ser Gly Gly
305                 310                 315                 320

gac cac ctc cac tcc ggc acc gtc gtc ggc aaa ctg gaa ggc gac aaa     1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa     1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg     1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg     1152
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
```

-continued

```
            405                 410                 415

aac cgt gtt gcc ttg gaa gct tgc gtc caa gct cgg aac gaa ggt cgc      1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg      1344
Asp Leu Tyr Arg Glu Gly Gly Asp Ile Leu Arg Glu Ala Gly Lys Trp
        435                 440                 445

tcg cct gaa ctg gct gct gcc ctc gac ctc tgg aaa gag atc aag ttc      1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg           1439
Glu Phe Glu Thr Met Asp Lys Leu  *
465                 470

ggggagtgag cgttgctgcg taaagctttc tccccagcct ttcgacttaa cctttcagga   1499

tttctgaatc atg agc atg aaa act ctg ccc aaa gag cgt cgt ttc gag      1548
           Met Ser Met Lys Thr Leu Pro Lys Glu Arg Arg Phe Glu
                   475                 480                 485

act ttc tcg tac ctg cct ccc ctc agc gat cgc caa atc gct gca caa      1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac      1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc      1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag      1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac      1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt tcc ggc      1836
Asn Ile Lys Gln Cys Gln Thr Val Ser Phe Ile Val His Arg Ser Gly
                570                 575                 580

cgc tac taa                                                          1845
Arg Tyr  *


<210> SEQ ID NO 23
<211> LENGTH: 472
<212> TYPE: PRT
<213> ORGANISM: Artificial Sequence
<220> FEATURE:
<223> OTHER INFORMATION: RT111 rbcL

<400> SEQUENCE: 23

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95
```

-continued

```
Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470
```

<210> SEQ ID NO 24
<211> LENGTH: 111
<212> TYPE: PRT
<213> ORGANISM: Artificial Sequence
<220> FEATURE:
<223> OTHER INFORMATION: RT111 rbcS

<400> SEQUENCE: 24

Met Ser Met Lys Thr Leu Pro Lys Glu Arg Arg Phe Glu Thr Phe Ser
1 5 10 15

Tyr Leu Pro Pro Leu Ser Asp Arg Gln Ile Ala Ala Gln Ile Glu Tyr
20 25 30

Met Ile Glu Gln Gly Phe His Pro Leu Ile Glu Phe Asn Glu His Ser
35 40 45

Asn Pro Glu Glu Phe Tyr Trp Thr Met Trp Lys Leu Pro Leu Phe Asp
50 55 60

Cys Lys Ser Pro Gln Gln Val Leu Asp Glu Val Arg Glu Cys Arg Ser
65 70 75 80

Glu Tyr Gly Asp Cys Tyr Ile Arg Val Ala Gly Phe Asp Asn Ile Lys
85 90 95

Gln Cys Gln Thr Val Ser Phe Ile Val His Arg Ser Gly Arg Tyr
100 105 110

<210> SEQ ID NO 25
<211> LENGTH: 1845
<212> TYPE: DNA
<213> ORGANISM: Artificial Sequence
<220> FEATURE:
<223> OTHER INFORMATION: RT113 rbcLS
<220> FEATURE:
<221> NAME/KEY: CDS
<222> LOCATION: (1)...(1419)
<223> OTHER INFORMATION: RT113 rbcL
<220> FEATURE:
<221> NAME/KEY: CDS
<222> LOCATION: (1510)...(1845)
<223> OTHER INFORMATION: RT113 rbcS

<400> SEQUENCE: 25 atg ccc aag acg caa tct gcc gca ggc tat aag gcc ggg gtg aag gac 48
Met Pro Lys Thr Gln Ser Ala Ala Gly Tyr Lys Ala Gly Val Lys Asp
1 5 10 15 tac aaa ctc acc tat tac acc ccc gat tac acc ccc aaa gac act gac 96
Tyr Lys Leu Thr Tyr Tyr Thr Pro Asp Tyr Thr Pro Lys Asp Thr Asp
20 25 30 ctg ctg gcg gct ttc cgc ttc agc cct cag ccg ggt gtc cct gct gac 144
Leu Leu Ala Ala Phe Arg Phe Ser Pro Gln Pro Gly Val Pro Ala Asp
35 40 45 gaa gct ggt gcg gcg atc gcg gct gaa tct tcg acc ggt acc tgg acc 192
Glu Ala Gly Ala Ala Ile Ala Ala Glu Ser Ser Thr Gly Thr Trp Thr
50 55 60 acc gtg tgg acc gac ttg ctg acc gac atg gat cgg tac aaa ggc aag 240
Thr Val Trp Thr Asp Leu Leu Thr Asp Met Asp Arg Tyr Lys Gly Lys
65 70 75 80 tgc tac cac atc gag ccg gtg caa ggc gaa gag aac tcc tac ttt gcg 288
Cys Tyr His Ile Glu Pro Val Gln Gly Glu Glu Asn Ser Tyr Phe Ala
85 90 95 ttc atc gct tac ccg ctc gac ctg ttt gaa gaa ggg tcg gtc acc aac 336
Phe Ile Ala Tyr Pro Leu Asp Leu Phe Glu Glu Gly Ser Val Thr Asn
100 105 110 atc ctg acc tcg atc gtc ggt aac gtg ttt ggc ttc aaa gct atc cgt 384
Ile Leu Thr Ser Ile Val Gly Asn Val Phe Gly Phe Lys Ala Ile Arg
115 120 125 tcg ctg cgt ctg gaa gac atc cgc ttc ccc gtc gcc ttg gtc aaa acc 432
Ser Leu Arg Leu Glu Asp Ile Arg Phe Pro Val Ala Leu Val Lys Thr
130 135 140 ttc caa ggt cct ccc cac ggt atc caa gtc gag cgc gac ctg ctg aac 480

-continued

```
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc      720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc acc      816
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
        275                 280                 285

cac atc cac cgt gca atg cac gcg gtg atc gac cgt cag cgt aac cac      912
His Ile His Arg Ala Met His Ala Val Ile Asp Arg Gln Arg Asn His
    290                 295                 300

ggg att cac ttc cgt gtc ttg gcc aag tgt ttg cgt ctg tcc ggt ggt      960
Gly Ile His Phe Arg Val Leu Ala Lys Cys Leu Arg Leu Ser Gly Gly
305                 310                 315                 320

gac cac ctc cac tcc ggc acc gtc gtc ggc aaa ctg gaa ggc gac aaa     1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa     1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg     1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg     1152
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc     1296
Asn Arg Val Ala Leu Glu Ala Cys Val Gln Ala Arg Asn Glu Gly Arg
            420                 425                 430

gac ctc tac cgt gag ggc ggc gac atc ctt cgt gaa gct ggc aag tgg     1344
Asp Leu Tyr Arg Glu Gly Gly Asp Ile Leu Arg Glu Ala Gly Lys Trp
        435                 440                 445

tcg cct gaa ctg gct gct gcc ctc gac ctc tgg aaa gag atc aag ttc     1392
Ser Pro Glu Leu Ala Ala Ala Leu Asp Leu Trp Lys Glu Ile Lys Phe
    450                 455                 460
```

-continued

```
gaa ttc gaa acg atg gac aag ctc taa ggagcctctg actatcgctg          1439
Glu Phe Glu Thr Met Asp Lys Leu  *
465                 470

ggggagtgag cgttgctgcg taaagctttc tccccagcct ttcgacttaa cctttcagga   1499

tttctgaatc atg agc atg aaa act ctg ccc aaa gag cgt cgt ttc gag      1548
           Met Ser Met Lys Thr Leu Pro Lys Glu Arg Arg Phe Glu
                   475                 480                 485

act ttc tcg tac ctg cct ccc ctc agc gat cgc caa atc gct gca caa     1596
Thr Phe Ser Tyr Leu Pro Pro Leu Ser Asp Arg Gln Ile Ala Ala Gln
               490                 495                 500

atc gag tac atg atc gag caa ggc ttc cac ccc ttg atc gag ttc aac     1644
Ile Glu Tyr Met Ile Glu Gln Gly Phe His Pro Leu Ile Glu Phe Asn
           505                 510                 515

gag cac tcg aat ccg gaa gag ttc tac tgg acg atg tgg aag ctc ccc     1692
Glu His Ser Asn Pro Glu Glu Phe Tyr Trp Thr Met Trp Lys Leu Pro
       520                 525                 530

ctg ttt gac tgc aat agc cct cag caa gtc ctc gat gaa gtg cgt gag     1740
Leu Phe Asp Cys Asn Ser Pro Gln Gln Val Leu Asp Glu Val Arg Glu
    535                 540                 545

tgc cgc agc gaa tac ggt gat tgc tac atc cgt gtc gct ggc ttc gac     1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt ccc ggc     1836
Asn Ile Lys Gln Cys Gln Thr Val Ser Phe Ile Val His Arg Pro Gly
               570                 575                 580

cgc tac taa                                                         1845
Arg Tyr  *
```

<210> SEQ ID NO 26
<211> LENGTH: 472
<212> TYPE: PRT
<213> ORGANISM: Artificial Sequence
<220> FEATURE:
<223> OTHER INFORMATION: RT113 rbcL

<400> SEQUENCE: 26

```
Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175
```

Leu Ser Ala Lys Asn Tyr Gly Arg Ala Val Tyr Glu Cys Leu Arg Gly
180 185 190

Gly Leu Asp Phe Thr Lys Asp Asp Glu Asn Ile Asn Ser Gln Pro Phe
195 200 205

Gln Arg Trp Arg Asp Arg Phe Leu Phe Val Ala Asp Ala Ile His Lys
210 215 220

Ser Gln Ala Glu Thr Gly Glu Ile Lys Gly His Tyr Leu Asn Val Thr
225 230 235 240

Ala Pro Thr Cys Glu Glu Met Met Lys Arg Ala Glu Phe Ala Lys Glu
245 250 255

Leu Gly Met Pro Ile Ile Met His Asp Phe Leu Thr Ala Gly Phe Thr
260 265 270

Ala Asn Thr Thr Leu Ala Lys Trp Cys Arg Asp Asn Gly Val Leu Leu
275 280 285

His Ile His Arg Ala Met His Ala Val Ile Asp Arg Gln Arg Asn His
290 295 300

Gly Ile His Phe Arg Val Leu Ala Lys Cys Leu Arg Leu Ser Gly Gly
305 310 315 320

Asp His Leu His Ser Gly Thr Val Val Gly Lys Leu Glu Gly Asp Lys
325 330 335

Ala Ser Thr Leu Gly Phe Val Asp Leu Met Arg Glu Asp His Ile Glu
340 345 350

Ala Asp Arg Ser Arg Gly Val Phe Phe Thr Gln Asp Trp Ala Ser Met
355 360 365

Pro Gly Val Leu Pro Val Ala Ser Gly Gly Ile His Val Trp His Met
370 375 380

Pro Ala Leu Val Glu Ile Phe Gly Asp Asp Ser Val Leu Gln Phe Gly
385 390 395 400

Gly Gly Thr Leu Gly His Pro Trp Gly Asn Ala Pro Gly Ala Thr Ala
405 410 415

Asn Arg Val Ala Leu Glu Ala Cys Val Gln Ala Arg Asn Glu Gly Arg
420 425 430

Asp Leu Tyr Arg Glu Gly Gly Asp Ile Leu Arg Glu Ala Gly Lys Trp
435 440 445

Ser Pro Glu Leu Ala Ala Ala Leu Asp Leu Trp Lys Glu Ile Lys Phe
450 455 460

Glu Phe Glu Thr Met Asp Lys Leu
465 470

<210> SEQ ID NO 27
<211> LENGTH: 111
<212> TYPE: PRT
<213> ORGANISM: Artificial Sequence
<220> FEATURE:
<223> OTHER INFORMATION: RT113 rbcS

<400> SEQUENCE: 27

Met Ser Met Lys Thr Leu Pro Lys Glu Arg Arg Phe Glu Thr Phe Ser
1 5 10 15

Tyr Leu Pro Pro Leu Ser Asp Arg Gln Ile Ala Ala Gln Ile Glu Tyr
20 25 30

Met Ile Glu Gln Gly Phe His Pro Leu Ile Glu Phe Asn Glu His Ser
35 40 45

Asn Pro Glu Glu Phe Tyr Trp Thr Met Trp Lys Leu Pro Leu Phe Asp
50 55 60

-continued

```
Cys Asn Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110


<210> SEQ ID NO 28
<211> LENGTH: 1845
<212> TYPE: DNA
<213> ORGANISM: Artificial Sequence
<220> FEATURE:
<223> OTHER INFORMATION: RT115 rbcLS
<220> FEATURE:
<221> NAME/KEY: CDS
<222> LOCATION: (1)...(1419)
<223> OTHER INFORMATION: RT115 rbcL
<220> FEATURE:
<221> NAME/KEY: CDS
<222> LOCATION: (1510)...(1845)
<223> OTHER INFORMATION: RT115 rbcS

<400> SEQUENCE: 28

atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                  10                  15

tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
            20                  25                  30

ctg ctg gcg gct ttc cgc ttc agc cct cag ccg ggt gtc cct gct gac      144
Leu Leu Ala Ala Phe Arg Phe Ser Pro Gln Pro Gly Val Pro Ala Asp
        35                  40                  45

gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
    50                  55                  60

acc gtg tgg acc gac ttg ctg acc gac atg gat cgg tac aaa ggc aag      240
Thr Val Trp Thr Asp Leu Leu Thr Asp Met Asp Arg Tyr Lys Gly Lys
 65                 70                  75                  80

tgc tac cac atc gag ccg gtg caa ggc gaa gag aac tcc tac ttt gcg      288
Cys Tyr His Ile Glu Pro Val Gln Gly Glu Glu Asn Ser Tyr Phe Ala
                85                  90                  95

ttc atc gct tac ccg ctc gac ctg ttt gaa gaa ggg tcg gtc acc aac      336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc      432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac      480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag cct ttc      624
Gly Leu Asp Phe Thr Lys Asp Asp Glu Asn Ile Asn Ser Gln Pro Phe
        195                 200                 205
```

-continued

```
atg cgt tgg cgc gat cgc ttc ctg ttt gtg gct gat gca atc cac aaa      672
Met Arg Trp Arg Asp Arg Phe Leu Phe Val Ala Asp Ala Ile His Lys
    210                 215                 220

tcg caa gca gaa acc ggt gaa acc aag ggt cac tac ctg aac gtg acc      720
Ser Gln Ala Glu Thr Gly Glu Thr Lys Gly His Tyr Leu Asn Val Thr
225                 230                 235                 240

gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc acc      816
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
        275                 280                 285

cac atc cac cgt gca atg cac gcg gtg atc gac cgt cag cgt aac cac      912
His Ile His Arg Ala Met His Ala Val Ile Asp Arg Gln Arg Asn His
    290                 295                 300

ggg att cac ttc cgt gtc ttg gcc aag tgc ctg cgc ctc tcc ggt ggc      960
Gly Ile His Phe Arg Val Leu Ala Lys Cys Leu Arg Leu Ser Gly Gly
305                 310                 315                 320

gac cag ctc cac acc ggc acc gtg gtg ggc aag ctc gag ggt gac cgt     1008
Asp Gln Leu His Thr Gly Thr Val Val Gly Lys Leu Glu Gly Asp Arg
                325                 330                 335

cag acc acc ctg ggc ttc atc gac cag ctg cgc gaa tcc ttc atc ccc     1056
Gln Thr Thr Leu Gly Phe Ile Asp Gln Leu Arg Glu Ser Phe Ile Pro
            340                 345                 350

gaa gac cgc acc cgc ggc aac ttc ttc gat cag gac tgg ggt tcg atg     1104
Glu Asp Arg Thr Arg Gly Asn Phe Phe Asp Gln Asp Trp Gly Ser Met
        355                 360                 365

ccc ggc gtc ttc gcc gtg gcc tcc ggc ggc atc cac gtg tgg cac atg     1152
Pro Gly Val Phe Ala Val Ala Ser Gly Gly Ile His Val Trp His Met
    370                 375                 380

ccc gcc ctg gtg gaa atc ttc ggt gat gac tcc gtt ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc     1296
Asn Arg Val Ala Leu Glu Ala Cys Val Gln Ala Arg Asn Glu Gly Arg
            420                 425                 430

gac ctc tac cgt gaa ggc ggc gac atc ctt cgt gag gct ggc aag tgg     1344
Asp Leu Tyr Arg Glu Gly Gly Asp Ile Leu Arg Glu Ala Gly Lys Trp
        435                 440                 445

tcg cct gaa ctg gct gca gct ctc gac ctc tgg aaa gag atc aag ttc     1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg           1439
Glu Phe Glu Thr Met Asp Lys Leu  *
465                 470

ggggagtgag cgttgctgcg taaagctttc tccccagcct ttcgacttaa cctttcagga   1499

tttctgaatc atg agc atg aaa act ctg ccc aaa gag cgt cgt ttc gag      1548
            Met Ser Met Lys Thr Leu Pro Lys Glu Arg Arg Phe Glu
                    475                 480                 485

act ttc tcg tac ctg cct ccc ctc agc gat cgc caa atc gct gca caa     1596
Thr Phe Ser Tyr Leu Pro Pro Leu Ser Asp Arg Gln Ile Ala Ala Gln
                490                 495                 500
```

-continued

```
atc gag tac atg atc gag caa ggc ttc cac ccc ttg atc gag ttc aac      1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc      1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag      1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac      1788
Cys Arg Ser Glu Tyr Gly Asp Cys Tyr Ile Arg Val Ala Gly Phe Asp
550                 555                 560                 565

aac atc aag cag tgc caa acc gtg ggc ttc atc gtt cat cgt ccc ggc      1836
Asn Ile Lys Gln Cys Gln Thr Val Gly Phe Ile Val His Arg Pro Gly
                570                 575                 580

cgc tac taa                                                          1845
Arg Tyr  *


<210> SEQ ID NO 29
<211> LENGTH: 472
<212> TYPE: PRT
<213> ORGANISM: Artificial Sequence
<220> FEATURE:
<223> OTHER INFORMATION: RT115 rbcL

<400> SEQUENCE: 29

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Met Arg Trp Arg Asp Arg Phe Leu Phe Val Ala Asp Ala Ile His Lys
    210                 215                 220

Ser Gln Ala Glu Thr Gly Glu Thr Lys Gly His Tyr Leu Asn Val Thr
225                 230                 235                 240

Ala Pro Thr Cys Glu Glu Met Met Lys Arg Ala Glu Phe Ala Lys Glu
```

-continued

```
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp Gln Leu His Thr Gly Thr Val Val Gly Lys Leu Glu Gly Asp Arg
                325                 330                 335

Gln Thr Thr Leu Gly Phe Ile Asp Gln Leu Arg Glu Ser Phe Ile Pro
            340                 345                 350

Glu Asp Arg Thr Arg Gly Asn Phe Phe Asp Gln Asp Trp Gly Ser Met
        355                 360                 365

Pro Gly Val Phe Ala Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470


<210> SEQ ID NO 30
<211> LENGTH: 111
<212> TYPE: PRT
<213> ORGANISM: Artificial Sequence
<220> FEATURE:
<223> OTHER INFORMATION: RT115 rbcS

<400> SEQUENCE: 30

Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Gly Phe Ile Val His Arg Pro Gly Arg Tyr
            100                 105                 110


<210> SEQ ID NO 31
<211> LENGTH: 1845
<212> TYPE: DNA
```

-continued

<213> ORGANISM: Artificial Sequence
<220> FEATURE:
<223> OTHER INFORMATION: RT116 rbcLS
<220> FEATURE:
<221> NAME/KEY: CDS
<222> LOCATION: (1)...(1419)
<223> OTHER INFORMATION: RT116 rbcL
<220> FEATURE:
<221> NAME/KEY: CDS
<222> LOCATION: (1510)...(1845)
<223> OTHER INFORMATION: RT116 rbcS

<400> SEQUENCE: 31

```
atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                  10                  15

tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
            20                  25                  30

ctg ctg gcg gct ttc cgc ttc agc cct cag ccg ggt gtc cct gct gac      144
Leu Leu Ala Ala Phe Arg Phe Ser Pro Gln Pro Gly Val Pro Ala Asp
        35                  40                  45

gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
    50                  55                  60

acc gtg tgg acc gac ttg ctg acc gac atg gat cgg tac aaa ggc aag      240
Thr Val Trp Thr Asp Leu Leu Thr Asp Met Asp Arg Tyr Lys Gly Lys
 65                  70                  75                  80

tgc tac cac atc gag ccg gtg caa ggc gaa gag aac tcc tac ttt gcg      288
Cys Tyr His Ile Glu Pro Val Gln Gly Glu Glu Asn Ser Tyr Phe Ala
                85                  90                  95

ttc atc gct tac ccg ctc gac ctg ttt gaa gaa ggg tcg gtc acc aac      336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc      432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac      480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc      720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc acc      816
```

-continued

```
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg       864
Ala Asn Thr Thr Leu Ala Lys Trp Cys Arg Asp Asn Gly Val Leu Leu
        275                 280                 285

cac atc cac cgt gca atg cac gcg gcg atc gac cgt cag cgt aac cac       912
His Ile His Arg Ala Met His Ala Ala Ile Asp Arg Gln Arg Asn His
    290                 295                 300

ggg att cac ttc cgc gtt ttg gct aag tgt ttg cgt ctg tcc ggt ggt       960
Gly Ile His Phe Arg Val Leu Ala Lys Cys Leu Arg Leu Ser Gly Gly
305                 310                 315                 320

gac cac ctc cac tcc ggc acc gtc gtc ggc aaa ctg gaa ggc gac aaa      1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa      1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg      1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg      1152
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt      1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg      1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc      1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg      1344
Asp Leu Tyr Arg Glu Gly Gly Asp Ile Leu Arg Glu Ala Gly Lys Trp
        435                 440                 445

tcg cct gaa ctg gct gct gcc ctc gac ctc tgg aaa gag atc aag ttc      1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg            1439
Glu Phe Glu Thr Met Asp Lys Leu  *
465                 470

ggggagtgag cgttgctgcg taaagctttc tccccagcct ttcgacttaa cctttcagga    1499

tttctgaatc atg agc atg aaa act ctg ccc aaa gag cgt cgt ttc gag       1548
            Met Ser Met Lys Thr Leu Pro Lys Glu Arg Arg Phe Glu
                    475                 480                 485

act ttc tcg tac ctg cct ccc ctc agc gat cgc caa atc gct gca caa      1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac      1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc      1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag      1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac      1788
Cys Arg Ser Glu Tyr Gly Asp Cys Tyr Ile Arg Val Ala Gly Phe Asp
```

-continued

```
550                 555                 560                 565

aac atc aag cag tgc caa acc gtg agc ttc atc gtt cat cgt ccc ggc      1836
Asn Ile Lys Gln Cys Gln Thr Val Ser Phe Ile Val His Arg Pro Gly
                570                 575                 580

cgc tac taa                                                          1845
Arg Tyr  *


<210> SEQ ID NO 32
<211> LENGTH: 472
<212> TYPE: PRT
<213> ORGANISM: Artificial Sequence
<220> FEATURE:
<223> OTHER INFORMATION: RT116 rbcL

<400> SEQUENCE: 32

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Ala Ile Asp Arg Gln Arg Asn His
    290                 295                 300

Gly Ile His Phe Arg Val Leu Ala Lys Cys Leu Arg Leu Ser Gly Gly
305                 310                 315                 320
```

-continued

```
Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470
```

<210> SEQ ID NO 33
<211> LENGTH: 111
<212> TYPE: PRT
<213> ORGANISM: Artificial Sequence
<220> FEATURE:
<223> OTHER INFORMATION: RT116 rbcS

<400> SEQUENCE: 33

```
Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110
```

<210> SEQ ID NO 34
<211> LENGTH: 1845
<212> TYPE: DNA
<213> ORGANISM: Artificial Sequence
<220> FEATURE:
<223> OTHER INFORMATION: RT117 rbcLS
<220> FEATURE:
<221> NAME/KEY: CDS
<222> LOCATION: (1)...(1419)
<223> OTHER INFORMATION: RT117 rbcL
<220> FEATURE:
<221> NAME/KEY: CDS
<222> LOCATION: (1510)...(1845)
<223> OTHER INFORMATION: RT117 rbcS

<400> SEQUENCE: 34

-continued

```
atg ccc aag acg caa tct gcc gca ggc tat aag gcc ggg gtg aag gac        48
Met Pro Lys Thr Gln Ser Ala Ala Gly Tyr Lys Ala Gly Val Lys Asp
 1               5                  10                  15

tac aaa ctc acc tat tac acc ccc gat tac acc ccc aaa gac act gac        96
Tyr Lys Leu Thr Tyr Tyr Thr Pro Asp Tyr Thr Pro Lys Asp Thr Asp
            20                  25                  30

ctg ctg gcg gct ttc cgc ttc agc cct cag ccg ggt gtc cct gct gac       144
Leu Leu Ala Ala Phe Arg Phe Ser Pro Gln Pro Gly Val Pro Ala Asp
        35                  40                  45

gaa gct ggt gcg gcg atc gcg gct gaa tct tcg acc ggt acc tgg acc       192
Glu Ala Gly Ala Ala Ile Ala Ala Glu Ser Ser Thr Gly Thr Trp Thr
    50                  55                  60

acc gtg tgg acc gac ttg ctg acc gac atg gat cgg tac aaa ggc aag       240
Thr Val Trp Thr Asp Leu Leu Thr Asp Met Asp Arg Tyr Lys Gly Lys
 65                  70                  75                  80

tgc tac cac atc gag ccg gtg caa ggc gaa gag aac tcc tac ttt gcg       288
Cys Tyr His Ile Glu Pro Val Gln Gly Glu Glu Asn Ser Tyr Phe Ala
                85                  90                  95

ttc atc gct tac ccg ctc gac ctg ttt gaa gaa ggg tcg gtc acc aac       336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt       384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc       432
Ser Leu Arg Leu Glu Asp Ile Arg Phe Pro Val Ala Leu Val Lys Thr
    130                 135                 140

ttc caa ggt cct tcc cac ggt atc caa gtc gag cgc gac ctg ctg aac       480
Phe Gln Gly Pro Ser His Gly Ile Gln Val Glu Arg Asp Leu Leu Asn
145                 150                 155                 160

aag tac ggc cgt ccg atg ctg ggt tgc acg atc aaa cca aaa ctc ggt       528
Lys Tyr Gly Arg Pro Met Leu Gly Cys Thr Ile Lys Pro Lys Leu Gly
                165                 170                 175

ctg tcg gcg aaa aac tac ggt cgt gca gta tac gaa tgt ctg cgc ggt       576
Leu Ser Ala Lys Asn Tyr Gly Arg Ala Val Tyr Glu Cys Leu Arg Gly
            180                 185                 190

ggt ttg gac ttc acc aaa gac gac gaa aac atc aac tct cag cct ttc       624
Gly Leu Asp Phe Thr Lys Asp Asp Glu Asn Ile Asn Ser Gln Pro Phe
        195                 200                 205

atg cgt tgg cgc gat cgc ttc ctg ttt gta caa gaa gca att gaa aaa       672
Met Arg Trp Arg Asp Arg Phe Leu Phe Val Gln Glu Ala Ile Glu Lys
    210                 215                 220

gct caa gct gaa act ggc gaa atc aag ggt cac tac ttg aac gta act       720
Ala Gln Ala Glu Thr Gly Glu Ile Lys Gly His Tyr Leu Asn Val Thr
225                 230                 235                 240

gct cct acc tgt gag caa atg atg gaa cgt gca gct ttc gct aag gaa       768
Ala Pro Thr Cys Glu Gln Met Met Glu Arg Ala Ala Phe Ala Lys Glu
                245                 250                 255

atc ggc aca cca atc atc atg cat gac ttc ttg act ggt ggt ttc aca       816
Ile Gly Thr Pro Ile Ile Met His Asp Phe Leu Thr Gly Gly Phe Thr
            260                 265                 270

gca aac acc tct ctt gct aag tat tgc cgt gac aat ggc ttg ctc ttg       864
Ala Asn Thr Ser Leu Ala Lys Tyr Cys Arg Asp Asn Gly Leu Leu Leu
        275                 280                 285

cac att cac cgc gct atg cac gca gtt atc gac cgt caa aaa acc cac       912
His Ile His Arg Ala Met His Ala Val Ile Asp Arg Gln Lys Thr His
    290                 295                 300

ggg att cac ttc cgc gtt ttg gcc aag tgt ttg cgt ctg tcc ggt ggt       960
Gly Ile His Phe Arg Val Leu Ala Lys Cys Leu Arg Leu Ser Gly Gly
305                 310                 315                 320
```

-continued

```
gac cac ctc cac tcc ggc acc gtc gtc ggc aaa ctg gaa ggc gac aaa      1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa      1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg      1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg      1152
Pro Gly Val Leu Pro Val Ala Ser Gly Gly Ile His Val Trp His Met
    370                 375                 380

ccc gcc ctg gtc gcc atc ttc ggt gac gac tcc gtg ctc cag ttc ggt      1200
Pro Ala Leu Val Ala Ile Phe Gly Asp Asp Ser Val Leu Gln Phe Gly
385                 390                 395                 400

ggt ggc acc ttg ggt cac ccc tgg ggt aat gct cct ggt gca acc gcg      1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc      1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg      1344
Asp Leu Tyr Arg Glu Gly Gly Asp Ile Leu Arg Glu Ala Gly Lys Trp
        435                 440                 445

tcg cct gaa ctg gct gct gcc ctc gac ctc tgg aaa gag atc aag ttc      1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg            1439
Glu Phe Glu Thr Met Asp Lys Leu  *
465                 470

ggggagtgag cgttgctgcg taaagctttc tccccagcct ttcgacttaa cctttcagga   1499

tttctgaatc atg agc atg aaa act ctg ccc aaa gag cgt cgt ttc gag      1548
            Met Ser Met Lys Thr Leu Pro Lys Glu Arg Arg Phe Glu
                    475                 480                 485

act ttc tcg tac ctg cct ccc ctc agc gat cgc caa atc gct gca caa      1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac      1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc      1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag      1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac      1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt ccc ggc      1836
Asn Ile Lys Gln Cys Gln Thr Val Ser Phe Ile Val His Arg Pro Gly
                570                 575                 580

cgc tac taa                                                          1845
Arg Tyr  *
```

<210> SEQ ID NO 35
<211> LENGTH: 472
<212> TYPE: PRT
<213> ORGANISM: Artificial Sequence -continued
<220> FEATURE:
<223> OTHER INFORMATION: RT117 rbcL

<400> SEQUENCE: 35

```
Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Ser His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Met Arg Trp Arg Asp Arg Phe Leu Phe Val Gln Glu Ala Ile Glu Lys
    210                 215                 220

Ala Gln Ala Glu Thr Gly Glu Ile Lys Gly His Tyr Leu Asn Val Thr
225                 230                 235                 240

Ala Pro Thr Cys Glu Gln Met Met Glu Arg Ala Ala Phe Ala Lys Glu
                245                 250                 255

Ile Gly Thr Pro Ile Ile Met His Asp Phe Leu Thr Gly Gly Phe Thr
            260                 265                 270

Ala Asn Thr Ser Leu Ala Lys Tyr Cys Arg Asp Asn Gly Leu Leu Leu
        275                 280                 285

His Ile His Arg Ala Met His Ala Val Ile Asp Arg Gln Lys Thr His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Ala Ile Phe Gly Asp Asp Ser Val Leu Gln Phe Gly
385                 390                 395                 400
```

-continued

```
Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470


<210> SEQ ID NO 36
<211> LENGTH: 111
<212> TYPE: PRT
<213> ORGANISM: Artificial Sequence
<220> FEATURE:
<223> OTHER INFORMATION: RT117 rbcS

<400> SEQUENCE: 36

Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110


<210> SEQ ID NO 37
<211> LENGTH: 1845
<212> TYPE: DNA
<213> ORGANISM: Artificial Sequence
<220> FEATURE:
<223> OTHER INFORMATION: RT118 rbcLS
<220> FEATURE:
<221> NAME/KEY: CDS
<222> LOCATION: (1)...(1419)
<223> OTHER INFORMATION: RT118 rbcL
<220> FEATURE:
<221> NAME/KEY: CDS
<222> LOCATION: (1510)...(1845)
<223> OTHER INFORMATION: RT118 rbcS

<400> SEQUENCE: 37

atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                   10                  15

tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
            20                   25                  30

ctg ctg gcg gct ttc cgc ttc agc cct cag ccg ggt gtc cct gct gac      144
Leu Leu Ala Ala Phe Arg Phe Ser Pro Gln Pro Gly Val Pro Ala Asp
         35                  40                  45

gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
```

-continued

```
     50                  55                  60

acc gtg tgg acc gac ttg ctg acc gac atg gat cgg tac aaa ggc aag       240
Thr Val Trp Thr Asp Leu Leu Thr Asp Met Asp Arg Tyr Lys Gly Lys
 65                  70                  75                  80

tgc tac cac atc gag ccg gtg caa ggc gaa gag aac ttc tac ttt gcg       288
Cys Tyr His Ile Glu Pro Val Gln Gly Glu Glu Asn Phe Tyr Phe Ala
                 85                  90                  95

ttc atc gct tac ccg ctc gac ctg ttt gaa gaa ggt tcg gtc acc aac       336
Phe Ile Ala Tyr Pro Leu Asp Leu Phe Glu Glu Gly Ser Val Thr Asn
            100                 105                 110

atc ctg acc ttg atc gtc ggt aac gtg ttt ggc ttc aaa gct atc cgt       384
Ile Leu Thr Leu Ile Val Gly Asn Val Phe Gly Phe Lys Ala Ile Arg
        115                 120                 125

tcg ctg cgt ctg gaa gac att cgc ttc ccc gtc gcc ttg gtc aaa acc       432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac       480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt       528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc       576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tct cag cct ttc       624
Gly Leu Asp Phe Thr Lys Asp Asp Glu Asn Ile Asn Ser Gln Pro Phe
        195                 200                 205

atg cgt tgg cgc gat cgc ttc ctg ttt gta caa gaa gca att gaa aaa       672
Met Arg Trp Arg Asp Arg Phe Leu Phe Val Gln Glu Ala Ile Glu Lys
    210                 215                 220

gct caa gct gaa act ggc gaa acc aag ggt cac tac ttg aac gta act       720
Ala Gln Ala Glu Thr Gly Glu Thr Lys Gly His Tyr Leu Asn Val Thr
225                 230                 235                 240

gct cct acc tgt gag caa atg atg gaa cgt gca gct ttc gct aag gaa       768
Ala Pro Thr Cys Glu Gln Met Met Glu Arg Ala Ala Phe Ala Lys Glu
                245                 250                 255

atc ggc aca cca atc atc atg cat gac ttc ttg act ggt ggt ttc aca       816
Ile Gly Thr Pro Ile Ile Met His Asp Phe Leu Thr Gly Gly Phe Thr
            260                 265                 270

gca aac acc tct ctt gct aag tat tgc cgt gac aat ggc ttg ctc ttg       864
Ala Asn Thr Ser Leu Ala Lys Tyr Cys Arg Asp Asn Gly Leu Leu Leu
        275                 280                 285

cac atc cac cgt gca atg cac gcg gtg atc gac cgt cag cgt aac cac       912
His Ile His Arg Ala Met His Ala Val Ile Asp Arg Gln Arg Asn His
    290                 295                 300

ggg att cac ttc cgt gtc ttg gcc aag tgt ttg cgt ctg tcc ggt ggt       960
Gly Ile His Phe Arg Val Leu Ala Lys Cys Leu Arg Leu Ser Gly Gly
305                 310                 315                 320

gac cac ctc cac tcc ggc acc gtc gtc ggc aaa ctg gaa ggc gac aaa      1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa      1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg      1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg      1152
```

-continued

```
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc     1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg     1344
Asp Leu Tyr Arg Glu Gly Gly Asp Ile Leu Arg Glu Ala Gly Lys Trp
        435                 440                 445

tcg cct gaa ctg gct gct gcc ctc gac ctc tgg aaa gag atc aag ttc     1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg           1439
Glu Phe Glu Thr Met Asp Lys Leu  *
465                 470

ggggagtgag cgttgctgcg taaagctttc tccccagcct ttcgacttaa cctttcagga   1499

tttctgaatc atg agc atg aaa act ctg ccc aaa gag cgt cgt ttc gag      1548
            Met Ser Met Lys Thr Leu Pro Lys Glu Arg Arg Phe Glu
                    475                 480                 485

act ttc tcg tac ctg cct ccc ctc agc gat cgc caa atc gct gca caa     1596
Thr Phe Ser Tyr Leu Pro Pro Leu Ser Asp Arg Gln Ile Ala Ala Gln
                490                 495                 500

atc gag tac acg atc gag caa ggc ttc cac ccc ttg atc gag ttc aac     1644
Ile Glu Tyr Thr Ile Glu Gln Gly Phe His Pro Leu Ile Glu Phe Asn
            505                 510                 515

gag cac tcg aat ccg gaa gag ttc tac tgg acg atg tgg aag ctc ccc     1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag     1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac     1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt ccc ggc     1836
Asn Ile Lys Gln Cys Gln Thr Val Ser Phe Ile Val His Arg Pro Gly
                570                 575                 580

cgc tac taa                                                         1845
Arg Tyr  *


<210> SEQ ID NO 38
<211> LENGTH: 472
<212> TYPE: PRT
<213> ORGANISM: Artificial Sequence
<220> FEATURE:
<223> OTHER INFORMATION: RT118 rbcL

<400> SEQUENCE: 38

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45
```

-continued

```
Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Phe Tyr Phe Ala
                85                  90                  95

Phe Ile Ala Tyr Pro Leu Asp Leu Phe Glu Glu Gly Ser Val Thr Asn
            100                 105                 110

Ile Leu Thr Leu Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Met Arg Trp Arg Asp Arg Phe Leu Phe Val Gln Glu Ala Ile Glu Lys
    210                 215                 220

Ala Gln Ala Glu Thr Gly Glu Thr Lys Gly His Tyr Leu Asn Val Thr
225                 230                 235                 240

Ala Pro Thr Cys Glu Gln Met Met Glu Arg Ala Ala Phe Ala Lys Glu
                245                 250                 255

Ile Gly Thr Pro Ile Ile Met His Asp Phe Leu Thr Gly Gly Phe Thr
            260                 265                 270

Ala Asn Thr Ser Leu Ala Lys Tyr Cys Arg Asp Asn Gly Leu Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
```

-continued

```
465                 470


<210> SEQ ID NO 39
<211> LENGTH: 111
<212> TYPE: PRT
<213> ORGANISM: Artificial Sequence
<220> FEATURE:
<223> OTHER INFORMATION: RT118 rbcS

<400> SEQUENCE: 39

Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30

Thr Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110


<210> SEQ ID NO 40
<211> LENGTH: 1845
<212> TYPE: DNA
<213> ORGANISM: Artificial Sequence
<220> FEATURE:
<223> OTHER INFORMATION: F2A-10 rbcLS
<220> FEATURE:
<221> NAME/KEY: CDS
<222> LOCATION: (1)...(1419)
<223> OTHER INFORMATION: F2A-10 rbcL
<220> FEATURE:
<221> NAME/KEY: CDS
<222> LOCATION: (1510)...(1845)
<223> OTHER INFORMATION: F2A-10 rbcS

<400> SEQUENCE: 40

atg ccc aag acg caa tct gcc gca ggc tat aag gcc ggg gtg aag gac        48
Met Pro Lys Thr Gln Ser Ala Ala Gly Tyr Lys Ala Gly Val Lys Asp
 1               5                  10                  15

tac aaa ctc acc tat tac acc ccc gat tac acc ccc aaa gac act gac        96
Tyr Lys Leu Thr Tyr Tyr Thr Pro Asp Tyr Thr Pro Lys Asp Thr Asp
            20                  25                  30

ctg ctg gcg gct ttc cgc ttc agc cct cag ccg ggt gtc cct gct gac       144
Leu Leu Ala Ala Phe Arg Phe Ser Pro Gln Pro Gly Val Pro Ala Asp
        35                  40                  45

gaa gct ggt gcg gcg atc gcg gct gaa tct tcg acc ggt acc tgg acc       192
Glu Ala Gly Ala Ala Ile Ala Ala Glu Ser Ser Thr Gly Thr Trp Thr
    50                  55                  60

acc gtg tgg acc gac ttg ctg acc gac atg gat cgg tac aaa ggc aag       240
Thr Val Trp Thr Asp Leu Leu Thr Asp Met Asp Arg Tyr Lys Gly Lys
65                  70                  75                  80

tgc tac cac atc gag ccg gtg caa ggc gaa gag aac tcc tac ttt gcg       288
Cys Tyr His Ile Glu Pro Val Gln Gly Glu Glu Asn Ser Tyr Phe Ala
                85                  90                  95

ttc atc gct tac ccg ctc gac ctg ttt gaa gaa ggg tcg gtc acc aac       336
Phe Ile Ala Tyr Pro Leu Asp Leu Phe Glu Glu Gly Ser Val Thr Asn
            100                 105                 110
```

-continued

```
atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc      432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac      480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc      720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc acc      816
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
        275                 280                 285

cac atc cac cgt gca atg cac gcg gtg atc gac cgt cag cgt aac cac      912
His Ile His Arg Ala Met His Ala Val Ile Asp Arg Gln Arg Asn His
    290                 295                 300

ggg att cac ttc cgt gtc ttg gcc aag tgt ttg cgt ctg tcc ggt ggt      960
Gly Ile His Phe Arg Val Leu Ala Lys Cys Leu Arg Leu Ser Gly Gly
305                 310                 315                 320

gac cac ctc cac tcc ggc acc gtc gtc ggc aaa ctg gaa ggc gac aaa     1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa     1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg     1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg     1152
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
                405                 410                 415

aac cgt gtt gcc ttg gaa gct tgc gtc caa gca cgt aac gaa ggt cgc     1296
Asn Arg Val Ala Leu Glu Ala Cys Val Gln Ala Arg Asn Glu Gly Arg
            420                 425                 430
```

-continued

```
gac ctc tac cgt gaa ggc ggc gac atc ctt cgt gaa gct ggc aag tgg     1344
Asp Leu Tyr Arg Glu Gly Gly Asp Ile Leu Arg Glu Ala Gly Lys Trp
        435                 440                 445

tcg cct gag ctg gcc atc gcc ctc gac ctc tgg aaa gag atc aag ttc     1392
Ser Pro Glu Leu Ala Ile Ala Leu Asp Leu Trp Lys Glu Ile Lys Phe
    450                 455                 460

gaa ttc gaa acg atg gac aag ctc taa ggagcctctg actatcgctg           1439
Glu Phe Glu Thr Met Asp Lys Leu  *
465                 470

ggggagtgag cgttgctgcg taaagctttc tccccagcct ttcgacttaa cctttcagga   1499

tttctgaatc atg agc atg aaa act ctg ccc aaa gag cgt cgt ttc gag      1548
            Met Ser Met Lys Thr Leu Pro Lys Glu Arg Arg Phe Glu
                    475                 480                 485

act ttc tcg tac ctg cct ccc ctc agc gat cgc caa atc gct gca caa     1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac     1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc     1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag     1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac     1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt ccc ggt     1836
Asn Ile Lys Gln Cys Gln Thr Val Ser Phe Ile Val His Arg Pro Gly
                570                 575                 580

cgc tac taa                                                         1845
Arg Tyr  *


<210> SEQ ID NO 41
<211> LENGTH: 472
<212> TYPE: PRT
<213> ORGANISM: Artificial Sequence
<220> FEATURE:
<223> OTHER INFORMATION: F2A-10 rbcL

<400> SEQUENCE: 41

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125
```

-continued

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ile Ala Leu Asp Leu Trp Lys Glu Ile Lys Phe
    450                 455                 460

Glu Phe Glu Thr Met Asp Lys Leu
465                 470

<210> SEQ ID NO 42
<211> LENGTH: 111
<212> TYPE: PRT
<213> ORGANISM: Artificial Sequence
<220> FEATURE:
<223> OTHER INFORMATION: F2A-10 rbcS

<400> SEQUENCE: 42

Met Ser Met Lys Thr Leu Pro Lys Glu Arg Arg Phe Glu Thr Phe Ser
 1               5                  10                  15

-continued

```
Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110


<210> SEQ ID NO 43
<211> LENGTH: 1845
<212> TYPE: DNA
<213> ORGANISM: Artificial Sequence
<220> FEATURE:
<223> OTHER INFORMATION: F2A-16 rbcLS
<220> FEATURE:
<221> NAME/KEY: CDS
<222> LOCATION: (1)...(1419)
<223> OTHER INFORMATION: F2A-16 rbcL
<220> FEATURE:
<221> NAME/KEY: CDS
<222> LOCATION: (1510)...(1845)
<223> OTHER INFORMATION: F2A-16 rbcS

<400> SEQUENCE: 43

atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                  10                  15

tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
            20                  25                  30

ctg ctg gcg gct ttc cgc ttc agc cct cag ccg ggt gtc cct gct gac      144
Leu Leu Ala Ala Phe Arg Phe Ser Pro Gln Pro Gly Val Pro Ala Asp
        35                  40                  45

gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
     50                  55                  60

acc gtg tgg acc gac ttg ctg acc gac atg gat cgg tac aaa ggc aag      240
Thr Val Trp Thr Asp Leu Leu Thr Asp Met Asp Arg Tyr Lys Gly Lys
 65                  70                  75                  80

tgc tac cac atc gag ccg gtg caa ggc gaa gag aac tcc tac ttt gcg      288
Cys Tyr His Ile Glu Pro Val Gln Gly Glu Glu Asn Ser Tyr Phe Ala
                 85                  90                  95

ttc atc gct tac ccg ctc gac ctg ttt gaa gaa ggg tcg gtc acc aac      336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc      432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac      480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
```

-continued

```
            165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc      720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc acc      816
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
        275                 280                 285

cac atc cac cgt gca atg cac gcg gtg atc gac cgt cag cgt aac cac      912
His Ile His Arg Ala Met His Ala Val Ile Asp Arg Gln Arg Asn His
    290                 295                 300

ggg att cac ttc cgt gtc ttg gcc aag tgt ttg cgt ctg tcc ggt ggt      960
Gly Ile His Phe Arg Val Leu Ala Lys Cys Leu Arg Leu Ser Gly Gly
305                 310                 315                 320

gac cac ctc cac tcc ggc acc gtc gtc ggc aaa ctg gaa ggc gac aaa     1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa     1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg     1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg     1152
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc     1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg     1344
Asp Leu Tyr Arg Glu Gly Gly Asp Ile Leu Arg Glu Ala Gly Lys Trp
        435                 440                 445

tcg cct gaa ctg gct gct gcc ctc gac ctc tgg aaa gag atc aag ttc     1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg           1439
Glu Phe Glu Thr Met Asp Lys Leu  *
465                 470

ggggagtgag cgttgctgcg taaagctttc tccccagcct ttcgacttaa cctttcagga   1499
```

-continued

```
tttctgaatc atg agc atg aaa act ctg ccc aaa gag cgt cgt ttc gag      1548
           Met Ser Met Lys Thr Leu Pro Lys Glu Arg Arg Phe Glu
                   475                 480                 485

act ttc tcg tac ctg cct ccc ctc agc gat cgc caa atc gct gca caa     1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac     1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc     1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag     1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac     1788
Cys Arg Ser Glu Tyr Gly Asp Cys Tyr Ile Arg Val Ala Gly Phe Asp
550                 555                 560                 565

aac atc aag cag tgc caa acc gtg ggc ttc atc gtt cat cgt ccc ggc     1836
Asn Ile Lys Gln Cys Gln Thr Val Gly Phe Ile Val His Arg Pro Gly
                570                 575                 580

cgc tac taa                                                         1845
Arg Tyr  *


<210> SEQ ID NO 44
<211> LENGTH: 472
<212> TYPE: PRT
<213> ORGANISM: Artificial Sequence
<220> FEATURE:
<223> OTHER INFORMATION: F2A-16 rbcL

<400> SEQUENCE: 44

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
```

-continued

```
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470


<210> SEQ ID NO 45
<211> LENGTH: 111
<212> TYPE: PRT
<213> ORGANISM: Artificial Sequence
<220> FEATURE:
<223> OTHER INFORMATION: F2A-16 rbcS

<400> SEQUENCE: 45

Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
```

-continued

```
            85                  90                  95

Gln Cys Gln Thr Val Gly Phe Ile Val His Arg Pro Gly Arg Tyr
        100                 105                 110


<210> SEQ ID NO 46
<211> LENGTH: 1845
<212> TYPE: DNA
<213> ORGANISM: Artificial Sequence
<220> FEATURE:
<223> OTHER INFORMATION: F2A-20 rbcLS
<220> FEATURE:
<221> NAME/KEY: CDS
<222> LOCATION: (1)...(1419)
<223> OTHER INFORMATION: F2A-20 rbcL
<220> FEATURE:
<221> NAME/KEY: CDS
<222> LOCATION: (1510)...(1845)
<223> OTHER INFORMATION: F2A-20 rbcS

<400> SEQUENCE: 46

atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                  10                  15

tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
            20                  25                  30

ctg ctg gcg gct ttc cgc ttc agc cct cag ccg ggt gtc cct gct gac      144
Leu Leu Ala Ala Phe Arg Phe Ser Pro Gln Pro Gly Val Pro Ala Asp
        35                  40                  45

gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
    50                  55                  60

acc gtg tgg acc gac ttg ctg acc gac atg gat cgg tac aaa ggc aag      240
Thr Val Trp Thr Asp Leu Leu Thr Asp Met Asp Arg Tyr Lys Gly Lys
 65                  70                  75                  80

tgc tac cac atc gag ccg gtg caa ggc gaa gag aac tcc tac ttt gcg      288
Cys Tyr His Ile Glu Pro Val Gln Gly Glu Glu Asn Ser Tyr Phe Ala
                85                  90                  95

ttc atc gct tac ccg ctc gac ctg ttt gaa gaa ggg tcg gtc acc aac      336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tca ctg cgt ctg gaa gac atc cgc ttc ccc gtc gcc ttg gtc aaa acc      432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac      480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220
```

-continued

```
tcg caa gca gaa acc ggt gaa atc aaa ggt cac tac ctg aac gtg acc      720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc acc      816
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
        275                 280                 285

cac atc cac cgt gca atg cac gcg gtg atc gac cgt cag cgt aac cac      912
His Ile His Arg Ala Met His Ala Val Ile Asp Arg Gln Arg Asn His
    290                 295                 300

ggg att cac ttc cgt gtc ttg gcc aag tgt ttg cgt ctg tcc ggt ggt      960
Gly Ile His Phe Arg Val Leu Ala Lys Cys Leu Arg Leu Ser Gly Gly
305                 310                 315                 320

gac cac ctc cac tcc ggc acc gtc gtc ggc aaa ctg gaa ggc gac aaa     1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa     1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg     1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg     1152
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc     1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg     1344
Asp Leu Tyr Arg Glu Gly Gly Asp Ile Leu Arg Glu Ala Gly Lys Trp
        435                 440                 445

tcg cgt gaa ctg gct gct gcc ctc gac ctc tgg aaa gag atc aag ttc     1392
Ser Arg Glu Leu Ala Ala Ala Leu Asp Leu Trp Lys Glu Ile Lys Phe
    450                 455                 460

gaa ttc gaa acg atg gac aag ctc taa ggagcctctg actatcgctg           1439
Glu Phe Glu Thr Met Asp Lys Leu  *
465                 470

ggggagtgag cgttgctgcg taaagctttc tccccagcct ttcgacttaa cctttcagga   1499

tttctgaatc atg agc atg aaa act ctg ccc aaa gag cgt cgt ttc gag      1548
            Met Ser Met Lys Thr Leu Pro Lys Glu Arg Arg Phe Glu
                        475                 480                 485

act ttc tcg tac ctg cct ccc ctc agc gat cgc caa atc gct gca caa     1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac     1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc     1692
```

-continued

```
Glu His Ser Asn Pro Glu Glu Phe Tyr Trp Thr Met Trp Lys Leu Pro
        520                 525                 530

ctg ttt gac tgc aag ggc cct cag caa gtc ctc gat gaa gtg cgt gag     1740
Leu Phe Asp Cys Lys Gly Pro Gln Gln Val Leu Asp Glu Val Arg Glu
    535                 540                 545

tgc cgc agc gaa tac ggt gat tgc tac atc cgt gtc gct ggc ttc gac     1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt ccc ggc     1836
Asn Ile Lys Gln Cys Gln Thr Val Ser Phe Ile Val His Arg Pro Gly
                570                 575                 580

cgc tac taa                                                         1845
Arg Tyr  *


<210> SEQ ID NO 47
<211> LENGTH: 472
<212> TYPE: PRT
<213> ORGANISM: Artificial Sequence
<220> FEATURE:
<223> OTHER INFORMATION: F2A-20 rbcL

<400> SEQUENCE: 47

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270
```

-continued

```
Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Arg Glu Leu Ala Ala Ala Leu Asp Leu Trp Lys Glu Ile Lys Phe
    450                 455                 460

Glu Phe Glu Thr Met Asp Lys Leu
465                 470
```

<210> SEQ ID NO 48
<211> LENGTH: 111
<212> TYPE: PRT
<213> ORGANISM: Artificial Sequence
<220> FEATURE:
<223> OTHER INFORMATION: F2A-20 rbcS

<400> SEQUENCE: 48

```
Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Gly Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110
```

<210> SEQ ID NO 49
<211> LENGTH: 1845
<212> TYPE: DNA
<213> ORGANISM: Artificial Sequence
<220> FEATURE:
<223> OTHER INFORMATION: F2B-2 rbcLS
<220> FEATURE:
<221> NAME/KEY: CDS -continued

```
<222> LOCATION: (1)...(1419)
<223> OTHER INFORMATION: F2B-2 rbcL
<220> FEATURE:
<221> NAME/KEY: CDS
<222> LOCATION: (1510)...(1845)
<223> OTHER INFORMATION: F2B-2 rbcS

<400> SEQUENCE: 49

atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                  10                  15

tac aaa ctc acc tat tac acc ccc gat tac acc ccc aaa gac act gac       96
Tyr Lys Leu Thr Tyr Tyr Thr Pro Asp Tyr Thr Pro Lys Asp Thr Asp
            20                  25                  30

ctg ctg gcg gct ttc cgc ttc agc cct cag ccg ggt gtc cct gct gac      144
Leu Leu Ala Ala Phe Arg Phe Ser Pro Gln Pro Gly Val Pro Ala Asp
        35                  40                  45

gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
    50                  55                  60

acc gtg tgg acc gac ttg ctg acc gac atg gat cgg tac aaa ggc aag      240
Thr Val Trp Thr Asp Leu Leu Thr Asp Met Asp Arg Tyr Lys Gly Lys
 65                  70                  75                  80

tgc tac cac atc gag ccg gtg caa ggc gaa gag aac tcc tac ttt gcg      288
Cys Tyr His Ile Glu Pro Val Gln Gly Glu Glu Asn Ser Tyr Phe Ala
                85                  90                  95

ttc atc gct tac ccg ctc gac ctg ttt gaa gaa ggg tcg gtc acc aac      336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ctg gtc aaa acc      432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac      480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220

tcg caa gca gaa acc ggt gaa atc aaa ggt cac tac ctg aac gtg acc      720
Ser Gln Ala Glu Thr Gly Glu Ile Lys Gly His Tyr Leu Asn Val Thr
225                 230                 235                 240

gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc acc      816
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
```

-continued

```
        275                 280                 285

cac atc cac cgt gca atg cac gcg gtg atc gac cgt cag cgt aac cac      912
His Ile His Arg Ala Met His Ala Val Ile Asp Arg Gln Arg Asn His
    290                 295                 300

ggg att cac ttc cgt gtc ttg gcc aag tgt ttg cgt ctg tcc ggt ggt      960
Gly Ile His Phe Arg Val Leu Ala Lys Cys Leu Arg Leu Ser Gly Gly
305                 310                 315                 320

gac cac ctc cac tcc ggc acc gtc gtc ggc aaa ctg gaa ggc gac aaa     1008
Asp His Leu His Ser Gly Thr Val Val Gly Lys Leu Glu Gly Asp Lys
                325                 330                 335

gct tcg acc ttg ggc ttt gtt gac ttg atg cgc gaa gac cac atc gaa     1056
Ala Ser Thr Leu Gly Phe Val Asp Leu Met Arg Glu Asp His Ile Glu
            340                 345                 350

gct gac cgc aac cgt ggg gtc ttc ttc acc caa gat tgg gcg tcg atg     1104
Ala Asp Arg Asn Arg Gly Val Phe Phe Thr Gln Asp Trp Ala Ser Met
        355                 360                 365

ccg ggc gtg ctg ccg gtt gct tcc ggt ggt atc cac gtg tgg cac atg     1152
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc     1296
Asn Arg Val Ala Leu Glu Ala Cys Val Gln Ala Arg Asn Glu Gly Arg
            420                 425                 430

gac ctc tac cgt gaa ggc ggc gac atc ctt cgt gaa gct ggc aag tgg     1344
Asp Leu Tyr Arg Glu Gly Gly Asp Ile Leu Arg Glu Ala Gly Lys Trp
        435                 440                 445

tcg cct gaa ctg gct gct gcc ctc gac ctc tgg aaa gag atc aag ttc     1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg           1439
Glu Phe Glu Thr Met Asp Lys Leu  *
465                 470

ggggagtgag cgttgctgcg taaagctttc tccccagcct ttcgacttaa cctttcagga   1499

tttctgaatc atg agc atg aaa act ctg ccc aaa gag cgt cgt ttc gag      1548
            Met Ser Met Lys Thr Leu Pro Lys Glu Arg Arg Phe Glu
                    475                 480                 485

act ttc tcg tac ctg cct ccc ctc agc gat cgc caa atc gct gca caa     1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac     1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc     1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag     1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac     1788
Cys Arg Ser Glu Tyr Gly Asp Cys Tyr Ile Arg Val Ala Gly Phe Asp
550                 555                 560                 565

aac atc aag cag tgc caa acc gtg agc ttc atc gtt cat cgt ccc ggc     1836
Asn Ile Lys Gln Cys Gln Thr Val Ser Phe Ile Val His Arg Pro Gly
                570                 575                 580
```

-continued

```
cgc tac taa                                                         1845
Arg Tyr  *


<210> SEQ ID NO 50
<211> LENGTH: 472
<212> TYPE: PRT
<213> ORGANISM: Artificial Sequence
<220> FEATURE:
<223> OTHER INFORMATION: F2B-2 rbcL

<400> SEQUENCE: 50

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350
```

-continued

```
Ala Asp Arg Asn Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470


<210> SEQ ID NO 51
<211> LENGTH: 111
<212> TYPE: PRT
<213> ORGANISM: Artificial Sequence
<220> FEATURE:
<223> OTHER INFORMATION: F2B-2 rbcS

<400> SEQUENCE: 51

Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Ser Phe Ile Val His Arg Pro Gly Arg Tyr
            100                 105                 110


<210> SEQ ID NO 52
<211> LENGTH: 1845
<212> TYPE: DNA
<213> ORGANISM: Artificial Sequence
<220> FEATURE:
<223> OTHER INFORMATION: F2B-3 rbcLS
<220> FEATURE:
<221> NAME/KEY: CDS
<222> LOCATION: (1)...(1419)
<223> OTHER INFORMATION: F2B-3 rbcL
<220> FEATURE:
<221> NAME/KEY: CDS
<222> LOCATION: (1510)...(1845)
<223> OTHER INFORMATION: F2B-3 rbcS

<400> SEQUENCE: 52

atg ccc aag acg caa tct gcc gca ggc tat aag gcc ggg gtg aag gac       48
Met Pro Lys Thr Gln Ser Ala Ala Gly Tyr Lys Ala Gly Val Lys Asp
 1               5                  10                  15

tac aaa ctc acc tat tac acc ccc gat tac acc ccc aaa gac act gac       96
```

-continued

```
Tyr Lys Leu Thr Tyr Tyr Thr Pro Asp Tyr Thr Pro Lys Asp Thr Asp
            20                  25                  30

ctg ctg gcg gct ttc cgc ttc agc cct cag ccg ggt gtc cct gct gac      144
Leu Leu Ala Ala Phe Arg Phe Ser Pro Gln Pro Gly Val Pro Ala Asp
        35                  40                  45

gaa gct ggt gcg gcg atc gcg gct gaa tct tcg acc ggt acc tgg acc      192
Glu Ala Gly Ala Ala Ile Ala Ala Glu Ser Ser Thr Gly Thr Trp Thr
    50                  55                  60

acc gtg tgg acc gac ttg ctg acc gac atg gat cgg tac aaa ggc aag      240
Thr Val Trp Thr Asp Leu Leu Thr Asp Met Asp Arg Tyr Lys Gly Lys
65                  70                  75                  80

tgc tac cac atc gag ccg gtg caa ggc gaa gag aac tcc tac ttt gcg      288
Cys Tyr His Ile Glu Pro Val Gln Gly Glu Glu Asn Ser Tyr Phe Ala
                85                  90                  95

ttc atc gct tac ccg ctc gac ctg ttt gaa gaa ggg tcg gtc acc aac      336
Phe Ile Ala Tyr Pro Leu Asp Leu Phe Glu Glu Gly Ser Val Thr Asn
            100                 105                 110

atc ctg acc tcg atc gtc ggt aac gtg ttt ggc ttc aaa gct atc cgt      384
Ile Leu Thr Ser Ile Val Gly Asn Val Phe Gly Phe Lys Ala Ile Arg
        115                 120                 125

tcg ctg cgt ctg gaa gac atc cgc ttc ccc gtc gcc ttg gtc aaa acc      432
Ser Leu Arg Leu Glu Asp Ile Arg Phe Pro Val Ala Leu Val Lys Thr
    130                 135                 140

ttc caa ggt cct ccc cac ggt atc caa gtc gag cgc gac ctg ctg aac      480
Phe Gln Gly Pro Pro His Gly Ile Gln Val Glu Arg Asp Leu Leu Asn
145                 150                 155                 160

aag tac ggc cgt ccg atg ctg ggt tgc acg atc aaa cca aaa ctc ggt      528
Lys Tyr Gly Arg Pro Met Leu Gly Cys Thr Ile Lys Pro Lys Leu Gly
                165                 170                 175

ctg tcg gcg aaa aac tac ggt cgt gcc gtc tac gaa tgt ctg cgc ggc      576
Leu Ser Ala Lys Asn Tyr Gly Arg Ala Val Tyr Glu Cys Leu Arg Gly
            180                 185                 190

ggt ctg gac ttc acc aaa gac gac gaa aac atc aac tcg cag ccg ttc      624
Gly Leu Asp Phe Thr Lys Asp Asp Glu Asn Ile Asn Ser Gln Pro Phe
        195                 200                 205

caa cgc tgg cgc gat cgc ttc ctg ttt gtg gct gat gca atc cac aaa      672
Gln Arg Trp Arg Asp Arg Phe Leu Phe Val Ala Asp Ala Ile His Lys
    210                 215                 220

tcg caa gca gaa acc ggt gaa acc aag ggt cac tac ctg aac gtg acc      720
Ser Gln Ala Glu Thr Gly Glu Thr Lys Gly His Tyr Leu Asn Val Thr
225                 230                 235                 240

gcg ccg acc tgc gaa gaa atg atg aaa cgg gct gag ttc gct aaa gaa      768
Ala Pro Thr Cys Glu Glu Met Met Lys Arg Ala Glu Phe Ala Lys Glu
                245                 250                 255

ctc ggc atg ccg atc atc atg cat gac ttc ttg acg gct ggt ttc act      816
Leu Gly Met Pro Ile Ile Met His Asp Phe Leu Thr Ala Gly Phe Thr
            260                 265                 270

gcc aac acc acc ttg gca aaa tgg tgc cgc gac aac ggc gtc ctg ctg      864
Ala Asn Thr Thr Leu Ala Lys Trp Cys Arg Asp Asn Gly Val Leu Leu
        275                 280                 285

cac atc cac cgc gct atg cac gca gtt atc gac cgt cag cgt aac cac      912
His Ile His Arg Ala Met His Ala Val Ile Asp Arg Gln Arg Asn His
    290                 295                 300

ggg att cac ttc cgt gtc ttg gcc aag tgt ttg cgt ctg tcc ggt ggt      960
Gly Ile His Phe Arg Val Leu Ala Lys Cys Leu Arg Leu Ser Gly Gly
305                 310                 315                 320

gat cac ctc cac tcc ggc acc gtc gtc ggc aaa ctg gaa ggc gac aaa     1008
Asp His Leu His Ser Gly Thr Val Val Gly Lys Leu Glu Gly Asp Lys
                325                 330                 335
```

-continued

```
gct tcg acc ttg ggc ttt gtt gac ttg atg cgc gaa gac cac atc gaa     1056
Ala Ser Thr Leu Gly Phe Val Asp Leu Met Arg Glu Asp His Ile Glu
            340                 345                 350

gct gac cgc agc cgt ggg gtc ttc ttc acc caa gat tgg gcg tcg atg     1104
Ala Asp Arg Ser Arg Gly Val Phe Phe Thr Gln Asp Trp Ala Ser Met
        355                 360                 365

ccg ggc gtg ctg ccg gtt gct tcc ggt ggt atc cac gtg tgg cac atg     1152
Pro Gly Val Leu Pro Val Ala Ser Gly Gly Ile His Val Trp His Met
    370                 375                 380

ccc gca ctg gtg gaa atc ttc ggt gat gac tcc gtt ctc cag ttc ggt     1200
Pro Ala Leu Val Glu Ile Phe Gly Asp Asp Ser Val Leu Gln Phe Gly
385                 390                 395                 400

ggc ggc acc ttg ggt cac ccc tgg ggt aat gct cct ggt gca acc gcg     1248
Gly Gly Thr Leu Gly His Pro Trp Gly Asn Ala Pro Gly Ala Thr Ala
                405                 410                 415

aac cgt gtt gcc ttg gaa gct tgc gtc caa gct cgg aac gaa ggt cgc     1296
Asn Arg Val Ala Leu Glu Ala Cys Val Gln Ala Arg Asn Glu Gly Arg
            420                 425                 430

gac ctc tac cgt gaa ggc ggc gac atc ctt cgt gag gct ggc aag tgg     1344
Asp Leu Tyr Arg Glu Gly Gly Asp Ile Leu Arg Glu Ala Gly Lys Trp
        435                 440                 445

tcg cct gaa ctg gct gct gcc ctc gac ctc tgg aaa gag atc aag ttc     1392
Ser Pro Glu Leu Ala Ala Ala Leu Asp Leu Trp Lys Glu Ile Lys Phe
    450                 455                 460

gaa ttc gaa acg atg gac aag ctc taa ggagcctctg actatcgctg           1439
Glu Phe Glu Thr Met Asp Lys Leu  *
465                 470

agggagtgag cgttgctgcg taaagccttc tccccagcct ttcgacttaa cctttcagga   1499

tttctgaatc atg agc atg aaa act ctg ccc aaa gag cgt cgt ttc gag      1548
            Met Ser Met Lys Thr Leu Pro Lys Glu Arg Arg Phe Glu
                    475                 480                 485

act ttc tcg tac ctg cct ccc ctc agc gat cgc caa atc gct gca caa     1596
Thr Phe Ser Tyr Leu Pro Pro Leu Ser Asp Arg Gln Ile Ala Ala Gln
                490                 495                 500

atc gag tac atg atc gag caa ggc ttc cac ccc ttg atc gag ttc aac     1644
Ile Glu Tyr Met Ile Glu Gln Gly Phe His Pro Leu Ile Glu Phe Asn
            505                 510                 515

gag cac tcg aat ccg gaa gag ttc tac tgg acg atg tgg aag ctc ccc     1692
Glu His Ser Asn Pro Glu Glu Phe Tyr Trp Thr Met Trp Lys Leu Pro
        520                 525                 530

ctg ttt gac tgc aag agc cct cag caa gtc ctc gat gaa gtg cgt gag     1740
Leu Phe Asp Cys Lys Ser Pro Gln Gln Val Leu Asp Glu Val Arg Glu
    535                 540                 545

tgc cgc agc gaa tac ggt gat tgc tac atc cgt gtc gct ggc ttc gac     1788
Cys Arg Ser Glu Tyr Gly Asp Cys Tyr Ile Arg Val Ala Gly Phe Asp
550                 555                 560                 565

aac atc aag cag tgc caa acc gtg ggc ttc atc gtt cat cgt ccc ggc     1836
Asn Ile Lys Gln Cys Gln Thr Val Gly Phe Ile Val His Arg Pro Gly
                570                 575                 580

cgc tac taa                                                         1845
Arg Tyr  *
```

```
<210> SEQ ID NO 53
<211> LENGTH: 472
<212> TYPE: PRT
<213> ORGANISM: Artificial Sequence
<220> FEATURE:
<223> OTHER INFORMATION: F2B-3 rbcL

<400> SEQUENCE: 53
```

-continued

```
Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80

Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Thr Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
```

-continued

```
            420                 425                 430

Asp Leu Tyr Arg Glu Gly Gly Asp Ile Leu Arg Glu Ala Gly Lys Trp
        435                 440                 445

Ser Pro Glu Leu Ala Ala Ala Leu Asp Leu Trp Lys Glu Ile Lys Phe
    450                 455                 460

Glu Phe Glu Thr Met Asp Lys Leu
465                 470


<210> SEQ ID NO 54
<211> LENGTH: 111
<212> TYPE: PRT
<213> ORGANISM: Artificial Sequence
<220> FEATURE:
<223> OTHER INFORMATION: F2B-3 rbcS

<400> SEQUENCE: 54

Met Ser Met Lys Thr Leu Pro Lys Glu Arg Arg Phe Glu Thr Phe Ser
 1               5                  10                  15

Tyr Leu Pro Pro Leu Ser Asp Arg Gln Ile Ala Ala Gln Ile Glu Tyr
            20                  25                  30

Met Ile Glu Gln Gly Phe His Pro Leu Ile Glu Phe Asn Glu His Ser
        35                  40                  45

Asn Pro Glu Glu Phe Tyr Trp Thr Met Trp Lys Leu Pro Leu Phe Asp
    50                  55                  60

Cys Lys Ser Pro Gln Gln Val Leu Asp Glu Val Arg Glu Cys Arg Ser
65                  70                  75                  80

Glu Tyr Gly Asp Cys Tyr Ile Arg Val Ala Gly Phe Asp Asn Ile Lys
                85                  90                  95

Gln Cys Gln Thr Val Gly Phe Ile Val His Arg Pro Gly Arg Tyr
            100                 105                 110


<210> SEQ ID NO 55
<211> LENGTH: 1845
<212> TYPE: DNA
<213> ORGANISM: Artificial Sequence
<220> FEATURE:
<223> OTHER INFORMATION: Codon Optimized F2A-10, rbcLS
<220> FEATURE:
<221> NAME/KEY: CDS
<222> LOCATION: (1)...(1419)
<223> OTHER INFORMATION: Codon Optimized F2A-10, rbcL
<220> FEATURE:
<221> NAME/KEY: CDS
<222> LOCATION: (1510)...(1845)
<223> OTHER INFORMATION: Codon Optimized F2A-10, rbcS

<400> SEQUENCE: 55

atg ccg aag act caa agc gcg gcg ggc tac aag gcc ggc gtt aaa gat       48
Met Pro Lys Thr Gln Ser Ala Ala Gly Tyr Lys Ala Gly Val Lys Asp
 1               5                  10                  15

tac aag ttg act tat tat acc ccg gat tac act ccc aaa gac acg gac       96
Tyr Lys Leu Thr Tyr Tyr Thr Pro Asp Tyr Thr Pro Lys Asp Thr Asp
            20                  25                  30

ttg ctc gcc gca ttc cgc ttc agc cca caa ccc gga gtt cct gct gat      144
Leu Leu Ala Ala Phe Arg Phe Ser Pro Gln Pro Gly Val Pro Ala Asp
        35                  40                  45

gag gcg ggt gcc gcc atc gcg gca gag agt agt acc ggc acg tgg act      192
Glu Ala Gly Ala Ala Ile Ala Ala Glu Ser Ser Thr Gly Thr Trp Thr
     50                  55                  60

act gtg tgg act gat ctg ttg acc gat atg gac cgc tac aaa ggg aaa      240
Thr Val Trp Thr Asp Leu Leu Thr Asp Met Asp Arg Tyr Lys Gly Lys
 65                  70                  75                  80
```

-continued

```
tgc tac cat atc gaa ccc gtg cag ggc gaa gag aac tca tat ttt gcc      288
Cys Tyr His Ile Glu Pro Val Gln Gly Glu Glu Asn Ser Tyr Phe Ala
                 85                  90                  95

ttt ata gca tat ccg tta gat tta ttc gaa gaa gga tct gtt acc aac      336
Phe Ile Ala Tyr Pro Leu Asp Leu Phe Glu Glu Gly Ser Val Thr Asn
            100                 105                 110

att ctc act tcg atc gtc ggt aat gta ttt ggc ttc aag gcc att cga      384
Ile Leu Thr Ser Ile Val Gly Asn Val Phe Gly Phe Lys Ala Ile Arg
        115                 120                 125

agt cta agg ttg gaa gat atc cgc ttt ccg gtg gct ttg gtg aag act      432
Ser Leu Arg Leu Glu Asp Ile Arg Phe Pro Val Ala Leu Val Lys Thr
    130                 135                 140

ttt cag ggc ccg ccg cat gga ata caa gtt gaa cgt gat ctc ttg aat      480
Phe Gln Gly Pro Pro His Gly Ile Gln Val Glu Arg Asp Leu Leu Asn
145                 150                 155                 160

aag tac ggc cgt ccc atg ctc gga tgc aca att aag ccg aaa tta ggg      528
Lys Tyr Gly Arg Pro Met Leu Gly Cys Thr Ile Lys Pro Lys Leu Gly
                165                 170                 175

ctg tcc gcc aag aac tac gga cga gct gtt tat gag tgt tta cgg ggg      576
Leu Ser Ala Lys Asn Tyr Gly Arg Ala Val Tyr Glu Cys Leu Arg Gly
            180                 185                 190

gga ctg gac ttc act aag gat gac gag aat atc aac agc caa cca ttc      624
Gly Leu Asp Phe Thr Lys Asp Asp Glu Asn Ile Asn Ser Gln Pro Phe
        195                 200                 205

caa cgc tgg cgc gat cga ttt ttg ttc gtg gcc gac gca atc cac aaa      672
Gln Arg Trp Arg Asp Arg Phe Leu Phe Val Ala Asp Ala Ile His Lys
    210                 215                 220

tca cag gct gaa act ggc gag ata aag ggg cac tac tta aat gtt acc      720
Ser Gln Ala Glu Thr Gly Glu Ile Lys Gly His Tyr Leu Asn Val Thr
225                 230                 235                 240

gct ccc acc tgt gaa gaa atg atg aag cgc gcc gaa ttt gcg aaa gaa      768
Ala Pro Thr Cys Glu Glu Met Met Lys Arg Ala Glu Phe Ala Lys Glu
                245                 250                 255

tta ggg atg cca atc ata atg cat gat ttt ctt act gcc ggt ttt act      816
Leu Gly Met Pro Ile Ile Met His Asp Phe Leu Thr Ala Gly Phe Thr
            260                 265                 270

gcc aat acg acc tta gcc aaa tgg tgc cga gac aac ggc gtg ctg ctg      864
Ala Asn Thr Thr Leu Ala Lys Trp Cys Arg Asp Asn Gly Val Leu Leu
        275                 280                 285

cat att cat cgt gct atg cac gca gta att gat aga caa cgg aac cat      912
His Ile His Arg Ala Met His Ala Val Ile Asp Arg Gln Arg Asn His
    290                 295                 300

gga att cat ttt aga gtg ctc gca aag tgt tta cgc ttg agt ggt gga      960
Gly Ile His Phe Arg Val Leu Ala Lys Cys Leu Arg Leu Ser Gly Gly
305                 310                 315                 320

gat cat ttg cac agc ggg act gtc gtg ggc aag ttg gaa ggc gat aaa     1008
Asp His Leu His Ser Gly Thr Val Val Gly Lys Leu Glu Gly Asp Lys
                325                 330                 335

gcg agt act ttg ggc ttt gtt gac tta atg cgt gag gat cat att gaa     1056
Ala Ser Thr Leu Gly Phe Val Asp Leu Met Arg Glu Asp His Ile Glu
            340                 345                 350

gcg gac cgt tct cgg ggc gta ttc ttt act caa gac tgg gct agt atg     1104
Ala Asp Arg Ser Arg Gly Val Phe Phe Thr Gln Asp Trp Ala Ser Met
        355                 360                 365

cca ggg gtc cta ccc gtg gct tcc ggg ggc atc cac gta tgg cat atg     1152
Pro Gly Val Leu Pro Val Ala Ser Gly Gly Ile His Val Trp His Met
    370                 375                 380

ccg gcg ttg gtg gaa att ttt ggc gac gat agt gtg ttg caa ttt ggt     1200
Pro Ala Leu Val Glu Ile Phe Gly Asp Asp Ser Val Leu Gln Phe Gly
```

-continued

```
385                 390                 395                 400

ggt ggg acc ctg ggt cac ccg tgg ggc aat gca ccg ggg gcc act gcc      1248
Gly Gly Thr Leu Gly His Pro Trp Gly Asn Ala Pro Gly Ala Thr Ala
                405                 410                 415

aac cgt gtg gct ctt gaa gcc tgc gtc cag gca aga aat gaa ggg agg      1296
Asn Arg Val Ala Leu Glu Ala Cys Val Gln Ala Arg Asn Glu Gly Arg
            420                 425                 430

gat tta tat cga gaa ggg ggg gat att ctg cgt gaa gct ggt aaa tgg      1344
Asp Leu Tyr Arg Glu Gly Gly Asp Ile Leu Arg Glu Ala Gly Lys Trp
        435                 440                 445

agc ccc gaa ttg gct att gct tta gat cta tgg aag gaa att aag ttt      1392
Ser Pro Glu Leu Ala Ile Ala Leu Asp Leu Trp Lys Glu Ile Lys Phe
    450                 455                 460

gag ttt gag acc atg gat aag cta taa ggagcctctg actatcgctg           1439
Glu Phe Glu Thr Met Asp Lys Leu  *
465                 470

ggggagtgag cgttgctgcg taaagctttc tccccagcct ttcgacttaa cctttcagga   1499

tttctgaatc atg tcc atg aaa acc ttg ccc aaa gaa cgg cgg ttt gaa      1548
            Met Ser Met Lys Thr Leu Pro Lys Glu Arg Arg Phe Glu
                    475                 480                 485

acc ttt tcc tat ttg ccc ccc ttg tcc gat cgg caa att gcc gcc caa      1596
Thr Phe Ser Tyr Leu Pro Pro Leu Ser Asp Arg Gln Ile Ala Ala Gln
                490                 495                 500

att gaa tat atg att gaa caa ggc ttt cat ccc ttg att gaa ttt aat      1644
Ile Glu Tyr Met Ile Glu Gln Gly Phe His Pro Leu Ile Glu Phe Asn
            505                 510                 515

gaa cat tcc aat ccc gaa gaa ttt tat tgg acc atg tgg aaa ttg ccc      1692
Glu His Ser Asn Pro Glu Glu Phe Tyr Trp Thr Met Trp Lys Leu Pro
        520                 525                 530

ttg ttt gat tgt aaa tcc ccc caa caa gtg ttg gat gaa gtg cgg gaa      1740
Leu Phe Asp Cys Lys Ser Pro Gln Gln Val Leu Asp Glu Val Arg Glu
    535                 540                 545

tgt cgg tcc gaa tat ggc gat tgt tat att cgg gtg gcc ggc ttt gat      1788
Cys Arg Ser Glu Tyr Gly Asp Cys Tyr Ile Arg Val Ala Gly Phe Asp
550                 555                 560                 565

aat att aaa caa tgt caa acc gtg tcc ttt att gtg cat cgg ccc ggc      1836
Asn Ile Lys Gln Cys Gln Thr Val Ser Phe Ile Val His Arg Pro Gly
                570                 575                 580

cgg tat taa                                                           1845
Arg Tyr  *


<210> SEQ ID NO 56
<211> LENGTH: 472
<212> TYPE: PRT
<213> ORGANISM: Artificial Sequence
<220> FEATURE:
<223> OTHER INFORMATION: F2A-10 rbcL

<400> SEQUENCE: 56

Met Pro Lys Thr Gln Ser Ala Ala Gly Tyr Lys Ala Gly Val Lys Asp
 1               5                  10                  15

Tyr Lys Leu Thr Tyr Tyr Thr Pro Asp Tyr Thr Pro Lys Asp Thr Asp
            20                  25                  30

Leu Leu Ala Ala Phe Arg Phe Ser Pro Gln Pro Gly Val Pro Ala Asp
        35                  40                  45

Glu Ala Gly Ala Ala Ile Ala Ala Glu Ser Ser Thr Gly Thr Trp Thr
    50                  55                  60

Thr Val Trp Thr Asp Leu Leu Thr Asp Met Asp Arg Tyr Lys Gly Lys
65                  70                  75                  80
```

-continued

```
Cys Tyr His Ile Glu Pro Val Gln Gly Glu Glu Asn Ser Tyr Phe Ala
                85                  90                  95

Phe Ile Ala Tyr Pro Leu Asp Leu Phe Glu Glu Gly Ser Val Thr Asn
            100                 105                 110

Ile Leu Thr Ser Ile Val Gly Asn Val Phe Gly Phe Lys Ala Ile Arg
        115                 120                 125

Ser Leu Arg Leu Glu Asp Ile Arg Phe Pro Val Ala Leu Val Lys Thr
    130                 135                 140

Phe Gln Gly Pro Pro His Gly Ile Gln Val Glu Arg Asp Leu Leu Asn
145                 150                 155                 160

Lys Tyr Gly Arg Pro Met Leu Gly Cys Thr Ile Lys Pro Lys Leu Gly
                165                 170                 175

Leu Ser Ala Lys Asn Tyr Gly Arg Ala Val Tyr Glu Cys Leu Arg Gly
            180                 185                 190

Gly Leu Asp Phe Thr Lys Asp Asp Glu Asn Ile Asn Ser Gln Pro Phe
        195                 200                 205

Gln Arg Trp Arg Asp Arg Phe Leu Phe Val Ala Asp Ala Ile His Lys
    210                 215                 220

Ser Gln Ala Glu Thr Gly Glu Ile Lys Gly His Tyr Leu Asn Val Thr
225                 230                 235                 240

Ala Pro Thr Cys Glu Glu Met Met Lys Arg Ala Glu Phe Ala Lys Glu
                245                 250                 255

Leu Gly Met Pro Ile Ile Met His Asp Phe Leu Thr Ala Gly Phe Thr
            260                 265                 270

Ala Asn Thr Thr Leu Ala Lys Trp Cys Arg Asp Asn Gly Val Leu Leu
        275                 280                 285

His Ile His Arg Ala Met His Ala Val Ile Asp Arg Gln Arg Asn His
    290                 295                 300

Gly Ile His Phe Arg Val Leu Ala Lys Cys Leu Arg Leu Ser Gly Gly
305                 310                 315                 320

Asp His Leu His Ser Gly Thr Val Val Gly Lys Leu Glu Gly Asp Lys
                325                 330                 335

Ala Ser Thr Leu Gly Phe Val Asp Leu Met Arg Glu Asp His Ile Glu
            340                 345                 350

Ala Asp Arg Ser Arg Gly Val Phe Phe Thr Gln Asp Trp Ala Ser Met
        355                 360                 365

Pro Gly Val Leu Pro Val Ala Ser Gly Gly Ile His Val Trp His Met
    370                 375                 380

Pro Ala Leu Val Glu Ile Phe Gly Asp Asp Ser Val Leu Gln Phe Gly
385                 390                 395                 400

Gly Gly Thr Leu Gly His Pro Trp Gly Asn Ala Pro Gly Ala Thr Ala
                405                 410                 415

Asn Arg Val Ala Leu Glu Ala Cys Val Gln Ala Arg Asn Glu Gly Arg
            420                 425                 430

Asp Leu Tyr Arg Glu Gly Gly Asp Ile Leu Arg Glu Ala Gly Lys Trp
        435                 440                 445

Ser Pro Glu Leu Ala Ile Ala Leu Asp Leu Trp Lys Glu Ile Lys Phe
    450                 455                 460

Glu Phe Glu Thr Met Asp Lys Leu
465                 470
```

<210> SEQ ID NO 57
<211> LENGTH: 111

-continued

<212> TYPE: PRT
<213> ORGANISM: Artificial Sequence
<220> FEATURE:
<223> OTHER INFORMATION: F2A-10 rbcS

<400> SEQUENCE: 57

Met Ser Met Lys Thr Leu Pro Lys Glu Arg Arg Phe Glu Thr Phe Ser
1 5 10 15

Tyr Leu Pro Pro Leu Ser Asp Arg Gln Ile Ala Ala Gln Ile Glu Tyr
20 25 30

Met Ile Glu Gln Gly Phe His Pro Leu Ile Glu Phe Asn Glu His Ser
35 40 45

Asn Pro Glu Glu Phe Tyr Trp Thr Met Trp Lys Leu Pro Leu Phe Asp
50 55 60

Cys Lys Ser Pro Gln Gln Val Leu Asp Glu Val Arg Glu Cys Arg Ser
65 70 75 80

Glu Tyr Gly Asp Cys Tyr Ile Arg Val Ala Gly Phe Asp Asn Ile Lys
85 90 95

Gln Cys Gln Thr Val Ser Phe Ile Val His Arg Pro Gly Arg Tyr
100 105 110

<210> SEQ ID NO 58
<211> LENGTH: 2354
<212> TYPE: DNA
<213> ORGANISM: Synechocystis sp. PCC6803
<220> FEATURE:
<221> NAME/KEY: misc_feature
<222> LOCATION: (1)...(2354)
<223> OTHER INFORMATION: 5' sequence flanking rbcLS for vector pGR-2a

<400> SEQUENCE: 58
aaatcgacgc gtgttaccag attgcctaaa cccttagctc ccgtgggggc caaccttttt 60
tagattggca attgcgctat ctacaacagc agggttttcg gcgatcgctc ctttctacgg 120
gttatctggc agaaaaagtg gcggcctatg ctcaagatgc cgatattgtt gacatggcga 180
tcgcctgtgt ggcggaaatg gaaccgttgg gaacagcggg gggatttgtc aatgcggtta 240
atcaccatgg ttttagagaa ctaacaccgg cttggctcgt gcttaacggc gactcgttaa 300
ttgtgacgga ttatcgggtt ctgttggcgg agttagagga tgacagcgtt gatggggtaa 360
ttttgggcgt tcatgtgccc gatgcttccc gttttggctc cttaaaggtt aatagtcaag 420
gggaattgct acaatttgca gaaaagcaag ccggagccgg cgtgattaat agtggggttt 480
atctccttgg cgatcgcctg ttggcccggt ttcccgccca cagaccctta agttttgagt 540
atgatgtgtt ccccacattg ttggcccagg gagccaaaat caaagtccat gctgtggaag 600
ctcccttttt agatattggc accccggaaa cattagccca ggcgggggaa tttatccaat 660
ccctcggtac gttgaaccga attcaagacc tagacaaata gcttaaaatg agaagctaac 720
tgagaaatta actaagtttt gtaaattttg gtttgcgggg gcgagcgtca cgatgggtaa 780
acggacaagg cggttttggg ctttagcttt ttctttgctg atgggggccc tgatttatct 840
gggcaataca ccgtcggcct tggctttcac cgaggaacaa aagctactgt tgcaatcctg 900
gcgtttggtc aaccaatcct atctcgatga aacctttaac catcaaaatt ggtggctgtt 960
gcgggagaag tacgttaaac gtcccctccg gaaccgggaa gaaacctaca cggcgatcga 1020
agaaatgctc gctaccctgg atgaaccctt tacccgctta ctgcgtccgg aacagtacgg 1080
caatctccag gtgaccacca ctggtgagct atcgggggta ggtctgcaaa tcaacatcaa 1140
ccctgaaacc aaccagttag aaattatggc ccccctggcc ggttcccctg cggaggaggc 1200

-continued cgggctgcaa ccccatgacc aaattttggc gatcgacggt gtagataccc aaaccctgag 1260
cttagacgaa gcagcggcca gaatgcgggg cccaaaaaac accaaagttt ccctggaaat 1320
tctgtcagcg ggcaccgaag taccccaaga atttaccctg actcggcagt taatttccct 1380
cagtccggtg gcggcccaat tggacgattc ccgcccaggt caatcggtgg gttacattcg 1440
cctcagtcaa tttagtgcca atgcctataa agaagtagcc cacgctctgc atcaacttga 1500
ggaacagggg gccgacggtt atatcttgga tttgcgtaac aaccccggtg gcttactcca 1560
ggctggtatt gacattgctc ggttgtggtt accggaaagc accattgtct acaccgttaa 1620
tcgccaaggc acccaggaaa gtttcactgc caatggagaa gcggcgaccg atcgcccgtt 1680
ggtggtgttg gtcaaccagg gtactgccag tgccagcgaa attttagccg gagctttgca 1740
ggataatcag cgggccactc tagtggggga aaaaaccttt ggtaagggtt tgattcaatc 1800
cttgtttgaa ctatccgatg ggccggcat tgccgtcacg gtggccaaat acgaaacccc 1860
ccaacatcac gacatccata aactgggcat tatgcccgat gaagtggtgg agcaacccct 1920
gattagcttt gcggaaatta cttcccccgc cgatgtgcaa taccaagccg ccttagattt 1980
gctcaccgga ggagtggcaa tcgcccataa atcttcttca attcccgcca tggcaacggc 2040
tcacaagccc aactaatcac catttggaca aaacatcagg aattctaatt agaaagtcca 2100
aaaattgtaa tttaaaaaac agtcaatgga gagcattgcc ataagtaaag gcatcccctg 2160
cgtgataaga ttaccttcag aaaacagata gttgctgggt tatcgcagat ttttctcgca 2220
accaaataac tgtaaataat aactgtctct ggggcgacgg taggctttat attgccaaat 2280
ttcgcccgtg ggagaaagct aggctattca atgtttatgg aggactgatc tagacctgac 2340
caccgtacgt cagg 2354

<210> SEQ ID NO 59
<211> LENGTH: 2251
<212> TYPE: DNA
<213> ORGANISM: Synechocystis sp. PCC6803
<220> FEATURE:
<221> NAME/KEY: misc_feature
<222> LOCATION: (1)...(2251)
<223> OTHER INFORMATION: 3' sequence flanking rbcLS for vector pGR-2a

<400> SEQUENCE: 59
gagctcgttg gtaaattgga aggggaacgg ggtatcacca tgggcttcgt tgacctcatg 60
cgcgaagatt acgttgagga agatcgctcc cggggtattt tcttcaccca agactatgcc 120
tccatgcctg gcaccatgcc cgtagcttcc ggtggtatcc acgtatggca catgcccgcg 180
ttggtggaaa tcttcggtga tgattcctgc ttacagtttg gtggtggtac tttgggtcac 240
ccctggggta atgctcccgg tgcaaccgct aaccgtgttg ctttggaagc ttgtgttcaa 300
gctcggaacg aaggtcgtaa cctggctcgc gaaggtaatg acgttatccg ggaagcctgt 360
cgttggtccc ctgagttggc cgccgcctgc gaactctgga aagagatcaa gtttgagttc 420
gaggccatgg ataccctcta aaccggtgtt tggattgtcg gagttgtact cgtccgttaa 480
ggatgaacag ttcttcgggg ttgagtctgc taactaatta gccattaaca gcggcttaac 540
taacagttag tcattggcaa ttgtcaaaaa attgttaatc agccaaaacc cactgcttac 600
tgatgttcaa cttcgacagc aatttaccaa ttaccgggta gagtgttcat gcaaactaag 660
cacatagctc aggcaacagt gaaagtactg caaagttacc tcacctacca agccgttctc 720
aggatccaga gtgaactcgg ggaaaccaac cctccccagg ccatttggtt aaaccagtat 780

-continued

```
ttagccagtc acagtattca aaatggagaa acgtttttga cggaactcct ggatgaaaat    840

aaagaactgg tactcaggat cctggcggta agggaagaca ttgccgaatc agtgttagat    900

tttttgcccg gtatgacccg gaatagctta gcggaatcta acatcgccca ccgccgccat    960

ttgcttgaac gtctgacccg taccgtagcc gaagtcgata atttcccttc ggaaacctcc   1020

aacggagaat caaacaacaa cgattctccc ccgtcctaac gtagtcatca gcaaggaaaa   1080

cttttaaatc gatgaaaact ttacccaaag agcgccgcta cgaaaccctt tcttacctgc   1140

cccctttaac cgatcaacag attgctaaac aggttgagtt tctgttagac cagggcttta   1200

ttcccggcgt ggaatttgaa gaagaccccc aacccgaaac ccacttctgg accatgtgga   1260

aactgccctt ctttggtggt gccactgcca acgaagttct agccgaagta cgggaatgtc   1320

gttctgagaa tcccaactgc tacattcggg tgattggttt cgacaatatc aaacagtgcc   1380

agactgtaag ctttattgtc cacaaaccca accaaaacca aggccgttac taagttacag   1440

ttttggcaat tactaaaaaa ctgacttcaa ttcaatgtta gcccgctccc gcgggttttt   1500

tgttgctttt tcacagtgac tataggtaat cagcaacaca atacggccct gttctttgga   1560

cagtttttgt ataatgttga ccgcatcctg accggatttt ttatctaagt ggggaattgt   1620

caattgtcaa ttaaagctaa gttctactaa tgttttagaa ggcattgtcg attgaaaata   1680

agggttgaat ggagaaaatt ttgagccttt gtcaaagata aaaatttatt tcaacagttt   1740

tttaactagc cgaaccagag aatgacccag tggcgctgac tttgctcccg agtttttgtt   1800

agaaattacc ctcaagaagt aatctaataa taaacctaac cgaataattt cccaggggag   1860

tattccggaa aaccatggtt aaacttactt gccatccccc atggtaaaat tgcaacgatt   1920

ttgatcaaag tcctaatttt tttgtaaagc ttttagtaat ccttctgatt ttcccatgaa   1980

gctcatcgat tcccgtggca gaattttcgg catagtcagc ctgttggatc tgggggccgc   2040

cttgatcatc ctcatggtag ctgtgggaat tttcgttctg ccgggcagtt ctggcaaaag   2100

cattcttgcc caagccaacg ccgcttccat tgaattgacg accattgtcc ggggattaaa   2160

cgtattagat ccccaggtgg tgctggatga gtttaaagcc gaaaaaacca acatcattat   2220

tcgcaatcaa ccggctggcc agggcggccg c                                  2251
```

<210> SEQ ID NO 60
<211> LENGTH: 1594
<212> TYPE: DNA
<213> ORGANISM: Synechocystis sp. PCC 6803
<220> FEATURE:
<221> NAME/KEY: misc_feature
<222> LOCATION: (1)...(1594)
<223> OTHER INFORMATION: 5' sequence flanking rbcLS for vector pGR-2b

<400> SEQUENCE: 60

```
tttcgcgtta cgcgtgtaaa cggacaaggc ggttttgggc tttagctttt tctttgctga     60

tgggggccct gatttatctg ggcaatacac cgtcggcctt ggctttcacc gaggaacaaa    120

agctactgtt gcaatcctgg cgtttggtca accaatccta tctcgatgaa acctttaacc    180

atcaaaattg gtggctgttg cgggagaagt acgttaaacg tcccctccgg aaccgggaag    240

aaacctacac ggcgatcgaa gaaatgctcg ctaccctgga tgaacccttt acccgcttac    300

tgcgtccgga acagtacggc aatctccagg tgaccaccac tggtgagcta tcgggggtag    360

gtctgcaaat caacatcaac cctgaaacca accagttaga aattatggcc cccctggccg    420

gttcccctgc ggaggaggcc gggctgcaac cccatgacca aattttggcg atcgacggtg    480

tagataccca aaccctgagc ttagacgaag cagcggccag aatgcggggc ccaaaaaaca    540
```

-continued

```
ccaaagtttc cctggaaatt ctgtcagcgg gcaccgaagt accccaagaa tttaccctga    600
ctcggcagtt aatttccctc agtccggtgg cggcccaatt ggacgattcc cgcccaggtc    660
aatcggtggg ttacattcgc ctcagtcaat ttagtgccaa tgcctataaa gaagtagccc    720
acgctctgca tcaacttgag gaacaggggg ccgacggtta tatcttggat ttgcgtaaca    780
accccggtgg cttactccag gctggtattg acattgctcg gttgtggtta ccggaaagca    840
ccattgtcta caccgttaat cgccaaggca cccaggaaag tttcactgcc aatggagaag    900
cggcgaccga tcgcccgttg gtggtgttgg tcaaccaggg tactgccagt gccagcgaaa    960
ttttagccgg agctttgcag gataatcagc gggccactct agtgggggaa aaaacctttg   1020
gtaagggttt gattcaatcc ttgtttgaac tatccgatgg ggccggcatt gccgtcacgg   1080
tggccaaata cgaaaccccc caacatcacg acatccataa actgggcatt atgcccgatg   1140
aagtggtgga gcaacccctg attagctttg cggaaattac ttcccccgcc gatgtgcaat   1200
accaagccgc cttagatttg ctcaccggag gagtggcaat cgcccataaa tcttcttcaa   1260
ttcccgccat ggcaacggct cacaagccca actaatcacc atttggacaa aacatcagga   1320
attctaatta gaaagtccaa aaattgtaat ttaaaaaaca gtcaatggag agcattgcca   1380
taagtaaagg catcccctgc gtgataagat taccttcaga aaacagatag ttgctgggtt   1440
atcgcagatt tttctcgcaa ccaaataact gtaaataata actgtctctg ggcgacggt    1500
aggctttata ttgccaaatt tcgcccgtgg gagaaagcta ggctattcaa tgtttatgga   1560
ggactgatct agatggtaca aagccaaagc aggg                               1594
```

<210> SEQ ID NO 61
<211> LENGTH: 1624
<212> TYPE: DNA
<213> ORGANISM: Synechocystis sp. PCC6803
<220> FEATURE:
<221> NAME/KEY: misc_feature
<222> LOCATION: (1)...(1624)
<223> OTHER INFORMATION: 3' sequence flanking rbcLS for vector pGR-3a

<400> SEQUENCE: 61

```
accttagagc tcataatgtt gaccgcatcc tgaccggatt ttttatctaa gtggggaatt     60
gtcaattgtc aattaaagct aagttctact aatgttttag aaggcattgt cgattgaaaa    120
taagggttga atggagaaaa ttttgagcct ttgtcaaaga taaaaattta tttcaacagt    180
tttttaacta gccgaaccag agaatgaccc agtggcgctg actttgctcc cgagtttttg    240
ttagaaatta ccctcaagaa gtaatctaat aataaaccta accgaataat ttcccagggg    300
agtattccgg aaaaccatgg ttaaacttac ttgccatccc ccatggtaaa attgcaacga    360
ttttgatcaa agtcctaatt tttttgtaaa gcttttagta atccttctga ttttcccatg    420
aagctcatcg attcccgtgg cagaattttc ggcatagtca gcctgttgga tctgggggcc    480
gccttgatca tcctcatggt agctgtggga attttcgttc tgccgggcag ttctggcaaa    540
agcattcttg cccaagccaa cgccgcttcc attgaattga cgaccattgt ccggggatta    600
aacgtattag atccccaggt ggtgctggat gagtttaaag ccgaaaaaac caacatcatt    660
attcgcaatc aaccggctgg ccaggtggag gtagtgaatg tgcaggaact ccctcgcaat    720
ttagcagtgc cccagcctga tggttccgtc aaatctctgc cggatcctcg gccagagtct    780
aattacagcc gggatatgct cctgaccctc aaaggtaggg gggatttcac ctccaccggc    840
atggttttag ggggacaaaa ggtgaaaatt ggcacggttt tagaattaga aggcaaaaac    900
```

-continued

| | |
|---|---|
| tataacttca atgccagtgt ggtgggcatc aatcaaccaa agtgaccaaa gtattagatt | 960 |
| agtccggccc ccgagaattg ctgttggctg cccaaagttt tgctgtaccc tgggtaaggc | 1020 |
| tgacagattt ggaaaaggta atggaatgga acgagagtct tctccggctc actgttgctt | 1080 |
| ttgtactggg atcgaccctg ggcattgaac ggcagtggcg ccaacggatg gcgggcttgc | 1140 |
| gtactaatac cttggtggcc attggagctg cattgtttgt gattgtttct gtcctcacca | 1200 |
| atcatgacag cagtcccacc cgaattcctg cccaaattgt ctccggcatt ggttttctgg | 1260 |
| cggggggagt aattctcaag gaaggcttaa ctgttaaggg gctaaatacg gcggcgaccc | 1320 |
| tctggtgttc agcggcggtg ggcaccctct gtggtcaagg gctgttttct gaggctgtgc | 1380 |
| ttggctcgat gatggttttg gtggccaaca ttgccctgcg gcctctgagc acgtttatta | 1440 |
| accaccaacc catgcatagc actgaattgg agtgccatta tctttgtcac ttggtatgtc | 1500 |
| ggggggatga ggaggcgaat gtgcgacgca ttttgcttga ttccttagcg gaaataaaga | 1560 |
| atattaaatt acggtctttg cggagccatg atttagatga gtttaacctg cggccgcttc | 1620 |
| cctt | 1624 |

RIBULOSE 1,5-BISPHOSPHATE CARBOXYLASE/OXYGENASE POLYPEPTIDES AND RELATED POLYNUCLEOTIDES

CROSS-REFERENCE TO RELATED APPLICATIONS

This application claims the benefit under 35 U.S.C. § 119(e) of U.S. Ser. No. 60/375,910, filed Apr. 26, 2002, which is incorporated herein in its entirety.

COPYRIGHT NOTIFICATION

A portion of the disclosure of this patent document contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

The present invention relates to novel ribulose-1,5-bisphosphate carboxylase/oxygenase polypeptides and the polynucleotides that encode them.

BACKGROUND OF THE INVENTION

Carbon fixation, or the conversion of $CO_2$ to reduced forms amenable to cellular biochemistry, occurs by several metabolic pathways in diverse organisms. The most familiar of these is the Calvin Cycle (or "Calvin-Benson" cycle), which is present in cyanobacteria and their plastid derivatives (i.e., chloroplasts), as well as in proteobacteria. The Calvin cycle in these organisms utilizes the enzyme, ribulose-1,5-bisphosphate carboxylate/oxygenase ("Rubisco"). See, e.g., the world wide web at blc.Arizona.edu/courses/181gh/rick/photosynthesis/Calvin.html; Raven, et al. (1981) *The Biology of Plants*, $3^{rd}$ Edition, Worth Publishers, Inc., NY, N.Y. Rubisco exists in at least two forms: Form I Rubisco, which is found in proteobacteria, cyanobacteria, and plastids; and Form II Rubisco, which is found in proteobacteria. Form I Rubisco is encoded by two genes encoding large and small subunits (rbcL and rbcS), and may exist as an octo-dimer composed of eight large subunits (rbcL) and eight small subunits (rbcS). Form II Rubisco is a dimeric form of the enzyme. Form II Rubisco has clear similarities to the large subunit of Form I Rubisco, and is encoded by a single gene, also referred to as rbcL. The evolutionary origin of the small subunit of Form I Rubisco remains uncertain; it is less highly conserved than the large subunit, and may have cryptic homology to a portion of the Form II protein.

All photosynthetic organisms catalyze the fixation of atmospheric $CO_2$ by the bifunctional enzyme Rubisco. Significant variations in kinetic properties of this enzyme are found among various phylogenetic groups. Because of the abundance and fundamental importance of Rubisco, the enzyme has been extensively studied. Well over 1,000 different Rubisco homologues are available in the public literature and the crystal structure of Rubisco has been solved for several variants of the protein.

Rubisco contains two competing enzymatic activities: an oxygenase and a carboxylase activity. The oxygenation reaction catalyzed by Rubisco is considered a "wasteful" process because it competes with, and significantly reduces the net amount of carbon fixed by an organism. The Rubisco enzyme species encoded in various photosynthetic organisms have been selected by natural evolution to provide higher plants with a Rubisco enzyme that is substantially more efficient at carboxylation in the presence of atmospheric oxygen.

The creation of plants and other photosynthetic organisms having improved Rubisco biosynthetic pathways can provide increased yields of certain types of foodstuffs, enhanced biomass energy sources, and may alter the types and amounts of nutrients present in certain foodstuffs, among other desirable phenotypes. The development of technologies for effective biological fixation of $CO_2$ on a global scale can mitigate the effects of atmospheric greenhouse gas emission. Cyanobacterial aquaculture ("cyanofarming") offers one of the most productive solutions for global greenhouse gas control, as compared to other biological alternatives aimed at $CO_2$ abatement technology for global use. However, it would be desirable to improve biomass productivity of cyanofarming by 10 to 20 fold over current production levels. Thus, a need exists for improved Rubisco enzymes.

BRIEF SUMMARY OF THE INVENTION

The present invention provides novel ribulose 1,5-bisphosphate carboxylase/oxygenase ("Rubisco") polypeptides, including the large and small subunits. In particular, the present invention provides an isolated or recombinant Rubisco large subunit polypeptide comprising an amino acid sequence selected from the group consisting of:

(a) an amino acid sequence that is at least 99% identical to SEQ ID NO: 5;

(b) an amino acid sequence that is at least 95% identical to SEQ ID NO: 8;

(c) an amino acid sequence that is at least 97% identical to SEQ ID NO: 35; and (d) an amino acid sequence that is at least 99% identical to SEQ ID NO: 11.

Specific Rubisco large subunit polypeptides of the present invention comprise an amino acid sequence selected from the group consisting of SEQ ID NO: 5, SEQ ID NO: 8, SEQ ID NO: 1, SEQ ID NO: 14, SEQ ID NO: 20, SEQ ID NO: 29, SEQ ID NO: 32, SEQ ID NO: 35, SEQ ID NO: 38, SEQ ID NO: 41, SEQ ID NO: 47, SEQ ID NO: 50, and SEQ ID NO: 53.

Certain large subunit Rubisco polynucleotides encode large subunit Rubisco polypeptides having at least one amino residue from the set of (a)-(bd) residues listed below. The amino acid residue positions refer to the position in the encoded amino acid sequence when it is optimally aligned with reference sequence SEQ ID NO: 5, 8, 35, or 11. The present invention further provides Rubisco large subunit polypeptides that have at least one amino acid residue selected from the group consisting of: : (a) V at position 84; (b) D at position 92; (c) F at position 93; (d) L at position 113; (e) L at position 116; (f) L at position 117; (g) L at position 127; (h) A at position 129; (i) V at position 137; (j) I at position 139; (k) Y at position 141; (l) L at position 142; (m) S at position 149; (n) G at position 154; (o) K at position 158; (p) L at position 166; (q) M at position 209; (r) Q at position 219; (s) E at position 220; (t) E at position 223; (u) A at psition 225 (v) T at position 232; (w) Q at position 246; (x) E at position 249; (y) A at position 252; (z) I at position 257; (aa)T at position 259; (ab) G at position 269; (ac) S at postion 276; (ad) Y at position 280; (ae) L at position 286; (af) A at position 297; (ag) K at position 303; (ah) T at position 304; (ai) M at position 317; (aj) Q at position 322; (ak) T at position 325; (al) R at position 336; (am) Q at position 337; (an) T at position 338; (ao) I at position 343; (ap) Q at position 345; (aq) L at position 346; (ar) S at position 349; (as) F at position 350; (at)P at position 352; (au) E at position 353; (av) N or T at position 356; (aw) N at position 359; (ax) D at position 362; (ay) G at position 366; (az) F at position 372; (ba) A at position 373; (bb) A at position 389; (bc) I at position 415; (bd) R at position 450; and (be) I at position 454.

The present invention also provides Rubisco small subunit polypeptides that comprise an amino acid sequence corresponding to SEQ ID NO: 3 and having one or more substitutions selected from the group consisting of: (a) D23N; (b) M33T; (c) K66N; (d) S67G; (e) S102G; and (f) P108S. The present invention provides specific Rubisco small subunit polypeptides selected from the group consisting of: SEQ ID NO: 12, SEQ ID NO: 18, SEQ ID NO: 24, SEQ ID NO: 27, SEQ ID NO: 30, SEQ ID NO: 39, SEQ ID NO: 45, SEQ ID NO: 48, and SEQ ID NO: 54.

The present invention further provides Rubisco polypeptides having both large and small subunits and that exhibit ribulose 1,5-bisphosphate carboxylase/oxygenase ("Rubisco") activity, wherein the polypeptide comprises a large subunit and a small subunit, wherein the large subunit comprises an amino acid sequence selected from the group consisting of:

(a) an amino acid sequence that is at least 99% identical to SEQ ID NO: 5;

(b) an amino acid sequence that is at least 95% identical to SEQ ID NO: 8;

(c) an amino acid sequence that is at least 97% identical to SEQ ID NO: 35;

(d) an amino acid sequence that is at least 99% identical to SEQ ID NO: 11; and (e) an amino acid sequence corresponding to SEQ ID NO: 2; and wherein the small subunit comprises an amino acid sequence selected from the group consisting of:

(f) SEQ ID NO:3; and (g) SEQ ID NO: 3 having one or more substitutions selected from the group consisting of: (i) D23N; (ii) M33T; (iii) K66N; (iv) S67G; (v) S103G; and (vi) P108S; and wherein the polypeptide does not comprise (e) and (f) together.

The present invention also provides additional Rubisco polypeptides, as well as the Rubisco polynucleotides that encode them, related vectors, host cells, and methods, all of which are provided in more detail below.

DETAILED DESCRIPTION

Figure 1:
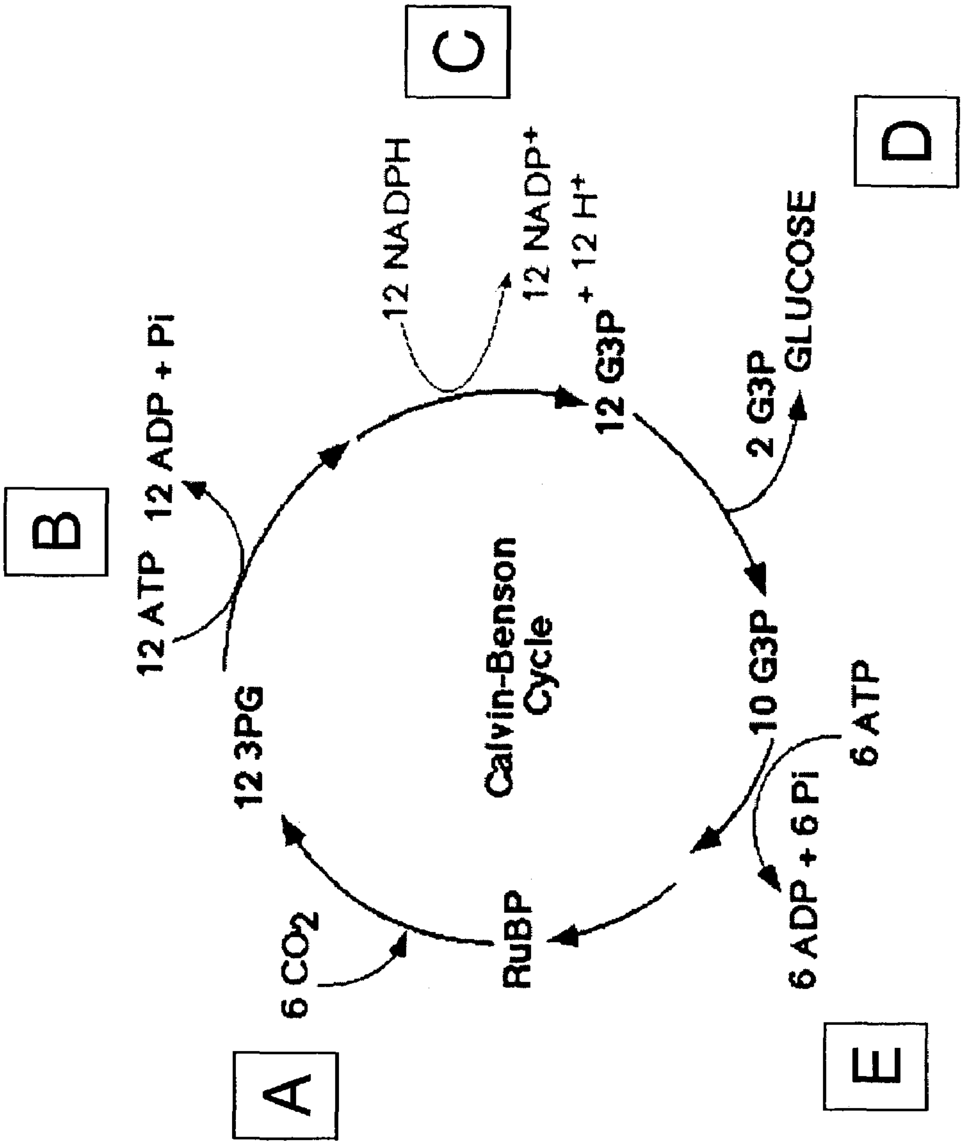
FIG. 1 depicts the Calvin-Benson Cycle

The present invention provides novel ribulose 1,5-bisphosphate carboxylase/oxygenase polypeptides and the polynucleotides that encode them. As used herein, the terms "ribulose 1,5-bisphosphate carboxylase/oxygenase" and "Rubisco" are used interchangeably herein to refer to a polypeptide that, in nature, is made up of two subunits, a large subunit and a small subunit. The large subunit of Rubisco is also referred to as "rbcL" and the small subunit of Rubisco is also referred to as "rbcS". Both subunits together are referred to herein as "rbcLS." The term "Rubisco activity" refers herein to the ability to catalyze the conversion of ribulose 1,5-bisphosphate ("RuBP") to 3-phosphoglycerate ("PG") in the presence of carbon dioxide. This reaction takes place as part of the Calvin-Benson cycle, and is depicted as step "A" of FIG. 1.

The present invention provides Rubisco large subunit polypeptides and polynucleotides, Rubisco small subunit polypeptides and polynucleotides, as well as Rubisco large/small subunit (i.e., having both large and small subunits together in a single polypeptide) polypeptides and polynucleotides (collectively referred to herein as "Rubisco polypeptides" and "Rubisco polynucleotides"). The terms "Rubisco large subunit polypeptide" and "Rubisco rbcL polypeptide" are used interchangeably herein to refer to a polypeptide corresponding to the large subunit of Rubisco. The terms "Rubisco small subunit polypeptide" and "Rubisco rbcS polypeptide" are used interchangeably herein to refer to a polypeptide corresponding to the small subunit of Rubisco. The terms "Rubisco large/small subunit polypeptide" and "Rubisco rbcLS polypeptide" are used interchangeably herein to refer herein to a polypeptide that corresponds to both large and small subunits of Rubisco. Similarly, the terms "Rubisco large subunit polynucleotide" and "Rubisco rbcL polynucleotide" are used interechangeably herein to refer to a polynucleotide that encodes a Rubisco large subunit polypeptide. The terms "Rubisco small subunit polynucleotide" and "Rubisco rbcS polynucleotide" are used interchangeably herein to refer to a polynucleotide that encodes a Rubisco small subunit polypeptide. As used herein, the terms "Rubisco large and small subunit polypeptide" and "Rubisco rbcLS polynucleotide" are used interchangeably herein to refer to a polynucleotide that encodes both a Rubisco large subunit polypeptide and a Rubisco small subunit polypeptide.

Rubisco Polypeptides

Rubisco polypeptides of the present invention include Rubisco large subunit polypeptides ("rbcL"), Rubisco small subunit polypeptides ("rbcS"), and Rubisco large/small polypeptides ("rbcLS"). The terms "protein" and "polypeptide" are used interchangeably herein to refer to a polymer of amino acids. The term "amino acid sequence" refers to the order of amino residues in the protein or polypeptide. Large and small subunits of the present invention may be combined in different combinations with each other together in a single enzyme having Rubisco specific acitivity. Alternatively, the large and small subunits of the present invention may be combined with the large large and small subunits from a wild type Rubisco polypeptides (i.e., invention Rubisco large subunit combined with wild type Rubisco small subunit, or wild type Rubisco large subunit combined with invention Rubisco small subunit) to form a polypeptide having Rubisco activity.

Rubisco rbcLS polypeptides of the present invention exhibit a detectable level of Rubisco specific activity as measured in the assay described in Example 3.

Rubisco Large Subunit Polypeptides

The present invention provides an isolated or recombinant Rubisco large subunit Rubisco polypeptide that comprises an amino acid sequence selected from the group consisting of:

(a) an amino acid sequence that is at least 99% identical to SEQ ID NO: 5;

(b) an amino acid sequence that is at least 95% identical to SEQ ID NO: 8;

(c) an amino acid sequence that is at least 97% identical to SEQ ID NO: 35; and (d) an amino acid sequence that is at least 99% identical to SEQ ID NO: 11.

As used herein, the term "isolated" refers to a nucleic acid, polynucleotide, polypeptide, protein, or other component that is partially or completely separated from components with which it is normally associated (other proteins, nucleic acids, cells, synthetic reagents, etc.). A nucleic acid or polypeptide is "recombinant" when it is artificial or engineered, or derived from an artificial or engineered protein or nucleic acid. For example, a polynucleotide that is inserted into a vector or any other heterologous location, e.g, in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

Specific Rubisco large subunit polypeptides of the present invention include those selected from the group consisting of SEQ ID NO: 5, SEQ ID NO: 8, SEQ ID NO: 11, SEQ ID NO: 14, SEQ ID NO: 20, SEQ ID NO: 29, SEQ ID NO: 32, SEQ ID NO: 35, SEQ ID NO: 38, SEQ ID NO: 41, SEQ ID NO: 47, SEQ ID NO: 50, and SEQ ID NO: 53.

The terms "percent identity," "% identity," "percent identical," and "% identical" are used interchangeably herein to refer to the percent amino acid sequence identity that is obtained by ClustalW analysis (version W 1.8 available form European bioinformatics Institue, Cambridge, UK), counting the number of identical matches in the alignment and dividing such number of identical matches by the length of the reference sequence, and using the following default ClustalW parameters to achieve slow/accurate pairwise alignments—Gap Open Penalty:10; Gap Extension Penalty: 0.10; Protein weight matrix:Gonnet series; DNA weight matrix:IUB; Toggle Slow/Fast pairwise alignments=SLOW or FULL Alignment.

When optimally aligned with reference sequence SEQ ID NO: 5, 8, 35, or 11, certain Rubisco large subunit polypeptides of the present invention are characterized by having at least one amino acid residue selected from the group consisting of: (a) V at position 84; (b) D at position 92; (c) F at position 93; (d) L at position 113; (e) L at position 116; (f) L at position 117; (g) L at position 127; (h) A at position 129; (i) V at position 137; (j) I at position 139; (k) Y at position 141; (l) L at position 142; (m) S at position 149; (n) G at position 154; (o) K at position 158; (p) L at position 166; (q) M at position 209; (r) Q at position 219; (s) E at position 220; (t) E at position 223; (u) A at psition 225 (v) T at position 232; (w) Q at position 246; (x) E at position 249; (y) A at position 252; (z) I at position 257; (aa)T at position 259; (ab) G at position 269; (ac) S at postion 276; (ad) Y at position 280; (ae) L at position 286; (af) A at position 297; (ag) K at position 303; (ah) T at position 304; (ai) M at position 317; (aj) Q at position 322; (ak) T at position 325; (al) R at position 336; (am) Q at position 337; (an) T at position 338; (ao) I at position 343; (ap) Q at position 345; (aq) L at position 346; (ar) S at position 349; (as) F at position 350; (at)P at position 352; (au) E at position 353; (av) N or T at position 356; (aw) N at position 359; (ax) D at position 362; (ay) G at position 366; (az) F at position 372; (ba) A at position 373; (bb) A at position 389; (bc) I at position 415; (bd) R at position 450; and (be) I at position 454.

Two sequences are "optimally aligned" when they are aligned for similarity scoring using a defined amino acid substitution matrix (e.b., BLOSUM62), gap existence penalty and gap extension penalty so as to arrive at the highest core possible for that pair of sequences. Amino acid substitution matrices and their use in quantifying the similarity between two sequences are well-known in the art. See e.g., Dayhoff et al. (1978), "A model of evolutionary change in proteins"; "Atlas of Protein Sequence and Structure," Vol. 5, Suppl. 3 (Ed. M. O. Dayhoff), pp. 345-352, *Natl. Biomed. Res. Round.*, Washington, D.C.; Henikoff et al. (1992) *Proc. Natl. Acad. Sci. USA*, 89:10915-10919. The BLOSUM62 matrix is often used as a default scoring substitution matrix in sequence alignment protocols such as Gapped BLAST 2.0. The gap existence penalty is imposed for the introduction of a single amino acid gap in one of the aligned sequences, and the gap extension penalty is imposed for each additional empty amino acid position inserted into an already opened gap. The alignment is defined by the amino acids position of each sequence at which the alignment begins and ends, and optionally by the insertion of a gap or multiple gaps in one or both sequences so as to arrive at the highest possible score. While optimal alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul, et al. (1997) *Nucleic Acids Res.*, 25:3389-3402, and made available to the public at the National Center for Biotechnology Information Website (the world wide web at ncbi.nlm.nih.gov). Optimal alignments, including multiple alignments can be prepared using readily available programs such as PSI-BLAST, which is described by Altschul, et al. (1997) *Nucleic Acids Res.*, 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. Owing to deletions, insertions, truncations, fusions, etc. that must be taken into account when determining an optimal alignment, in general the amino acid residue number in a test sequence is determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

Rubisco large subunit polypeptides having an amino acid sequence at least 99% identical to SEQ ID NO: 5 typically comprise at least two amino acid residues selected from the group consisting of: I at position 257, T at position 259, M at position 317, A at position 389, and I at position 454.

Rubisco large subunitpolypeptides that have an amino acid sequence at least 95% identical to SEQ ID NO: 8 typically comprise at least two amino acid residues selected from the group consisting of: L at position 113, L at position 117, L at position 127, A at position 129, V at position 137, I at position 139, Y at position 141, L at position 142, Q at position 322, T at position 325, R at position 336, Q at position 337, T at position 338, I at position 343, Q at position 345, L at position 346, S at position 349, F at position 350, P at position 352, E at position 353, T at position 356, N at position 359, D at position 362, G at position 366, F at position 372, and A at position 373.

Rubisco large subunit polypeptides having an amino acid sequence at least 97% identical to SEQ ID NO: 35 typically comprise at least two amino acid residues selected from the group consisting of: S at position 149, M at position 209, Q at position 219, E at position 220, E at position 223, A at position 225, Q at position 246, E at position 249, A at position 252, I at position 257, T at position 259, G at position 269, S at position 276, Y at position 280, L at position 286, K at position 303, T at position 304, and A at position 389.

Rubisco large subunit polypeptides having an amino acid sequence at least 99% identical to SEQ ID NO: 11 typically comprise at least two amino acid residues selected from the group consisting of: V at position 84, K at position 158, L at position 166, M at position 317, and I at position 415.

The present invention also provides an isolated or recombinant Rubisco large subunit polypeptide that comprises an amino acid sequence corresponding to SEQ ID NO: 2 and having one of more substitutions selected from the group consisting of: (a) V at position 84; (b) D at position 92; (c) F at position 93; (d) L at position 113; (e) L at position 116; (f) L at position 117; (g) L at position 127; (h) A at position 129; (i) V at position 137; (j) I at position 139; (k) Y at position 141; (l) L at position 142; (m) S at position 149; (n) G at position 154; (o) K at position 158; (p) L at position 166; (q) M at position 209; (r) Q at position 219; (s) E at position 220; (t) E at position 223; (u) A at psition 225 (v) T at position 232; (w) Q at position 246; (x) E at position 249; (y) A at position 252; (z) I at position 257; (aa)T at position 259; (ab) G at position 269; (ac) S at postion 276; (ad) Y at position 280; (ae) L at position 286; (af) A at position 297; (ag) K at position 303; (ah) T at position 304; (ai) M at position 317; (aj) Q at position 322; (ak) T at position 325; (al) R at position 336; (am) Q at position 337; (an) T at position 338; (ao) I at position 343; (ap) Q at position 345; (aq) L at position 346; (ar) S at position 349; (as) F at position 350; (at)P at position 352; (au) E at position 353; (av) N or T at position 356; (aw) N at position 359; (ax) D at position 362; (ay) G at position 366; (az) F at position 372; (ba) A at position 373; (bb) A at position 389; (bc) I at position 415; (bd) R at position 450; and (be) I at position 454.

The present invention also provides an isolated or recombinant Rubisco large subunit polypeptide that comprises an amino acid sequence encoded by a polynucleotide comprising a nucleic acid selected from the group consisting of:

(a) a nucleic acid that hybridizes under stringent conditions over substantially the entire length of a nucleotide sequence that encodes an amino acid sequence selected from the group consisting of:

(i) SEQ ID NO: 5, wherein the nucleic acid encodes an amino acid sequence that, when optimally aligned with SEQ ID NO: 5, comprises at least two amino acid residues selected from the group consisting of: I at position 257, T at position 259, M at position 317, A at position 389, and I at position 454;

(ii) SEQ ID NO: 8, wherein the nucleic acid encodes an amino acid sequence that, when optimally aligned with SEQ ID NO: 8, comprises at least two amino acid residues selected from the group consisting of: L at position 113, L at position 117, L at position 127, A at position 129, V at position 137, I at position 139, Y at position 141, L at position 142, Q at position 322, T at position 325, R at position 336, Q at position 337, T at position 338, I at position 343, Q at position 345, L at position 346, S at position 349, F at position 350, P at position 352, E at position 353, T at position 356, N at position 359, D at position 362, G at position 366, F at position 372, and A at position 373;

(iii) SEQ ID NO: 35, wherein the nucleic acid encodes an amino acid sequence that, when optimally aligned with SEQ ID NO: 35, comprises at least two amino acid residues selected from the group consisting of: : S at position 149, M at position 209, Q at position 219, E at position 220, E at position 223, A at position 225, Q at position 246, E at position 249, A at position 252, I at position 257, T at position 259, G at position 269, S at position 276, Y at position 280, L at position 286, K at position 303, T at position 304, and A at position 389;

(iv) SEQ ID NO: 11, wherein the nucleic acid encodes an amino acid sequence that, when optimally aligned with SEQ ID NO: 11, comprises at least two amino acid residues selected from the group consisting of: V at position 84, K at position 158, L at position 166, M at position 317, and I at position 415; and (b) a complementary nucleic acid that is complementary to the nucleic acid of (a).

Nucleic acids "hybridize" when they associate, typically in solution. Nucleic acids hybridize due to a variety of well-characterized physico-chemical forces, such as hydrogen bonding, solvent exclusion, base stacking and the like. An extensive guide to the hybridization of nucleic acids is found in Tijssen (1993) "Laboratory Techniques in biochemistry and Molecular Biology-Hybridization with Nucleic Acid Probes," Part I, Chapter 2 (Elsevier, N.Y.).

As used herein, the term "stringent hybridization wash conditions" in the context of nucleic acid hybridization experiments, such as Southern and northern hybridizations, are sequence dependent, and are different under different environmental parameters. An extensive guide to the hybridization of nucleic acids is found in Tijessen (1993) "Laboratory Techniques in Biochemistry and Molecular Biology-Hybridization with Nucleic Acid Probes," Part I, Chapter 2 (Elsevier, N.Y.).

For purposes of the present invention, "highly stringent" hybridization and wash conditions are generally selected to be about 5° C. or less lower than the thermal melting point ($T_m$) for the specific sequence at a defined ionic strength and pH (as noted below, highly stringent conditions can also be referred to in comparative terms). The $T_m$ is the temperature (under defined ionic strength and pH) at which 50% of the test sequence hybridizes to a perfectly matched probe. Very stringent conditions are selected to be equal to the $T_m$ for a particular probe.

The $T_m$ of a nucleic acid duplex indicates the temperature at which the duplex is 50% denatured under the given conditions and it represents a direct measure of the stability of the nucleic acid hybrid. Thus, the $T_m$ corresponds to the temperature corresponding to the midpoint in transition from helix to random coil; it depends on length, nucleotide composition, and ionic strength for long stretches of nucleotides.

After hybridization, unhybridized nucleic acid material can be removed by a series of washes, the stringency of which can be adjusted depending upon the desired results. Low stringency washing conditions (e.g., using higher salt and lower temperature) increase sensitivity, but can produce nonspecific hybridization signals and high background signals. Higher stringency conditions (e.g., using lower salt and higher temperature that is closer to the hybridization temperature) lowers the background signal, typically with only the specific signal remaining. See Rapley, R. and Walker, J. M. Eds., "Molecular Biomethods Handbook" (Humana Press, Inc. 1998).

The $T_m$ of a DNA-DNA duplex can be estimated using Equation 1 as follows:

$$T_m\ (°\ C.)=81.5°\ C.+16.6(\log_{10}M)+0.41\ (\%G+C)-0.72(\%f)-500/n,$$

where M is the molarity of the monovalent cations (usually Na+), (%G+C) is the percentage of guanosine (G) and cystosine (C) nucleotides, (%f) is the percentage of formalize and n is the number of nucleotide bases (i.e., length) of the hybrid. See id.

The $T_m$ of an RNA-DNA duplex can be estimated by using Equation 2 as follows:

$$T_m(°\ C.)=79.8°\ C.+18.5(\log_{10}M)+0.58(\%G+C)-11.8(\%G+C)^2-0.56(\%f)-820/n,$$

where M is the molarity of the monovalent cations (usually Na+), (%G+C)is the percentage of guanosine (G) and cystosine (C) nucleotides, (%f) is the percentage of formamide and n is the number of nucleotide bases (i.e., length) of the hybrid. Id.

Equations 1 and 2 are typically accurate only for hybrid duplexes longer than about 100-200 nucleotides. Id.

The Tm of nucleic acid sequences shorter than 50 nucleotides can be calculated as follows:

$$T_m\ (°\ C.)=4(G+C)+2(A+T),$$

where A (adenine), C, T (thymine), and G are the numbers of the corresponding nucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see Sambrook, et al., Molecular Cloning—A Laboratory Manual" (1989) Cold Spring Harbor Laboratory (Cold Spring Harbor, N.Y.) for a description of SSC buffer). Often the high stringency wash is preceded by a low stringency wash to remove background probe signal. An example low stringency wash is 2×SSC at 40° C. for 15 minutes.

In general, a signal to noise ratio of 2.5×-5× (or higher) than that observed for an unrelated probe in the particular hybridization assay indicates detection of a specific hybridization. Detection of at least stringent hybridization between two sequences in the context of the present invention indicates relatively strong structural similarity or homology to, e.g., the nucleic acids of the present invention provided in the sequence listings herein.

As noted, "highly stringent" conditions are selected to be about 5° C. or less lower than the thermal melting point ($T_m$) for the specific sequence at a defined ionic strength and pH. Target sequences that are closely related or identical to the nucleotide sequence of interest (e.g., "probe") can be identified under highly stringent conditions. Lower stringency conditions are appropriate for sequences that are less complementary.

One measure of stringent hybridization is the ability to hybridize to a nucleic acid that encodes an amino acid sequence selected from SEQ ID NO: 5, SEQ ID NO: 8, SEQ ID NO: 35, and SEQ ID NO: 11, or complementary polynucleotide sequence thereof, under highly stringent conditions (or very stringent conditions, or ultra-high stringency hybridization conditions, or ultra-ultra high stringency hybridization conditions). Stringent hybridization (as well as highly stringent, ultra-high stringency, or ultra-ultra high stringency hybridization conditions) and wash conditions can be readily determined empirically for any test nucleic acid. For example, in determining highly stringent hybridization and wash conditions, the hybridization and wash conditions are gradually increased (e.g., by increasing temperature, decreasing salt concentration, increasing detergent concentration and/or increasing the concentration of organic solvents, such as formalin, in the hybridization or wash), until a selected set of criteria are met. For example, the stringency of hybridization and wash conditions are gradually increased until a probe comprising one or more nucleic acid sequences encoding an amino acid sequence selected from SEQ ID NO: 5, SEQ ID NO: 8, SEQ ID NO: 35, and SEQ ID NO: 11, binds to a perfectly matched complementary target. A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target.

Ultra high-stringency hybridization and wash conditions are those in which the stringency of hybridization and wash conditions are increased until the signal to noise ratio for binding of the probe to the perfectly matched complementary target nucleic acid is at least 10×. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the stringency of hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500×. A target nucleic acid which hybridizes to a probe under such conditions, with a signal to noise ratio of at least ½ that of the perfectly matched complementary target nucleic acid is said to bind to the probe under ultra-ultra-high stringency conditions.

The present invention includes the following target nucleic acids that hybridize under high, ultra-high and ultra-ultra high stringency conditions: (1) target nucleic acids which hybridize to nucleic acids that encode amino acid sequence SEQ ID NO: 5, and which encode an amino acid sequence that comprises at least two amino acid residues selected from the group consisting of: I at position 257, T at position 259, M at position 317, A at position 389, and I at position 454; (2) target nucleic acids which hybridize to nucleic acids that encode SEQ ID NO: 8, and which encode an amino aid sequence that comprises at least two amino acid residues selected from the group consisting of: L at position 113, L at position 117, L at position 127, A at position 129, V at position 137, I at position 139, Y at position 141, L at position 142, Q at position 322, T at position 325, R at position 336, Q at position 337, T at position 338, I at position 343, Q at position 345, L at position 346, S at position 349, F at position 350, P at position 352, E at position 353, T at position 356, N at position 359, D at position 362, G at position 366, F at position 372, and A at position 373; (3) target nucleic acids which hybridize to nucleic acids that encode SEQ ID NO: 35, and which encode an amino acid sequence that comprises at least two amino acid residues selected from the group consisting of: S at position 149, M at position 209, Q at position 219, E at position 220, E at position 223, A at position 225, Q at position 246, E at position 249, A at position 252, I at position 257, T at position 259, G at position 269, S at position 276, Y at position 280, L at position 286, K at position 303, T at position 304, and A at position 389; and (4) target nucleic acids which hybridize to nucleic acids that encode SEQ ID NO: 11, and which encode an amino acid sequence that comprises an amino acid sequence that comprises at least two amino acid residues selected from the group consisting of: V at position 84, K at position 158, L at position 166, M at position 317, and I at position 415; and (5) a complementary nucleic acid that is complementary to any one of (1)-(5).

The present invention also provides Rubisco large subunit polypeptides that comprise at least one of a group of certain specific amino acid residues at positions determined upon optimum alignment with the amino acid sequence corresponding to SEQ ID NO: 5, 8, 35, or 11. These residues are: (a) I at position 454; (b) V at position 84; (c) K at position 158; (d) L at position 166; and (e) M at position 317.

A Rubisco large subunit polypeptide having the amino acid residue I at position 454 of the large subunit appeared to be associated with higher $k_{cat}$ for RuBP as determined by the method described in Example 4. The residues V at position 84, K at position 158, L at position 166, and M at position 317 appeared to confer a lower $K_M$ as determined by the method described in Example 4.

Rubisco Small Subunit Polypeptides

The present invention provides an isolated or recombinant small subunit Rubisco polypeptide that comprises an amino acid sequence corresponding to SEQ ID NO: 3, and having one or more substitutions selected from the group consisting of: (a) D23N; (b) M33T; (c) K66N; (d) S67G; (e) S102G; and (f) P108S.

Exemplary Rubisco small subunit polypeptides of the present invention include those having an amino acid sequence corresponding to SEQ ID NO: 12, SEQ ID NO: 18, SEQ ID NO: 24, SEQ ID NO: 27, SEQ ID NO: 30, SEQ ID NO: 39, SEQ ID NO: 45, SEQ ID NO: 48, and SEQ ID NO: 54.

The invention further provides Rubisco small subunit polypeptides of the present invention that are encoded by an isolated or recombinant polynucleotide comprising:

(a) a nucleic acid that hybridizes under stringent conditions over substantially the entire length of a nucleotide sequence that encodes an amino acid sequence selected from the group consisting of:

(i) SEQ ID NO: 12, wherein the nucleic acid encodes an amino acid sequence that, when optimally aligned with SEQ ID NO: 12, comprises at position 23, amino acid residue N;

(ii) SEQ ID NO: 18, wherein the nucleic acid encodes an amino acid sequence that, when optimally aligned with SEQ ID NO: 18, comprises at position 67, amino acid residue G;

(iii) SEQ ID NO: 24, wherein the nucleic acid encodes an amino acid sequence that, when optimally aligned with SEQ ID NO: 24, comprises at position 108, amino acid residue S;

(iv) SEQ ID NO: 27, wherein the nucleic acid encodes an amino acid sequence that, when optimally aligned with SEQ ID NO: 27, comprises at position 66, amino acid residue N;

(v) SEQ ID NO: 30, wherein the nucleic acid encodes an amino acid sequence that, when optimally aligned with SEQ ID NO: 30, comprises at position 102, amino acid residue G; and (vi) SEQ ID NO: 39, wherein the nucleic acid encodes an amino acid sequence that, when optimally aligned with SEQ ID NO: 39, comprises at position 33, amino acid residue T; or (b) a complementary nucleic acid that is complementary to the nucleic acid of (a).

The present invention also provides Rubisco small subunit polypeptides that comprise N at position 23, where position 23 is determined by optimum alignment with the amino acid sequence corresponding to SEQ ID NO: 3, 12, 18, 24, 27, 30, or 39. This residue appears to be associated with lower $K_M$.

Rubisco Large and Small Subunit (rbcLS) Polypeptides

The present invention provides an isolated or recombinant polypeptide having Rubisco specific activity (as determined by the method of Example 3), wherein the polypeptide comprises a large subunit and a small subunit, wherein the large subunit comprises an amino acid sequence selected from the group consisting of:

(a) an amino acid sequence that is at least 99% identical to SEQ ID NO: 5;

(b) an amino acid sequence that is at least 95% identical to SEQ ID NO: 8;

(c) an amino acid sequence that is at least 97% identical to SEQ ID NO: 35;

(d) an amino acid sequence that is at least 99% identical to SEQ ID NO: 11; and (e) an amino acid sequence corresponding to SEQ ID NO: 2; and wherein the small subunit comprises an amino acid sequence selected from the group consisting of:

(f) SEQ ID NO:3; and (g) SEQ ID NO: 3 having one or more substitutions selected from the group consisting of: (i) D23N; (ii) M33T; (iii) K66N; (iv) S67G; (v) S102G; and (vi) P108S; and wherein the polypeptide does not comprise (e) and (f) together.

The present invention also provides an isolated or recombinant Rubisco rbcLS polypeptide having Rubisco specific activity, wherein the polypeptide comprises a large subunit and a small subunit, wherein the large subunit comprises an amino acid sequence selected from the group consisting of SEQ ID NO: 5, SEQ ID NO: 8, SEQ ID NO: 14, SEQ ID NO: 20, SEQ ID NO: 29, SEQ ID NO: 32, SEQ ID NO: 35, SEQ ID NO: 38, SEQ ID NO: 41, and SEQ ID NO: 40, and wherein the small subunit comprises an amino acid sequence corresponding to SEQ ID NO: 3.

The present invention further provides an isolated or recombinant Rubisco rbcLS polypeptide having Rubisco specific activity and comprising a combination of large and small subunit amino acid sequences selected from the group consisting of:

(a) SEQ ID NO: 11 and SEQ ID NO: 12;

(b) SEQ ID NO: 29 and SEQ ID NO: 30;

(c) SEQ ID NO: 38 and SEQ ID NO: 39;

(d) SEQ ID NO: 47 and SEQ ID NO: 48; and (e) SEQ ID NO: 53 and SEQ ID NO: 54.

Rubisco rbcLS polypeptides of the present invention also include an isolated or recombinant polypeptide having ribulose 1,5-bisphosphate carboxylase/oxygenase activity, wherein the polypeptide comprises a large subunit and a small subunit, wherein the large subunit comprises an amino acid sequence corresponding to SEQ ID NO: 3, and wherein the small subunit comprises an amino acid sequence selected from the group consisting of SEQ ID NO: 18, SEQ ID NO: 24, SEQ ID NO: 27, and SEQ ID NO: 45.

Rubisco Polypeptide Variants

Variants of Rubisco large and small subunit polypeptides of the present invention may be generated using methods that are well known to those having ordinary skill in the art. Libraries of these variants may be generated and screened using the methods described in Example 4 hereinbelow to identify those having Rubisco specific activity.

For example, mutagenesis and directed evolution methods are well known in the art. See, e.g., Ling, et al., "Approaches to DNA mutagenesis: an overview," *Anal. Biochem.*, 254 (2):157-78 (1997); Dale, et al., "Oligonucleotide-directed random mutagenesis using the phosphorothioate method," *Methods Mol. Biol.*, 57:369-74 (1996); Smith, "In vitro mutagenesis," *Ann. Rev. Genet.*, 19:423-462 (1985); Botstein, et al., "Strategies and applications of in vitro mutagenesis," *Science*, 229:1193-1201 (1985); Carter, "Site-directed mutagenesis," *Biochem. J.*, 237:1-7 (1986); Kramer, et al., "Point Mismatch Repair," *Cell*, 38:879-887 (1984); Wells, et al., "Cassette mutagenesis: an efficient method for generation of multiple mutations at defined sites," *Gene*, 34:315-323 (1985); Minshull, et al., "Protein evolution by molecular breeding," *Current Opinion in Chemical Biology*, 3:284-290 (1999); Christians, et al., "Directed evolution of thymidine kinase for AZT phosphorylation using DNA family shuffling," *Nature Biotechnology*, 17:259-264 (1999); Crameri, et al., "DNA shuffling of a family of genes from diverse species accelerates directed evolution," *Nature*, 391:288-291; Crameri, et al., "Molecular evolution of an arsenate detoxification pathway by DNA shuffling," *Nature Biotechnology*, 15:436-438 (1997); Zhang, et al., "Directed evolution of an effective fucosidase from a galactosidase by DNA shuffling and screening," *Proceedings of the National Academy of Sciencess. U.S.A.*, 94:45-4-4509; Crameri, et al., "Improved green fluorescent protein by molecular evolution using DNA shuffling," *Nature Biotechnology*<14:315-319 (1996); Stemmer, "Rapid evolution of a protein in vitro by DNA shuffling," *Nature*, 370:389-391 (1994); Stemmer, "DNA shuffling by random fragmentation and reassembly: In vitro recombination for molecular evolution," *Proceedings of the National Academy of Sciences, U.S.A.*, 91:10747-10751 (1994); WO 95/22625; WO 97/0078; WO 97/35966; WO 98/27230; WO 00/42651; and WO 01/75767.

Rubisco Polynucleotides

Rubisco Large Subunit Polynucleotides

The present invention provides an isolated or recombinant Rubisco large subunit polynucleotide that comprises a nucleic acid having a nucleotide sequence selected from the group consisting of:

(a) a nucleotide sequence encoding an amino acid sequence that is at least 99% identical to SEQ ID NO: 5;

(b) a nucleotide sequence encoding an amino acid sequence that is at least 95% identical to SEQ ID NO: 8;

(c) a nucleotide sequence encoding an amino acid sequence that is at least 97% identical to SEQ ID NO: 35;

(d) a nucleotide sequence encoding an amino acid sequence that is at least 99% identical to SEQ ID NO: 11; and (e) a nucleotide sequence that is complementary to any one of (a) through (d).

The terms "polynucleotide" and "nucleic acid" are used interchangeably herein to refer to a polymer of nucleotides (A, C, T, U, G, etc. or naturally occurring or artificial nucleotide analogues), e.g., DNA or RNA, or a representation thereof. The terms "polynucleotide sequence" and "nucleic acid sequence" are used interchangeably herein to refer to the order of nucleotides in the polynucleotide or nucleic acid. A complementary polynucleotide can be readily determined from any specified polynucleotide sequence.

Specific large subunit Rubisco polynucleotides of the present invention comprise a polynucleotide sequence that encodes an amino acid sequence selected from the group consisting of SEQ ID NO: 5, SEQ ID NO: 8, SEQ ID NO: 11, SEQ ID NO: 14, SEQ ID NO: 20, SEQ ID NO: 29, SEQ ID NO: 32, SEQ ID NO: 35, SEQ ID NO: 38, SEQ ID NO: 41, SEQ ID NO: 47, SEQ ID NO: 50, and SEQ ID NO: 53.

Certain Rubisco large subunit polynucleotides encode Rubisco large subunit polypeptides having at least one amino residue from the set of (a)-(bd) residues listed below. The amino acid residue positions refer to the position in the encoded amino acid sequence when it is optimally aligned with reference sequence SEQ ID NO: 5, 8, 35, or 11. The polypeptides encoded by the large subunit Rubisco polynucleotides typically have at least one amino acid residue selected from the group consisting of: (a) V at position 84; (b) D at position 92; (c) F at position 93; (d) L at position 113; (e) L at position 116; (f) L at position 117; (g) L at position 127; (h) A at position 129; (i) V at position 137; (j) I at position 139; (k) Y at position 141; (l) L at position 142; (m) S at position 149; (n) G at position 154; (o) K at position 158; (p) L at position 166; (q) M at position 209; (r) Q at position 219; (s) E at position 220; (t) E at position 223; (u) A at position 225 (v) T at position 232; (w) Q at position 246; (x) E at position 249; (y) A at position 252; (z) I at position 257; (aa)T at position 259; (ab) G at position 269; (ac) S at postion 276; (ad) Y at position 280; (ae) L at position 286; (af) A at position 297; (ag) K at position 303; (ah) T at position 304; (ai) M at position 317; (aj) Q at position 322; (ak) T at position 325; (al) R at position 336; (am) Q at position 337; (an) T at position 338; (ao) I at position 343; (ap) Q at position 345; (aq) L at position 346; (ar) S at position 349; (as) F at position 350; (at)P at position 352; (au) E at position 353; (av) N or T at position 356; (aw) N at position 359; (ax) D at position 362; (ay) G at position 366; (az) F at position 372; (ba) A at position 373; (bb) A at position 389; (bc) I at position 415; (bd) R at position 450; and (be) I at position 454.

When the amino acid sequence encoded by the Rubisco large subunit polynucleotide is at least 99% identical to SEQ ID NO: 5, it typically comprises at least two amino acid residues selected from the group consisting of: I at position 257, T at position 259, M at position 317, A at position 389, and I at position 454. When the amino acid sequence encoded by the Rubisco large subunit polynucleotide is at least 95% identical to SEQ ID NO: 8, it typically comprises at least two amino acid residues selected from the group consisting of: L at position 113, L at position 117, L at position 127, A at position 129, V at position 137, I at position 139, Y at position 141, L at position 142, Q at position 322, T at position 325, R at position 336, Q at position 337, T at position 338, I at position 343, Q at position 345, L at position 346, S at position 349, F at position 350, P at position 352, E at position 353, T at position 356, N at position 359, D at position 362, G at position 366, F at position 372, and A at position 373. Rubisco large subunit polynucleotides encoding an amino acid sequence that is at least 97% identical to SEQ ID NO: 35 typically encode an amino acid sequence that comprises at least two amino acid residues selected from the group consisting of: S at position 149, M at position 209, Q at position 219, E at position 220, E at position 223, A at position 225, Q at position 246, E at position 249, A at position 252, I at position 257, T at position 259, G at position 269, S at position 276, Y at position 280, L at position 286, K at position 303, T at position 304, and A at position 389. position 450; and (bd) I at position 454. When the amino acid sequence encoded by the Rubisco large subunit polynucleotide is at least 99% identical to SEQ ID NO: 11, it typically comprises at least two amino acid residues selected from the group consisting of: V at position 84, K at position 158, L at position 166, M at position 317, and I at position 415.

The present invention also provides an isolated or recombinant Rubisco large subunit polynucleotides comprising a nucleotide sequence encoding an amino acid sequence corresponding to SEQ ID NO: 2 and having one of more substitutions selected from the group consisting of: (a) V at position 84; (b) D at position 92; (c) F at position 93; (d) L at position 113; (e) L at position 116; (f) L at position 117; (g) L at position 127; (h) A at position 129; (i) V at position 137; (j) I at position 139; (k) Y at position 141; (l) L at position 142; (m) S at position 149; (n) G at position 154; (o) K at position 158; (p) L at position 166; (q) M at position 209; (r) Q at position 219; (s) E at position 220; (t) E at position 223; (u) A at psition 225 (v) T at position 232; (w) Q at position 246; (x) E at position 249; (y) A at position 252; (z) I at position 257; (aa)T at position 259; (ab) G at position 269; (ac) S at postion 276; (ad) Y at position 280; (ae) L at position 286; (af) A at position 297; (ag) K at position 303; (ah) T at position 304; (ai) M at position 317; (aj) Q at position 322; (ak) T at position 325; (al) R at position 336; (am) Q at position 337; (an) T at position 338; (ao) I at position 343; (ap) Q at position 345; (aq) L at position 346; (ar) S at position 349; (as) F at position 350; (at)P at position 352; (au) E at position 353; (av) N or T at position 356; (aw) N at position 359; (ax) D at position 362; (ay) G at position 366; (az) F at position 372; (ba) A at position 373; (bb) A at position 389; (bc) I at position 415; (bd) R at position 450; and (be) I at position 454.

The present invention also provides an isolated or recombinant Rubisco large subunit polynucleotide comprising:

(a) a nucleic acid that hybridizes under stringent conditions over substantially the entire length of a nucleotide sequence that encodes an amino acid sequence selected from the group consisting of:

(i) SEQ ID NO: 5, wherein the nucleic acid encodes an amino acid sequence that, when optimally aligned with SEQ ID NO: 5, comprises at least two amino acid residues selected from the group consisting of: I at position 257, T at position 259, M at position 317, A at position 389, and I at position 454;

(ii) SEQ ID NO: 8, wherein the nucleic acid encodes an amino acid sequence that, when optimally aligned with SEQ ID NO: 8, comprises at least two amino acid residues selected from the group consisting of: L at position 113, L at position 117, L at position 127, A at position 129, V at position 137, I at position 139, Y at position 141, L at position 142, Q at position 322, T at position 325, R at position 336, Q at position 337, T at position 338, I at position 343, Q at position 345, L at position 346, S at position 349, F at position 350, P at position 352, E at position 353, T at position 356, N at position 359, D at position 362, G at position 366, F at position 372, and A at position 373;

(iii) SEQ ID NO: 35, wherein the nucleic acid encodes an amino acid sequence that, when optimally aligned with SEQ ID NO: 35, comprises at least two amino acid residues selected from the group consisting of: : S at position 149, M at position 209, Q at position 219, E at position 220, E at position 223, A at position 225, Q at position 246, E at position 249, A at position 252, I at position 257, T at position 259, G at position 269, S at position 276, Y at position 280, L at position 286, K at position 303, T at position 304, and A at position 389;

(iv) SEQ ID NO: 11, wherein the nucleic acid encodes an amino acid sequence that, when optimally aligned with SEQ ID NO: 11, comprises at least two amino acid residues selected from the group consisting of: V at position 84, K at position 158, L at position 166, M at position 317, and I at position 415; and (b) a complementary nucleic acid that is complementary to the nucleic acid of (a).

Specific isolated and recombinant Rubisco large subunit polynucleotides of the present invention correspond in sequence to positions 1 through 1419, inclusive, of a polynucleotide sequence selected from the group consisting of: SEQ ID NO: 4, SEQ ID NO: 7, SEQ ID NO: 10, SEQ ID NO: 13, SEQ ID NO: 19, SEQ ID NO: 28, SEQ ID NO: 31, SEQ ID NO: 34, SEQ ID NO: 37, SEQ ID NO: 40, SEQ ID NO: 46, SEQ ID NO 49, and SEQ ID NO: 52, and SEQ ID NO: 55.

Rubisco Small Subunit Polynucleotides

The present invention provides an isolated or recombinant Rubisco small subunit polynucleotide comprising a nucleotide sequence that encodes an amino acid sequence corresponding to SEQ ID NO: 3 that has one or more substitutions selected from the group consisting of: (a) D23N; (b) M33T; (c) K66N; (d) S67G; (e) S102G; and (f) P108S. Specific Rubisco small subunit polynucleotides of the present invention comprise a polynucleotide sequence that encodes an amino acid sequence that is selected from the group consisting of SEQ ID NO: 12, SEQ ID NO: 18, SEQ ID NO: 24, SEQ ID NO: 27, SEQ ID NO: 30, and SEQ ID NO: 39.

The present invention also provides an isolated or recombinant Rubisco small subunit polynucleotide comprising a nucleic acid selected from the group consisting of:

(a) a nucleic acid that hybridizes under stringent conditions over substantially the entire length of a nucleotide sequence that encodes an amino acid sequence selected from the group consisting of:

(i) SEQ ID NO: 12, wherein the nucleic acid encodes an amino acid sequence that, when optimally aligned with SEQ ID NO: 12, comprises at position 23, amino acid residue N;

(ii) SEQ ID NO: 18, wherein the nucleic acid encodes an amino acid sequence that, when optimally aligned with SEQ ID NO: 18, comprises at position 67, amino acid residue G;

(iii) SEQ ID NO: 24, wherein the nucleic acid encodes an amino acid sequence that, when optimally aligned with SEQ ID NO: 24, comprises at position 108, amino acid residue S;

(iv) SEQ ID NO: 27, wherein the nucleic acid encodes an amino acid sequence that, when optimally aligned with SEQ ID NO: 27, comprises at position 66, amino acid residue N;

(v) SEQ ID NO: 30, wherein the nucleic acid encodes an amino acid sequence that, when optimally aligned with SEQ ID NO: 30, comprises at position 102, amino acid residue G; and (vi) SEQ ID NO: 39, wherein the nucleic acid encodes an amino acid sequence that, when optimally aligned with SEQ ID NO: 39, comprises at position 33, amino acid residue T; or (b) a complementary nucleic acid that is complementary to the nucleic acid of (a).

Specific Rubisco small subunit polynucleotides of the present invention comprise a polynucleotide sequence corresponding to positions 1510 through 1845 inclusive, of a polynucleotide sequence selected from the group consisting of: SEQ ID NO: 10, SEQ ID NO: 16, SEQ ID NO: 22, SEQ ID NO: 28, SEQ ID NO: 37, SEQ ID NO: 55.

Rubisco Large and Small Subunit Polynucleotides

The present invention provides an isolated or recombinant rbcLS polynucleotide comprising a nucleic acid that encodes a Rubisco large subunit polypeptide and a nucleic acid encoding a Rubisco small subunit polypeptide, wherein the nucleic acid encoding the Rubisco large subunit polypeptide is selected from the group consisting of:

(a) a nucleotide sequence encoding an amino acid sequence that is at least 99% identical to SEQ ID NO: 5;

(b) a nucleotide sequence encoding an amino acid sequence that is at least 95% identical to SEQ ID NO: 8;

(c) a nucleotide sequence encoding an amino acid sequence that is at least 97% identical to SEQ ID NO: 35;

(d) a nucleotide sequence encoding an amino acid sequence that is at least 99% identical to SEQ ID NO: 11; and (e) a nucleotide sequence that is complementary to any one of (a) through (d); and wherein the nucleic acid encoding the Rubisco small subunit polypeptide encodes an amino acid sequence having a sequence selected from the group consisting of:

(a) SEQ ID NO:3; and (b) SEQ ID NO: 3 having one or more substitutions selected from the group consisting of: (i) D23N; (ii) M33T; (iii) K66N; (iv) S67G; (v) S103G; and (vi) P108S.

Isolated or recombinant Rubisco polynucleotides comprise a nucleic acid encoding a Rubisco large subunit polypeptide and a nucleic acid encoding a Rubisco small subunit polypeptide, wherein the nucleic acid encoding the Rubisco large subunit polypeptide has a nucleotide sequence that encodes an amino acid sequence corresponding to SEQ ID NO: 2 and wherein the nucleic acid encoding the Rubisco small subunit polypeptide encodes an amino acid sequence corresponding to SEQ ID NO: 3 that has one or more substitutions selected from the group consisting of: (a) D23N; (b) M33T; (c) K66N; (d) S67G; (e) S102G; and (f) P108S. Specific Rubisco polynucleotides of the present invention include a polynucleotide sequence selected from the group consisting of SEQ ID NO: 4, SEQ ID NO: 7, SEQ ID NO: 10, SEQ ID NO: 13, SEQ ID NO: 16, SEQ ID NO: 19, SEQ ID NO: 22, SEQ ID NO: 25, SEQ ID NO: 28, SEQ ID NO: 31, SEQ ID NO: 34, SEQ ID NO: 37, SEQ ID NO: 40, SEQ ID NO: 43, SEQ ID NO: 46, SEQ ID NO: 49, and SEQ ID NO: 52.

Polynucleotides that encode both large and small subunits of the Rubisco polyptides (rbcLS) of the present invention typically are separated by an intervening, non-coding polynucleotide sequence that operates as a linker. The linker separates the subunit polynucleotide coding sequences, and extends from the 3' end of the large subunit coding sequence to the 5' end of the small subunit coding sequence. The specific sequence of the linker is not critical. The linker is generally at least about 30 nucleotides in length, typically at least about 50 nucleotides in length, and usually at least about 80 nucleotides in length, up to about 100 nucleotides in length. The present invention provides isolated or recombinant Rubisco rbcLS polynucleotides having a linker sequence separating Rubisco rbcL and Rubisco rbcS polynucleotide sequences. Exemplary linkers include the polynucleotide sequence extending from position 1420 to position 1509, inclusive, of SEQ ID NOS: 1, 4, 7, 10, 13, 16, 19, 22, 25, 28, 31, 34, 37, 40, 43, 46, 49, and 52.

Polynucleotide Sequence Variations

Those having ordinary skill in the art will readily appreciate that due to the degeneracy of the genetic code, a multitude of nucleotide sequences encoding Rubisco polypeptides of the present invention exist. Table I is a Codon Table that provides the synonymous codons for each amino acid. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

TABLE 1

Codon Table

| Amino acids | | | Codon | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |

TABLE 1-continued

| Codon Table | | | | | | | | | |
|---|---|---|---|---|---|---|---|---|---|
| Amino acids | | | Codon | | | | | | |
| Glutamic acid | Glu | E | GAA | GAG | | | | | |
| Phenylalanine | Phe | F | UUC | UUU | | | | | |
| Glycine | Gly | G | GGA | GGC | GGG | GGU | | | |
| Histidine | His | H | CAC | CAU | | | | | |
| Isoleucine | Ile | I | AUA | AUC | AUU | | | | |
| Lysine | Lys | K | AAA | AAG | | | | | |
| Leucine | Leu | L | UUA | UUG | CUA | CUC | CUG | CUU | |
| Methionine | Met | M | AUG | | | | | | |
| Asparagine | Asn | N | AAC | AAU | | | | | |
| Proline | Pro | P | CCA | CCC | CCG | CCU | | | |
| Glutamine | Gln | Q | CAA | CAG | | | | | |
| Arginine | Arg | R | AGA | AGG | CGA | CGC | CGG | CGU | |
| Serine | Ser | S | AGC | AGU | UCA | UCC | UCG | UCU | |
| Threonine | Thr | T | ACA | ACC | ACG | ACU | | | |
| Valine | Val | V | GUA | GUC | GUG | GUU | | | |
| Tryptophan | Trp | W | UGG | | | | | | |
| Tyrosine | Tyr | Y | UAC | UAU | | | | | |

Such "silent variations" are one species of "conservative" variation. One of ordinary skill in the art will recognize that each codon in a nucleic acid (except AUG, which is ordinarily the only codon for methionine) can be modified by standard techniques to encode a functionally identical polypeptide. Accordingly, each silent variation of a nucleic acid which encodes a polypeptide is implicit in any described sequence. The invention provides each and every possible variation of nucleic acid sequence encoding a polypeptide of the invention that could be made by selecting combinations based on possible codon choices. These combinations are made in accordance with the standard triplet genetic code (set forth in Table 1), as applied to the polynucleotide sequences encoding the Rubisco large subunit, small subunit, and large and small subunit polypeptides of the present invention.

A group of two or more different codons that, when translated in the same context, all encode the same amino acid, are referred to herein as "synonymous codons."Rubisco polynucleotides of the present invention may be codon optimized for expression in a particular host organism by modifying the polynucleotides to conform with the optimum codon usage of the desired host organism. Those having ordinary skill in the art will recognize that tables and other references providing preference information for a wide range of organisms are readily available See e.g., the world wide web at kazusa.orgjp/codon/. For example, Rubisco polynucleotides may be codon optimized for expression from a blue green algae, such as a *Synechocystis* sp. An exemplary codon optimized Rubisco polynucleotide sequence of the present invention is provided as SEQ ID NO: 55, in which SEQ ID NO: 40 has been codon optimized for expression from *Synechocystis.*

The terms "conservatively modified variations" and "conservative variations" are used interchangeably herein to refer to those nucleic acids that encode identical or or essentially identical amino acid sequences, or in the situation where the nucleic acids are not coding sequences, the term refers to nucleic acids that are identical. One of ordinary skill in the art will recognize that individual substitutions, deletions or additions which alter, add or delete a single amino acid or a small percentage of amino acids in an encoded sequence are considered conservatively modified variations where the alterations result in one or more of the following: the deletion of an amino acid, addition of an amino acid, or substitution of an amino acid with a chemically similar amino acid. When more than one amino acid is affected, the percentage is typically less than 5% of amino acid residues over the length of the encoded sequence, and more typically less than 2%. Conservative substitution tables providing amino acids that are considered conservative substitutions for one another are well known in the art. Table 2 provides a list of six conservative substitution groupings of amino acids.

TABLE 2

| Conservative Substitution Groups | | | | |
|---|---|---|---|---|
| 1 | Alanine (A) | Serine (S) | Threonine (T) | |
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Conservatively substituted variations of the Rubisco polypeptides of the present invention include substitutions of a small percentage, typically less than 5%, more typically less than 2%, and often less than 1% of the amino acids of the polypeptide sequence, with a conservatively selected amino acid of the same conservative substitution group. The addition of sequences which do not alter the encoded activity of a Rubisco polynucleotide, such as the addition of a non-functional or non-coding sequence, is considered a conservative variation of the Rubisco polynucleotide.

Vectors, Promoters, and Expression Systems

The present invention also includes recombinant constructs comprising one or more of the nucleic acid sequences as broadly described above. The term "construct" or "nucleic acid construct" refers herein to a nucleic acid, either single- or double-stranded, which is isolated from a naturally occurring gene or which has been modified to contain segments of nucleic acids in a manner that would not otherwise exist in nature. The term "nucleic acid construct" is synonymous with the term "expression cassette" when the nucleic acid construct contains the control sequences required for expression of a coding sequence of the present invention.

The term "control sequences" refers herein to all the components that are necessary or advantageous for the expression of a polypeptide of the present invention. Each control sequence may be native or foreign to the nucleotide sequence encoding the polypeptide. Such control sequences include, but are not limitd to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "operably linked" refers herein to a configuration in which a control sequence is appropriately placed at a position relative to the coding sequence of the DNA sequence such that the control sequence directs the expression of a polypeptide.

When used herein, the term "coding sequence" is intended to cover a nucleotide sequence, which directly specifies the amino acid sequence of its protein product. The boundaries of the coding sequence are generally determined by an open reading frame, which usually begins with the ATG start codon. The coding sequence typically includes a DNA, cDNA, and/or recombinant nucleotide sequence.

As used herein, the term "expression" includes any step involved in the production of the polypeptide including, but not limited to, transcription, post-transcriptional modification, translation, post-translational modification, and secretion.

The term "expression vector" refers herein to a DNA molecule, linear or circular, that comprises a segment encoding a polypeptide of the invention, and which is operably linked to additional segments that provide for its transcription.

As used herein, the term "host cell" refers to any cell type which is susceptible to transformation with a nucleic acid construct.

Nucleic acid constructs of the present invention comprise a vector, such as, a plasmid, a cosmid, a phage, a virus, a bacterial artificial chromosome (BAC), a yeast artificial chromosome (YAC), or the like, into which a nucleic acid sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available.

General texts which describe molecular biological techniques useful herein, including the use of vectors, promoters and many other relevant topics, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (2nd Ed.), Vol. 1-3, Cold Spring Harbor Laboratory, Cold Spring Harbor, N.Y., 1989 ("Sambrook") and *Current Protocols in Molecular Biology*, F. M. Ausubel et al., eds., Current Protocols, a joint venture between Greene Publishing Associates, Inc. and John Wiley & Sons, Inc., (supplemented through 1999) ("Ausubel"). Examples of protocols sufficient to direct persons of skill through in vitro amplification methods, including the polymerase chain reaction (PCR) the ligase chain reaction (LCR), Q∃-replicase amplification and other RNA polymerase mediated techniques (e.g., NASBA), e.g., for the production of the homologous nucleic acids of the invention are found in Berger, Sambrook, and Ausubel, as well as Mullis et al., (1987) U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) *C&EN* 36-47*; The Journal Of NIH Research* (1991) 3, 81-94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077-1080; Van Brunt (1990) *Biotechnology* 8, 291-294; Wu and Wallace, (1989) *Gene* 4, 560; Barringer et al. (1990) *Gene* 89, 117, and Sooknanan and Malek (1995) *Biotechnology* 13: 563-564. Improved methods for cloning in vitro amplified nucleic acids are described in Wallace et al., U.S. Pat. No. 5,426,039. Improved methods for amplifying large nucleic acids by PCR are summarized in Cheng et al. (1994) *Nature* 369: 684-685 and the references cited therein, in which PCR amplicons of up to 40 kb are generated. One of of ordinary skill in the art will readily appreciate that essentially any RNA can be converted into a double stranded DNA suitable for restriction digestion, PCR expansion and sequencing using reverse transcriptase and a polymerase. See, e.g., Ausubel, Sambrook and Berger, all supra.

The present invention also relates to engineered host cells that are transduced (transformed or transfected) with a vector of the invention (e.g., an invention cloning vector or an invention expression vector), as well as the production of polypeptides of the invention by recombinant techniques. The vector may be, for example, a plasmid, a viral particle, a phage, etc. The engineered host cells can be cultured in conventional nutrient media modified as appropriate for activating promoters, selecting transformants, or amplifying the Rubisco polynucleotide. Culture conditions, such as temperature, pH and the like, are those previously used with the host cell selected for expression, and will be apparent to those skilled in the art and in the references cited herein, including, e.g., Sambrook, Ausubel and Berger, as well as e.g., Freshney (1994) *Culture of Animal Cells, a Manual of Basic Technique*, third edition, Wiley-Liss, New York and the references cited therein.

Rubisco polypeptides of the invention can be produced in non-animal cells such as plants, yeast, fungi, bacteria (e.g., cyanobacteria) and the like. In addition to Sambrook, Berger and Ausubel, details regarding non-animal cell culture can be found in Payne et al. (1992) *Plant Cell and Tissue Culture in Liquid Systems* John Wiley & Sons, Inc. New York, N.Y.; Gamborg and Phillips (eds) (1995) *Plant Cell Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Polynucleotides of the present invention can be incorporated into any one of a variety of expression vectors suitable for expressing a polypeptide. Suitable vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, pseudorabies, adenovirus, adeno-associated virus, retroviruses and many others. Any vector that transduces genetic material into a cell, and, if replication is desired, which is replicable and viable in the relevant host can be used.

When incorporated into an expression vector, a polynucleotide of the invention is operatively linked to an appropriate transcription control sequence (promoter) to direct mRNA synthesis. Examples of such transcription control sequences particularly suited for use in transgenic plants include the cauliflower mosaic virus (CaMV) and figwort mosaic virus (FMV). Other promoters known to control expression of genes in prokaryotic or eukaryotic cells or their viruses and which can be used in some embodiments of the invention include SV40 promoter, *E. coli* lac or trp promoter, phage lambda $P_L$ promoter. An expression vector optionally contains a ribosome binding site for translation initiation, and a transcription terminator, such as PinII. The vector also optionally includes appropriate sequences for amplifying expression, e.g., an enhancer.

In addition, the expression vectors of the present invention optionally contain one or more selectable marker genes to provide a phenotypic trait for selection of transformed host cells. Suitable marker genes include those coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. Additional selectable marker genes include dihydrofolate reductase or neomycin resistance for eukaryotic cell culture, and tetracycline or ampicillin resistance in *E. coli.*

Vectors of the present invention can be employed to transform an appropriate host to permit the host to express an invention protein or polypeptide. Examples of appropriate expression hosts include bacterial cells, such as *E. coli, B. subtilis*, and *Streptomyces*, cyanobacterial cells such as *Synechocystis, Synechococcus, Anabaena, Anacystis*, and the like, and plant cells.

In bacterial systems, a number of expression vectors may be selected, such as, for example, multifunctional *E. coli* cloning and expression vectors. In cyanobacterial systems, vectors such as those described in Example 5 may be used.

In plant cells, expression can be driven from a transgene integrated into a plant chromosome, or cytoplasmically from an episomal or viral nucleic acid. In the case of stably integrated transgenes, it is often desirable to provide sequences capable of driving constitutive or inducible expression of the Rubisco polynucleotides of the invention, for example, using viral, e.g., CaMV, or plant derived regulatory sequences. Numerous plant derived regulatory sequences have been described, including sequences which direct expression in a tissue specific manner, e.g., TobRB7, patatin B33, GRP gene promoters, the rbcS-3A promoter, and the like. Alternatively, high level expression can be achieved by transiently expressing exogenous sequences of a plant viral vector, e.g., TMV, BMV, etc. Typically, transgenic plants constitutively expressing a Rubisco polynucleotide of the invention will be preferred, and the regulatory sequences selected to insure constitutive stable expression of the Rubisco polypeptide.

Typical vectors useful for expression of nucleic acids in higher plants are well known in the art and include vectors derived from the tumor-inducing (Ti) plasmid of *Agrobacterium tumefaciens* described by Rogers et al., Meth. In Enzymol., 153:253-277 (1987). Exemplary *A. tumefaciens* vectors useful herein are plasmids pKYLX6 and pKYLX7 of Schardl et al., Gene, 61:1-11 (1987) and Berger et al., Proc. Natl. Acad. Sci. U.S.A., 86:8402-8406 (1989). Another useful vector herein is plasmid pBI101.2 that is available from Clontech Laboratories, Inc. (Palo Alto, Calif.). A variety of plant viruses that can be employed as vectors are known in the art and include cauliflower mosaic virus (CaMV), geminivirus, brome mosaic virus, and tobacco mosaic virus.

In some embodiments of the present invention, a Rubisco polynucleotide construct suitable for transformation of plant cells is prepared. For example, a desired Rubisco polynucleotide can be incorporated into a recombinant expression cassette to facilitate introduction of the gene into a plant and subsequent expression of the encoded polypeptide. An expression cassette will typically comprise a Rubisco polynucleotide, or functional fragment thereof, operably linked to a promoter sequence and other transcriptional and translational initiation regulatory sequences which will direct expression of the sequence in the intended tissues (e.g., entire plant, leaves, seeds) of the transformed plant.

For example, a strongly or weakly constitutive plant promoter can be employed which will direct expression of the Rubisco polypeptide all tissues of a plant. Such promoters are active under most environmental conditions and states of development or cell differentiation. Examples of constitutive promoters include the cauliflower mosiac virus (CaMV) 35S transcription initiationa region, the 1'- or 2'-promoter derived from T-DNA of *Agrobacterium tumefaciens*, the ubiquitin 1 promoter, the Smas promoter, the cinnamyl alcohol dehydrogenase promoter (U.S. Pat. No. 5,683,439), the Nos promoter, the pEmu promoter, the rubisco promoter, the GRP1-8 promoter and other transcription initiation regions from various plant genes known to those of skill. In situations in which overexpression of a Rubisco poynucleotide is detrimental to the plant or otherwise undesirable, one of skill, upon review of this disclosure, will recognize that weak constitutive promoters can be used for low-levels of expression. In those cases where high levels of expression is not harmful to the plant, a strong promoter, e.g., a t-RNA or other pol III promoter, or a strong pol II promoter, such as the cauliflower mosaic virus promoter, can be used.

Alternatively, a plant promoter may be under environmental control. Such promoters are referred to here as "inducible" promoters. Examples of environmental conditions that may effect transcription by inducible promoters include pathogen attack, anaerobic conditions, or the presence of light. In particular, examples of inducible promoters are the Adh 1 promoter which is inducible by hypoxia or cold stress, the Hsp70 promoter which is inducible by heat stress, and the PPDK promoter which is inducible by light. Also useful are promoters which are chemically inducible.

The promoters used in the present invention can be "tissue-specific" and, as such, under developmental control in that the polynucleotide is expressed only in certain tissues, such as leaves, roots, fruit, flowers and seeds. An exemplary promoter is the anther specific promoter 5126 (U.S. Pat. Nos. 5,689,049 and 5,689,051). Examples of seed-preferred promoters include, but are not limited to, 27 kD gamma zein promoter and waxy promoter, Boronat, A., Martinez, M. C., Reina, M., Puigdomenech, P. and Palau, J.; Isolation and sequencing of a 28 kD glutelin-2 gene from maize: Common elements in the 5' flanking regions among zein and glutelin genes; *Plant Sci*. 47, 95-102 (1986) and Reina, M., Ponte, I., Guillen, P., Boronat, A. and Palau, J., Sequence analysis of a genomic clone encoding a Zc2 protein from *Zea mays* W64 A, *Nucleic Acids Res*. 18 (21), 6426 (1990). See the following site relating to the waxy promoter: Kloesgen, R. B., Gierl, A., Schwarz-Sommer, ZS. and Saedler, H., Molecular analysis of the waxy locus of *Zea mays, Mol. Gen. Genet*. 203, 237-244 (1986). In embodiments in which one or more nucleic acid sequences endogenous to the plant system are incorporated into the construct, the endogenous promoters (or variants thereof) from these genes can be employed for directing expression of the genes in the transfected plant. Tissue-specific promoters can also be used to direct expression of heterologous polynucleotides.

In general, the particular promoter used in the expression cassette in plants depends on the intended application. Either heterologous or non-heterologous (i.e., endogenous) promoters can be employed to direct expression of the nucleic acids of the present invention. These promoters can also be used, for example, in expression cassettes to drive expression of antisense nucleic acids to reduce, increase, or alter concentration and/or composition of the proteins of the present invention in a desired tissue. Any of a number of promoters which direct transcription in plant cells are suitable. The promoter can be either constitutive or inducible. In addition to the promoters noted above, promoters of bacterial origin which operate in plants include the octopine synthase promoter, the nopaline synthase promoter and other promoters derived from native Ti plasmids (see, Herrara-Estrella et al. (1983) *Nature* 303:209-213). Viral promoters include the 35S and 19S RNA promoters of cauliflower mosaic virus (Odell et al. (1985) *Nature* 313:810-812). Other plant promoters include the ribulose-1,3-bisphosphate carboxylase small subunit promoter and the phaseolin promoter. The promoter sequence from the E8 gene and other genes may also be used. The isolation and sequence of the E8 promoter is described in detail in Deikman and Fischer (1988) *EMBO J.* 7:3315-3327.

To identify candidate promoters, the 5' portions of a genomic clone is analyzed for sequences characteristic of promoter sequences. For instance, promoter sequence elements include the TATA box consensus sequence (TATAAT), which is usually 20 to 30 base pairs upstream of the transcription start site. In plants, further upstream from the TATA box, at positions −80 to −100, there is typically a promoter element with a series of adenines surrounding the trinucleotide G (or T) as described by Messing, et al. (1983) *Genetic Engineering in Plants*, Kosage, et al. (Eds.), pp. 221-227.

In preparing polynucleotide constructs, vectors, of the invention, sequences other than the promoter and the cojoined polynucleotide can also be employed. The polyadenylation region can be derived, for example, from a variety of plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates. See e.g., Buchman and Berg, *Mol. Cell Biol.* 8:4395-4405 (1988); Callis, et al., *Genes Dev.* 1:1183-1200 (1987). Use of maize introns Adh1-S intron 1, 2, and 6, the Bronze-1 intron are known in the art. See generally, "The Maize Handbook," Chapter 116, Freeling and Walbot, Eds., Springer, N.Y. (1994).

Specific initiation signals can aid in efficient translation of a Rubisco polynucleotide-encoding sequence of the present invention. These signals can include, e.g., the ATG initiation codon and adjacent sequences. In cases where a Rubisco polypeptide-encoding sequence, its initiation codon and upstream sequences are inserted into an appropriate expression vector, no additional translational control signals may be needed. However, in cases where only coding sequence (e.g., a mature protein coding sequence), or a portion thereof, is inserted, exogenous transcriptional control signals including the initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al. (1994) *Results Probl Cell Differ* 20:125-62; Bittner et al. (1987) *Methods in Enzymol* 153:516-544).

Secretion/Localization Sequences

Polynucleotides of the invention can also be fused, for example, in-frame to nucleic acids encoding a secretion/localization sequence, to target polypeptide expression to a desired cellular compartment, membrane, or organelle of a cell, or to direct polypeptide secretion to the periplasmic space or into the cell culture media. Such sequences are known to those of skill, and include secretion leader peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like.

Expression Hosts

In a further embodiment, the present invention relates to host cells containing the above-described constructs. The host cell can be a eukaryotic cell, such as a plant cell. Alternatively, the host cell can be a prokaryotic cell, such as a bacterial cell, and more typically, a cyanobacterial cell. Introduction of the construct into the host cell can be effected by calcium phosphate transfection, DEAE-Dextran mediated transfection, electroporation, or other common techniques (Davis, L., Dibner, M., and Battey, I. (1986) *Basic Methods in Molecular Biology*). Preferred host cells are those having the cellular machinery to carry out photosynthesis.

Expression Conditions

Host cells transformed with a Rubisco polynucleotide are optionally cultured under conditions to optimize carbon fixation by the host cell. The present invention provides a method of fixing carbon in a host cell, the method comprising:

(i) introducing the vector comprising a Rubisco rbcLS polynucleotide into one or more photosynthesizing host cell;

(ii) incubating the host cell to allow expression of a Rubisco rbcLS polynucleotide. Photosynthesizing host cells employed in the practice of the present invention include plant cells and cyanobacterial cells.

Suitable conditions for inducing carbon fixation in a cell capable of photosynthesis include exposure to light in the visible range. Typically, light having a wavelength in the range of from about 380 nm to 780 nm is employed. Transformed host cells are optimally incubated at a pH in the range of from about 7 to 11, and at a temperature in the range of from about 24° C. to about 32° C. Carbon dioxide can be provided in the form of atmospheric air, or with added $CO_2$ in an air/$CO_2$ mixture. Typically up to about 5% $CO_2$ is provided in a $CO_2$/air mixture. For large scale carbon fixation processes, the cells are typically incubated in a vessel that is transparent to light, under low shear agitation.

Fusion Polypeptides for Purification

Rubisco polypeptides of the present invention may also be expressed as part of a fusion polypeptide to facilitate purification of the encoded Rubisco polypeptide. Polynucleotides encoding such fusion polypeptides comprise a nucleic acid sequence corresponding to a Rubisco polynucleotide of the present invention that is fused-in frame to a purification facilitating domain. As used herein, the term "purification facilitating domain" refers to a domain that mediates purification of the polypeptide to which it is fused. Suitable purification domains include metal chelating peptides, histidine-tryptophan modules that allow purification on immobilized metals, a sequence which binds glutathione (e.g., GST), a hemagglutinin (HA) tag (corresponding to an epitope derived from the influenza hemagglutinin protein; Wilson et al. (1984) *Cell* 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the Rubisco polypeptide is useful to facilitate purification. One expression vector contemplated for use in the compositions and methods described herein provides for expression of a fusion protein comprising a polypeptide of the invention fused to a polyhistidine region separated by an enterokinase cleavage site. The histidine residues facilitate purification on IMIAC (immobilized metal ion affinity chromatography, as described in Porath et al. (1992) *Protein*

*Expression and Purification* 3:263-281) while the enterokinase cleavage site provides a means for separating the Rubisco polypeptide from the fusion protein. pGEX vectors (Promega; Madison, Wis.) may also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusions) followed by elution in the presence of free ligand.

Production and Recovery of Rubisco Polypeptides

Following transduction of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well known to those skilled in the art.

As noted, many references are available for the culture and production of many cells, including cells of bacterial, plant, animal (especially mammalian) and archebacterial origin. See e.g., Sambrook, Ausubel, and Berger (all supra), as well as Freshney (1994) *Culture of Animal Cells, a Manual of Basic Technique*, third edition, Wiley-Liss, New York and the references cited therein; Doyle and Griffiths (1997) *Mammalian Cell Culture: Essential Techniques* John Wiley and Sons, NY; Humason (1979) *Animal Tissue Techniques*, fourth edition W. H. Freeman and Company; and Ricciardelli, et al., (1989) In vitro *Cell Dev. Biol.* 25:1016-1024. For plant cell culture and regeneration, Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); Jones, ed. (1984) *Plant Gene Transfer and Expression Protocols*, Humana Press, Totowa, N.J. and *Plant Molecular Biology* (1993) R. R. D. Croy, Ed. Bios Scientific Publishers, Oxford, U.K. ISBN 0 12 198370 6. Cell culture media in general are set forth in Atlas and Parks (eds) *The Handbook of Microbiological Media* (1993) CRC Press, Boca Raton, Fla. Additional information for cell culture is found in available commercial literature such as the *Life Science Research Cell Culture Catalogue* (1998) from Sigma-Aldrich, Inc (St Louis, Mo.) ("Sigma-LSRCCC") and, e.g., *The Plant Culture Catalogue* and supplement (1997) also from Sigma-Aldrich, Inc (St Louis, Mo.) ("Sigma-PCCS"). Further details regarding plant cell transformation and transgenic plant production are found below.

Rubisco polypeptides of the present invention can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing the configuration of the mature protein. Finally, high performance liquid chromatography (HPLC) can be employed in the final purification steps. In addition to the references noted supra, a variety of purification methods are well known in the art, including, e.g., those set forth in Sandana (1997) *Bioseparation of Proteins*, Academic Press, Inc.; and Bollag et al. (1996) *Protein Methods*, $2^{nd}$ *Edition* Wiley-Liss, NY; Walker (1996) *The Protein Protocols Handbook* Humana Press, NJ, Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice* $3^{rd}$ *Edition* Springer Verlag, NY; Janson and Ryden (1998) *Protein Purification: Principles, High Resolution Methods and Applications, Second Edition* Wiley-VCH, NY; and Walker (1998) *Protein Protocols on CD-ROM* Humana Press, NJ.

In some cases it may be desirable to produce the Rubisco polypeptides of the invention in a large scale suitable for industrial and/or commercial applications. In such cases bulk fermentation procedures are employed. Briefly, a Rubisco polynucleotide, is cloned into an expression vector, such as, for example, the vector described in U.S. Pat. No. 5,955,310 to Widner et al. "METHODS FOR PRODUCING A POLYPEPTIDE IN A BACILLUS CELL. After inserting the polynucleotide of interest into a vector, the vector is transformed into a bacterial, e.g., a *Bacillus subtilis* strain PL1801IIE (amyE, apr, npr, spoIIE::Tn917) host. The introduction of an expression vector into a *Bacillus* cell may, for instance, be effected by protoplast transformation (see, e.g., Chang and Cohen (1979) *Molecular General Genetics* 168: 111), by using competent cells (see, e.g., Young and Spizizin (1961) *Journal of Bacteriology* 81:823, or Dubnau and Davidoff-Abelson (1971) *Journal of Molecular Biology* 56:209), by electroporation (see, e.g., Shigekawa and Dower (1988) *Biotechniques* 6:742), or by conjugation (see, e.g., Koehler and Thome (1987) *Journal of Bacteriology* 169: 5271).

The transformed cells are cultivated in a nutrient medium suitable for production of the polypeptide using methods that are known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The secreted polypeptide can be recovered directly from the medium.

The resulting polypeptide may be isolated by methods known in the art. For example, the polypeptide may be isolated from the nutrient medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., Bollag et al. (1996) *Protein Methods*, $2^{nd}$ *Edition* Wiley-Liss, NY; Walker (1996) *The Protein Protocols Handbook* Humana Press, NJ; Bollag et al. (1996) *Protein Methods 2nd Edition* Wiley-Liss, NY; Walker (1996) *The Protein Protocols Handbook* Humana Press, NJ).

Cell-free transcription/translation systems can also be employed to produce polypeptides using DNAs or RNAs of the present invention. Several such systems are commercially available. A general guide to in vitro transcription and translation protocols is found in Tymms (1995) *In vitro Transcription and Translation Protocols: Methods in Molecular Biology* Volume 37, Garland Publishing, NY.

The foregoing and other aspects of the invention may be better understood in connection with the following non-limiting examples.

EXAMPLES

Example 1

Expression of Ribulose 1,5-Bisphosphate Carboxylase/Oxygenase from *E. coli*

Figure 2:
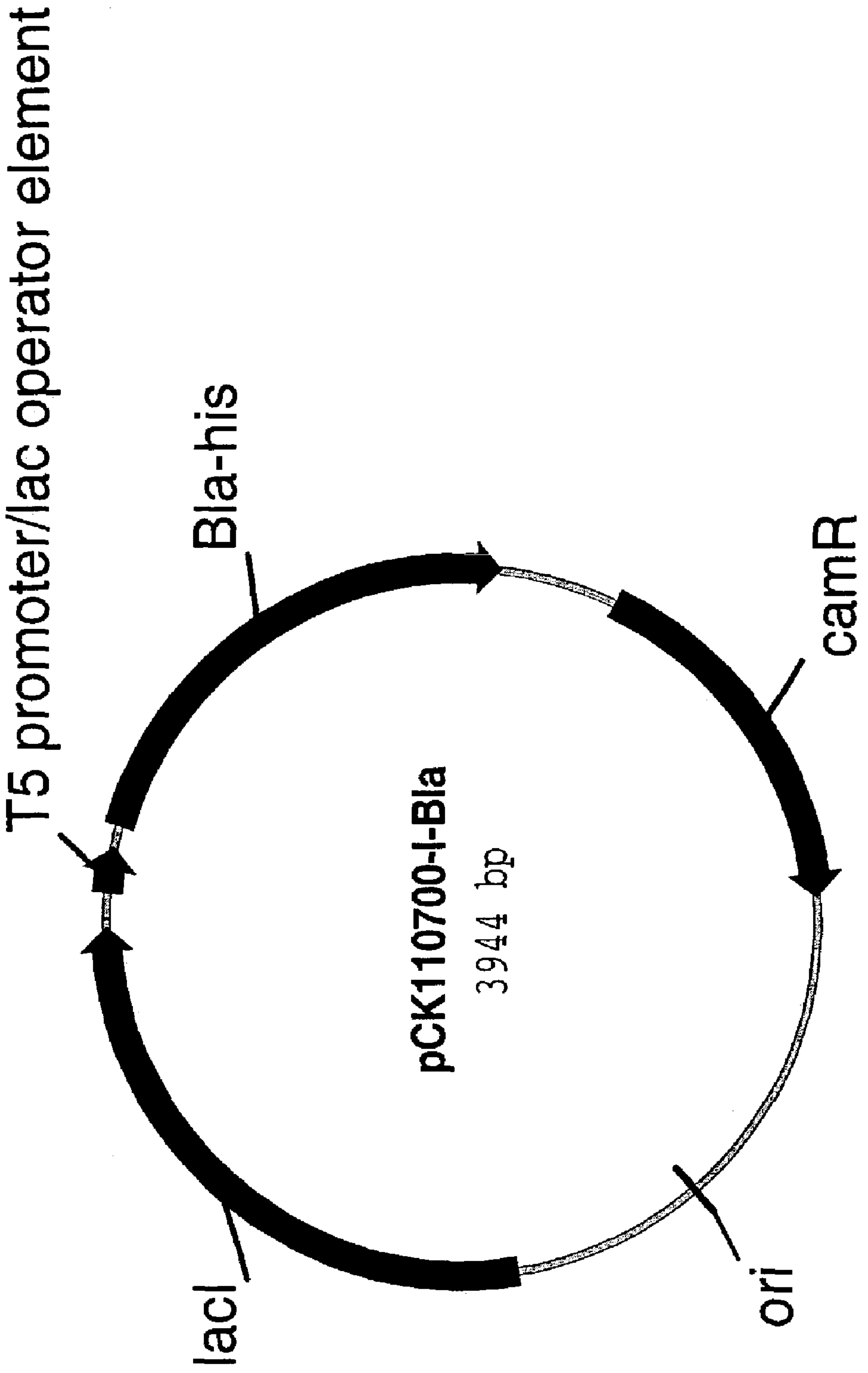
FIG. 2 depicts Vector pCK110700-I-Bla.

Transformation:

Rubisco polynucleotides of the present invention that encode both Rubisco large and small subunits were cloned into vector pCK 110700-I-Bla depicted in FIG. 2, then transformed into *E. Coli* host strain NM522 (Stratagene, La Jolla, Calif.) using heat shock treatment at 42° C.

Cell Growth:

200 μl of cell growth media (32 g casein hydrosylate, 6 g $KH_2HPO_4$, 6 g $Na_2HPO_4$, and 0.68 g $K_2SO_4$) was aliquoted into a Nunc steril 96 well flat bottomed plate. Cultures were inoculated with 160 μl/well cell media containing 1% glucose and 30 μg/ml chloramphenicol. Plates were sealed with Qiagen Air Pore Tape and a sterile Nunc plate lid was placed over the plates. The plates were shaken at 37° C. in a Kuhner Shaker.

Induction:

The next day, 290 μl of cell growth media with 1% glucose and 30 μg/mL chloramphenicol ("inducing media") was added to each well of a 96 well MegaTitre plate. Cells from the overnight cultures were mixed, then inoculated into the wells (10 μl/well) of the Megatitre plates containing the inducing media. The plates were sealed with Air Pore Tape and shaken at 37° C. in a Kuhner Shaker for 1 to 2 hours until reaching an OD600 of 0.2 to 0.6, after which 30 μl of 1 mM isoprophylthio-β-galactoside (IPTG) was added to each well. The plates were resealed and allowed to incubate on the shaker for 6 hours. The plates were then centrifuged at 3300 rpm for 15 minutes at 4° C. The cell pellets were stored at −20° C. until assayed.

Cell Lysis:

Cells were lysed just prior to assaying. 300 μl of lysis buffer (50 mM HEPES buffer pH 7.5, 300 mM KCl, 20 mM $MgCl_2$, 1 mM DTT, 5% Glycerol, 1 μl ReadyLyse Lysozyme per ml lysis buffer, 20 μl 10 mg/ml PMBS per ml lysis buffer, 1 μl 200 mM PMSF in isopropanol per ml lysis buffer) was added to each well of the plates. The plates were then sealed and shaken until the cells were lysed (30 minutes to 2 hours).

Example 2

Assay for Presence of Rubisco Activity

The following assay was used to ascertain the presence of Rubisco activity. 100 μl cell lysate from Example 1 was transferred into the wells of a 96 well flat bottomed plate. A solution of $^{14}C$ sodium bicarbonate was prepared by mixing 1 ml of a $^{14}C$ sodium bicarbonate solution, 1 mCi/1 ml, (Sigma-Aldrich, Inc., St. Louis, Mo.) with 63 ml of 16 mM $^{12}C$ sodium bicarbonate. A 330 mM stock solution of ribulose 1,5-bisphosphate was prepared by dissolving 100 mg ribulose 1,5-bisphosphate (Sigma-Aldrich, Inc., St. Louis, Mo.) in 1 ml water. The 330 mM ribulose 1,5-bisphosphate stock solution was diluted to make a 6 mM stock solution. 50 μl of a 50:50 6 mM Ribulose 1,5-Bisphosphate: $^{14}C$ sodium bicarbonate solution was added to each well of the plate. After 1.5 to 2 hours, 100 μl 1N HCl was added to each well. The plates were then placed in a 70° C. oven overnight to dry.

A Nunc nylon transfer membrane was placed into the bottom of a Nunc Omnitray (Nalge Nunc International, Rochester, N.Y.) and 3 μl of cell lysate/Ribulose 1,5-Bisphosphate: $^{14}C$ sodium bicarbonate mixture from each well of the flat bottomed plate was transferred onto the nylon membrane. The membrane was allowed to dry, after which it was placed in a Molecular Dynamics Phosphorimaging Cassette (Amersham Biosciences, Piscataway, N.J.). The cassette was exposed overnight and the phosphorscreen was removed from the cassette and scanned in a Molecular Dynamics Phosphorimager using standard methods.

$^{14}C$ incorporation at a level greater than a negative control, which was a vector without a Rubisco polynucleotide (rbcLS) insert, indicated the presence of Rubisco activity.

Example 3

Assay to determine Specific Activity of Ribulose 1,5-Bisphosphate Carboxylase/Oxygenase The value that roughly describes the specific activity of Rubisco is CPM/nM Rubisco. The following assay utilizes an active site titration with 2-carboxyarabinitol 1,5-bisphosphate (CABP) along with a time course $^{14}CO_2$ incorporation assay to roughly determine Rubisco specific activity.

50 μl aliquots of cell lysate from Example 1 were dispensed into polypropylene 96 well plates. Various concentrations of CABP inhibitor were added to the wells. 50 μl of the 50:50 Ribulose 1,5-bisphosphate ("RuBP"): $^{14}C$ sodium bicarbonate solution was added to each well of the plates. In half the wells the reaction was stopped after 10 minutes by adding 50 μl of 1 N HCl. After 20 minutes, the reaction was stopped in the remaining wells by adding 50 μl of 1 N HCl. The plates were dried overnight at 70° C. The following day, 150 μl of 10 mM HCl was added to each well to resuspend the mixtures. The plates were blotted onto a nylon membrane, then exposed to phosphorscreens prior to phosphorimaging as described in Example 2.

Initial rates were monitored at saturating RuBP concentrations (1 mM) for the carboxylation reaction run for 5 minutes, with samples take at the following timepoints: 5=0, 1 minute, 2 minutes, 3 minutes, 4 minutes, and 5 minutes. The rates were determined as counts incorporated per minute or as density per minute. Rubisco polypeptide sample concentrations were determined using CABP titration as described below, and/or by quantitative western blots.

To compute Rubisco polypeptide sample concentrations from CABP titrations, Intensity vs. time was plotted for each concentration of CABP. From the slope of each plot (i.e., each plot corresponds to a fixed concentration of CABP), the value for CPM (i.e., counts per minute) was determined. A plot of CPM/min vs. concentration of CABP was then made. The x-intercept provided the concentration for Rubisco. The specific activity was computed for each Rubisco polypeptide as CPM/weight Rubisco.

The specific activity values for the enzymes corresponding to Rubisco polypeptides of the present invention are provided in Table 3.

TABLE 3

Rubisco Specific Activity (counts per minute ("cpm")/min/mg)

| Clone Name | Rubisco Specific Activity (cpm/min/mg Rubisco) |
|---|---|
| RT24 (Encoded by SEQ ID ID NO: 4) | 180 |
| RT25 (Encoded by SEQ ID NO: 7) | 300 |
| RT28 (Encoded by SEQ ID NO: 10) | 600 |
| RT30 (Encoded by SEQ ID NO: 13) | 600 |
| RT106 (Encoded by SEQ ID NO: 106) | 270 |
| RT108 (Encoded by SEQ ID NO: 19) | 180 |
| RT111 (Encoded by SEQ ID NO: 22) | 300 |
| RT113 (Encoded by SEQ ID NO: 25) | 480 |
| RT115 (Encoded by SEQ ID NO: 28) | 300 |
| RT116 (Encoded by SEQ ID NO: 31) | 300 |
| RT117 (Encoded by SEQ ID NO: 34) | 300 |
| RT118 (Encoded by SEQ ID NO: 37) | 300 |
| *Synechococcus* PCC 6301 (wildtype, encoded by SEQ ID NO: 1) | 300 |
| F2A-10 (encoded by SEQ ID NO: 40) | 1710 |
| F2A-16 (encoded by SEQ ID NO: 43) | 1530 |
| F2A-20 (encoded by SEQ ID NO: 46) | 580 |
| F2B-2 (encoded by SEQ ID NO: 49) | 1280 |
| F2B-3 (encoded by SEQ ID NO: 52) | 1280 |

Example 4

Michaelis-Menten Kinetics Characterization of Rubisco Polypeptides $V_{max}$ and $K_M$ were determined by Michaelis-Menten kinetics for the Rubisco polypeptides encoded by SEQ ID NO: 1, 10, and 40. $^{14}CO_2$ incorporation was measured as described in Example 3 at various timepoints. Rates were measured over a range of RuBP concentrations to obtain rate (V) vs. [RuBP (substrate)] plots that provided a best fit to the Michaelis-Menten kinetic equation:

$$V = V_{max}\frac{[\text{substrate }(RuBP)]}{[\text{substrate }(RuBP)] + K_M}$$

Using GraphPad Prizm software, the V. vs. [RuBP] plots were fit to the Michaelis-Menten kinetic equation and Vmax and $K_M$ were extracted. $K_{cat}$ (i.e., $V_{max}$/[Rubisco Polypeptide]) was determined from the previously determined $V_{max}$. Rubisco polypeptide concentration was determined from a quantitative western in accordance with methods known to those having ordinary skill in the art. The kinetic characterization data is provided in Table 4.

TABLE 4

Kinetic Parameters for Rubisco Polypeptides

| Rubisco Polypeptide (RuBP) | Kcat ($s^{-1}$) | $K_M$ (μM RuBP) | Kcat/$K_M$ | kcat/$K_M$ normalized to wildtype *Synechococcus* sp. PCC6301 |
|---|---|---|---|---|
| *Synechococcus* sp. PCC6301 (wildtype encoded by SEQ ID NO: 1) | 6.3 | 78.6 | 0.08 | 1 |
| RT28 (encoded by SEQ ID NO: 10) | 2.6 | 20.8 | 0.13 | 1.6 |
| F2A-10 (encoded by SEQ ID NO: 40) | 26.5 | 58.5 | 0.45 | 5.7 |

Example 5

Transformation of Rubisco Polynucleotides into *Snechocystis* sp.

Figure 3:
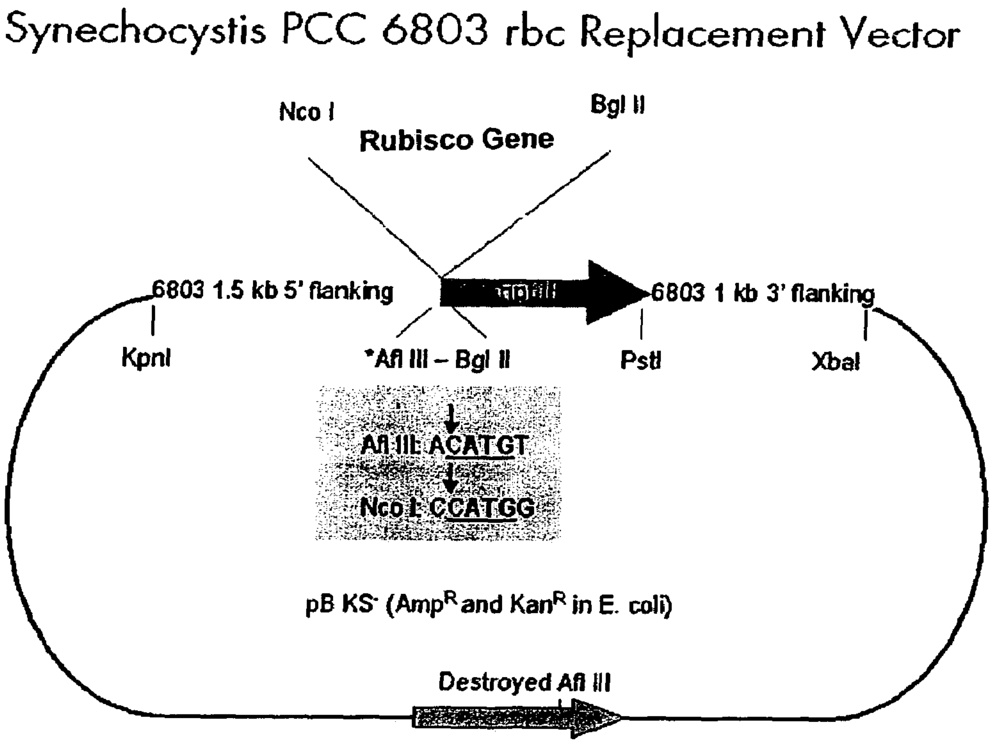
FIG. 3 depicts Vector pGR-1.

Rubisco polypeptides of the present invention were transformed into *Synechocystis* sp. PCC 6803 using the Gene replacement vector pGR-1 depicted in FIG. 3. The vector contains 1.5 kb of upstream sequence of *Synechocystis* sp. PCC6803 wildtype Rubisco gene, rbcLS, which contains the wildtype promoter and ribosome binding site. The upstream sequence also provides for homologous recombination to replace the wildtype Rubisco gene in *Synechocystis* sp. PCC 6803. The vector was designed so that the wildtype rubisco coding sequence is replaced with SEQ ID NO: 10 (clone RT28) via a double crossover in both 5' and 3' flanking regions. The vector was a pBluescript II KS (2.96 kb) from Invitrogen, Inc. (Carlsbad, Calif.) with the internal Af1III site destroyed. The kanamycin resistance cassette, nptII, was cloned from pUC4K. The polynucleotide sequence corresponding to SEQ ID NO: 10 was cloned into this gene replacement vector and transformed into *Synechocystis* 6803 At kanamycin 150 μg/ml, by a PCR check, it was determined to have replaced the wildtype Rubisco gene in about 50% of the clones.

Other vectors were designed for transforming Rubisco polynucleotides into *Synechocystis* sp. pDNR-1 (BD Biosciences, Clontech, Palo Alto, Calif.) is modified to remove the loxP sites, replace the pUC origin of replication with a p15A origin of replication, and remove the chloramphenicol resistance cassette ($Cm^R$). In addition, 5' and 3' sequences flanking *Synechocystis* sp. rbcLS are inserted to create gene replacement vectors, pGR-2a, pGR-2b, and pGR-3a. Vector pGR-2a contains the 5' and 3' sequences flanking *Synechocystis* sp. rbcLS depicted as SEQ ID NOS: 58 and 59, respectively. Vector pGR-2b contains the 5' sequence flanking *Synechocystis* sp. rbcLS depicted as SEQ ID NOS: 60, and the same 3' flanking sequence as in pGR-2a (i.e., SEQ ID NO: 59). Vector pGR-3a contains the same 3' rbcLS flanking sequence as pGR-2a, and the 3' rbcLS flanking sequence depicted as SEQ ID NO: 61.

*Synechocystis* sp. PCC 6803 is transformed with the Rubisco polynucleotides of the present invention. A 20-50 ml PCC 6803 culture are grown on BG11+16 mM $NaHCO_3$ for about 4 to 5 days and cultured until reaching an OD730 of about 1 to 1.5 (~$10^8$ cells/ml). All steps are carried out under visible light. 100 μl of cells (clumps broken up by mixing) are transferred into the wells of a sterile 96-well plate. 1-7 μg DNA (plasmid) is added and mixed with the cells. The plate is left uncovered under light at room temperature for about 24 hours. On day 2, all cells are plated directly on selective medium (BG11 agar+10 μg/ml kanamycin+16 mM $NaHCO_3$) and incubated under light at room temperature prior to picking.

Example 6

Whole Cell $CO_2$ Fixation Assay

Figure 4:
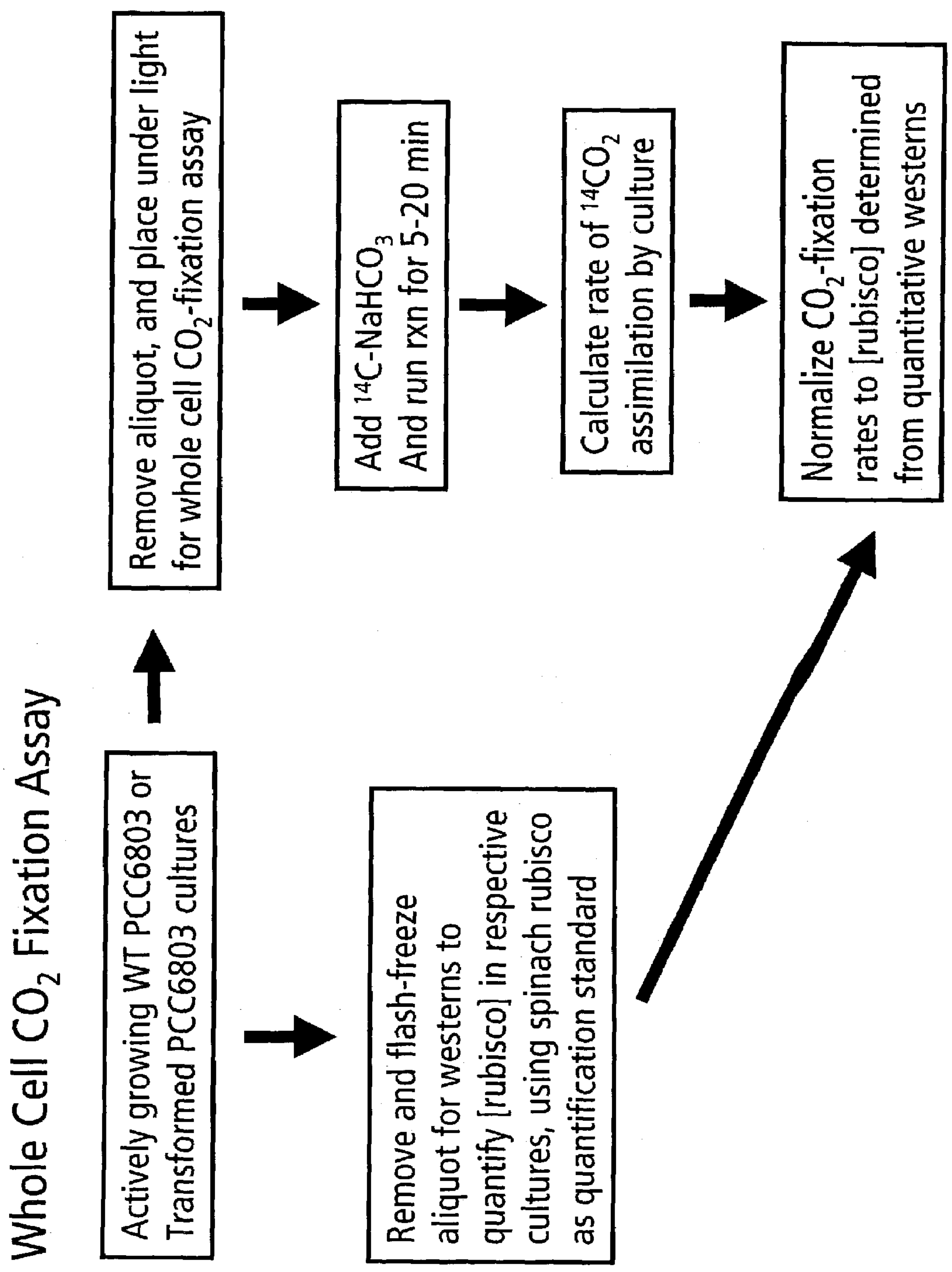
FIG. 4 provides a schematic description of the Whole Cell $CO_2$ fixation assay described in Example 6.

The whole cell CO2 fixation assay measures the flux through the Calvin cycle in a live-photosynthesizing cell. The difference between this assay and the in vitro assays described above is that RuBP is not added to the cells. The cells have the capability to regenerate RuBP using their endogenous Calvin cycle machinery. A schematic of the assay is provided in FIG. 4.

*Synechocystis* sp. PCC 6803 was cultured at room temperature, under light, and in BG11, 16 mM bicarbonate. After reaching an OD730 of about 0.45 to 0.7, 600 μl of culture was placed into a short glass vial with cap and placed on a light box for about 15 minutes. Add 50 μl of a $^{14}C$ sodium bicarbonate solution, 1 mCi/1 ml, (Sigma-Aldrich, Inc., St. Louis, Mo.) to 450 μl of cell. Take 50 μl of the culture/14C-NaHCO3 mixture was quenched in 100 μl of 1 N HCl at various timepoints (e.g., t=0 minutes, 5 minutes, 10 minutes, 15 minutes, and so on) on a NUNC Heat Resistant (96 well) plate. Dry the plate completely overnight in an oven at −70° C. 150 μl of scintillation cocktail was added, and the vials were maintained away from the light. The plates were read by a scintillation counter. Normalized rates (CPM/min) to Rubisco concentrations obtained by quantitative western.

While the above $CO_2$ fixation assay was performed, 150 μl of culture was removed and quickly spun down to remove all supernatant for use in a western blot quantitation assay. The cell pellet was resupended in 32.5 μl of water, 12.5 μl of NP0007 NUPAGE LDS Sample Buffer (4×) (Invitrogen, Carlsbad, (Calif.). The resuspended mixture was boiled for about 10 minutes, after which 10 μl of NP0004 NUPAGE Sample Reducing Agent (10×) reducing agent (Invitrogen, Carlsbad, Calif.) was added. The boiled samples were flash frozen in a mixture of ethanol and dry ice, then stored at −20° C.

A quantitative western blot was done using Spinach Rubisco (Sigma-Adrich, St. Louis, Mo.) as a standard, to quantify the amount of Rubisco polypeptide in the $CO_2$ fixation assay.

All publications, patents, patent applications, and other documents cited in this application are incorporated by reference in their entirety for all purposes to the same extent as if each individual publication, patent, patent application, or other document were individually indicated to be incorporated by reference for all purposes.

While preferred embodiments of the invention have been illustrated and described, it will be readily appreciated that various changes can be made therein without departing from the spirit and scope of the invention.

What is claimed is:

1. An isolated or recombinant Rubisco large subunit polypeptide comprising an amino acid sequence that has at least 99% sequence identity-to SEQ ID NO: 11 and at least one of the following residues: (a) an isoleucine at position 454, (b) a valine at position 84, (c) a lysine at position 158, (d) a leucine at position 166, and (e) a methionine at position 317.

2. The isolated or recombinant polypeptide of claim 1, which comprises the amino acid sequence listed in SEQ ID NO: 11 or the amino acid sequence listed in SEQ ID NO:11 having conservative mutations at less than 1% of the positions.

3. The isolated or recombinant polypeptide of claim 1, wherein the amino acid sequence further comprises at least one amino acid residue selected from the group consisting of:

D at position 92; F at position 93; L at position 113; L at position 116; L at position 117; L at position 127; A at position 129; V at position 137; I at position 139; Y at position 141; L at position 142; S at position 149; G at position 154; M at position 209; Q at position 219; E at position 220; E at position 223; A at position 225; T at position 232; Q at position 246; E at position 249; A at position 252; I at position 257; T at position 259; G at position 269; S at position 276; Y at position 280; L at position 286; A at position 297; K at position 303; T at position 304; Q at position 322; T at position 325; R at position 336; Q at position 337; T at position 338; I at position 343; Q at position 345; L at position 346; S at position 349; F at position 350; P at position 352; E at position 353; N or T at position 356; N at position 359; D at position 362; G at position 366; F at position 372; A at position 373; A at position 389; I at position 415; and R at position 450.

4. The isolated or recombinant polypeptide of claim 1, wherein the amino acid sequence comprises at least two amino acid residues selected from the group consisting of: V at position 84, K at position 158, L at position 166, M at position 317, and I at position 415.

5. An isolated polypeptide having Rubisco specific activity comprising the Rubisco large subunit polypeptide of claim 1, wherein the amino acid sequence has an isoleucine at position 454 and wherein the polypeptide is capable of a higher $k_{cat}$ than the wild-type polypeptide encoded by SEQ ID NO:1.

6. An isolated polypeptide having Rubisco specific activity comprising the Rubisco large subunit polypeptide of claim 1, wherein the amino acid sequence has a valine at position 84 and wherein the polypeptide is capable of a lower $K_M$ than the wild-type polypeptide encoded by SEQ ID NO:1.

7. An isolated polypeptide having Rubisco specific activity comprising the Rubisco large subunit polypeptide of claim 1, wherein the amino acid sequence has a lysine at position 158 and wherein the polypeptide is capable of a lower $K_M$ than the wild-type polypeptide encoded by SEQ ID NO:1.

8. An isolated polypeptide having Rubisco specific activity comprising the Rubisco large subunit polypeptide of claim 1, wherein the amino acid sequence has a leucine at position 166 and wherein the polypeptide is capable of a lower $K_M$ than the wild-type polypeptide encoded by SEQ ID NO:1.

9. An isolated polypeptide having Rubisco specific activity comprising the Rubisco large subunit polypeptide of claim 1, wherein the amino acid sequence has a valine at position 84 and wherein the polypeptide is capable of a lower $K_M$ than the wild-type polypeptide encoded by SEQ ID NO:1.

* * * * *